(12) United States Patent
Birault et al.

(10) Patent No.: US 9,242,972 B2
(45) Date of Patent: Jan. 26, 2016

(54) COMPOUNDS

(71) Applicant: Glaxo Group Limited, Brentford, Middlesex (GB)

(72) Inventors: Veronique Birault, Stevenage (GB); Amanda Jennifer Campbell, Stevenage (GB); Stephen Harrison, Stevenage (GB); Joelle Le, Stevenage (GB); Lena Shukla, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/394,113

(22) PCT Filed: Apr. 25, 2013

(86) PCT No.: PCT/EP2013/058667
§ 371 (c)(1),
(2) Date: Oct. 13, 2014

(87) PCT Pub. No.: WO2013/160419
PCT Pub. Date: Oct. 31, 2013

(65) Prior Publication Data
US 2015/0065507 A1    Mar. 5, 2015

(30) Foreign Application Priority Data

Apr. 27, 2012 (GB) .................................. 1207406.8

(51) Int. Cl.
*C07D 213/76* (2006.01)
*C07D 405/12* (2006.01)
*C07D 413/12* (2006.01)
*A61K 31/47* (2006.01)
*A61K 31/5395* (2006.01)
*C07D 413/14* (2006.01)
*C07D 405/14* (2006.01)

(52) U.S. Cl.
CPC ............ *C07D 413/14* (2013.01); *C07D 213/76* (2013.01); *C07D 405/12* (2013.01); *C07D 405/14* (2013.01); *C07D 413/12* (2013.01)

(58) Field of Classification Search
None
See application file for complete search history.

(56) References Cited

FOREIGN PATENT DOCUMENTS

WO    WO 2006/038594      *   4/2006
WO    WO 2006/038594 A1       4/2006

OTHER PUBLICATIONS

Ono Pharmaceutical Co., Chemical Abstract 144:390559, 2006 (Abstract of WO 2006/038594).*
Kumar, et al. Probe Reports from the NIH Molecular Libraries Program, pp. 1-22 (2010). http://www.ncbi.nlm.nih.gov/books/NBK56239/.

* cited by examiner

*Primary Examiner* — Zinna Northington Davis
(74) *Attorney, Agent, or Firm* — Dara L. Dinner; Theodore R. Furman

(57) ABSTRACT

The present invention is directed to novel retinoid-related orphan receptor gamma (RORγ) modulators, processes for their preparation, pharmaceutical compositions containing these modulators, and their use in the treatment of inflammatory, metabolic and autoimmune diseases mediated by RORγ.

28 Claims, No Drawings

COMPOUNDS

This application is a §371 national stage entry of International Application No. PCT/EP2013/058667, filed 25 Apr. 2013, which claims priority of GB Application No. 1207406.8, filed 27 Apr. 2012, which are incorporated herein in their entireties.

FIELD OF THE INVENTION

The present invention is directed to novel retinoid-related orphan receptor gamma (RORγ) modulators, processes for their preparation, pharmaceutical compositions containing these modulators, and their use in the treatment of inflammatory, metabolic and autoimmune diseases mediated by RORγ.

BACKGROUND OF THE INVENTION

Retinoid-related orphan receptors (RORs) are transcription factors that form a subgroup of the nuclear receptor superfamily (*Adv. Dev. Biol.* 2006, 16, 313-355). This subgroup consists of three members: ROR alpha (RORα), ROR beta (RORβ) and ROR gamma (RORγ). RORα and RORβ have approximately 55% homology in the ligand binding domains to RORγ. RORs contain four principal domains shared by the majority of nuclear receptors: an N-terminal A/B domain, a DNA-binding domain, a hinge domain and a ligand binding domain.

The RORα, RORβ and RORγ genes have been mapped to human chromosomes 15q22.2, 9q21.13 and 1q21.3, respectively. Each ROR gene generates several isoforms, which differ only in their N-terminal A/B domain. To date, five splice variants have been recorded for RORγ and two isoforms of this member of the ROR family have been identified: RORγ1 and RORγ2 (also known as RORγt). RORγ is a term used to describe RORγ1 and/or RORγt.

While RORγ1 is expressed in a variety of tissues including thymus, muscle, kidney and liver, RORγt is exclusively expressed in the cells of the immune system and has a critical role in thymopoiesis, development of several secondary lymphoid tissues and Th17 lineage specification.

RORγt has been identified as a key regulator of Th17 cell differentiation (A. Jetten, *Nuclear Receptor Signalling* 2009, 7, 1-32). Th17 cells are a recently discovered subset of T helper cells which preferentially produce cytokines IL-17A, IL-17F, IL-21 and IL-22. RORγt also induces transcription of the gene encoding IL-17A and IL-17F in näive CD4+ T helper cells, iNKT and NKT (*Mucosal Immunol.* 2009, 2(5), 383-392; *J. Immunol.* 2008, 180, 5167-5171), γδT cells (*Am. J. Respir. Crit. Care Med.* 2010, 182, 464-476), CD8+ T cells (*J. Leukocyte Biol.* 2007, 82, 354-360) and finally CD4− CD8− TCRαβ+ T cells (*J. Immunol.* 2008, 181, 8761-8766). Additional immune cells such as eosinophils, neutrophils and macrophages can also be a source of IL-17A in allergic inflammation related to asthma (*J. Allergy Clin. Immunol.* 2001, 108, 430-438; J. Immunol. 2008, 181, 6117-6124; *Immunity* 2004, 21, 467-476).

Th17 cells and their products have been shown to be associated with the pathology of a number of human inflammatory and autoimmune disorders. IL-17A and IL-17F are implicated in numerous immune and inflammatory responses primarily as pro-inflammatory regulators inducing the expression of cytokines, chemokines, adhesion molecules, mucin genes and growth factors. There is emerging evidence that an increase in IL-17A level is closely associated with a range of chronic inflammatory diseases such as rheumatoid arthritis (*Curr. Opin. Investig. Drugs* 2009, 10, 452-462), multiple sclerosis (*Allergol. Int.* 2008, 57 (2), 115-120), inflammatory bowel diseases (*J. Inflamm. Res.* 2010, 3, 33-44), uveitis, psoriasis (*Sci. Transl. Med.* 2010, 2(52)) and lung diseases (*Prog. Respir. Res. Basel* 2010, 39, 141-149; *Resp. Research* 2010, 11 (78), 1-11).

There is considerable evidence suggesting that Th17 cells/IL-17 play a key role in the pathogenesis of asthma. In asthmatic patients, both RORγt and IL-17A expression levels have been shown to be increased in sputum (*Chin. Med. J.* 2005, 118, 953-956; *Resp. Res.* 2006, 7(135), 1-9), lung (*J. Allergy Clin. Immunol.* 2003, 111(6), 1293-1298), bronchoalveolar lavage (BAL) fluids and peripheral blood (*Immunol. Invest* 2009, 38, 652-664; *Int. Arch. Allergy Immunol.* 2005, 137 (suppl. 1), 51-54) and levels directly correlate with disease severity (*Int. Arch. Allergy Immunol.* 2010, 151, 297-307). In addition to IL-17A, a recent study has shown that a further cytokine of the IL-17 family, IL-17F, may have a crucial role in allergic airway inflammation and hence have key implications in airway diseases, such as asthma. The overexpression of the IL-17F gene in mice airways was associated with airway neutrophilia, cytokine induction, an increase in airway hyperreactivity and mucus hypersecretion (*Inflamm. Allergy Drug Targets* 2009, 8, 383-389). Evidence of role of Th17 cells in allergens has been discussed in *Int. Immunopharmacol.* 2010, 10, 226-229.

The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (*J. Exp. Med.* 2008, 205, 1517-1522; *Cell. Mol. Immunol.* 2010, 7, 182-189). There is also evidence that Th17 cells are activated during the disease process and are responsible for recruiting other inflammatory cells types, especially neutrophils, to mediate pathology in the target tissues (*Annu. Rev. Immunol.* 2009, 27, 485-517). RORγt plays a critical role in the pathogenic responses of Th17 cells (Cell 2006, 126, 1121-1133). RORγt deficient mice show very few Th17 cells. Further support for the role of RORγt in the pathogensis of autoimmune or inflammatory diseases can be found in the following references: *Immunity* 2007, 26, 643-654; *Nat. Rev. Immunol.* 2006, 6, 205-217; *J. Immunol.* 2009, 183, 7169-7177; *Brain Pathol.* 2004, 14, 164-174; *Brain* 2007, 130, 1089-1104; *Nat. Rev. Immunol.* 2008, 8, 183-192.

In light of the role RORγ plays in the pathogenesis of diseases, it is desirable to prepare compounds that modulate RORγ activity and hence have utility in the treatment of inflammatory, metabolic and autoimmune diseases mediated by RORγ, such as the respiratory diseases asthma, chronic obstructive pulmonary disease (COPD) and bronchitis, allergic diseases including allergic rhinitis and atopic dermatitis, cystic fibrosis and lung allograph rejection.

SUMMARY OF THE INVENTION

According to the invention, there is provided novel retinoid-related orphan receptor gamma (RORγ) modulators, processes for their preparation, pharmaceutical compositions comprising these modulators, and their use in the treatment of inflammatory, metabolic and autoimmune diseases mediated by RORγ. More specifically, the present invention is directed to compounds of formula (I), and to pharmaceutically acceptable salts thereof:

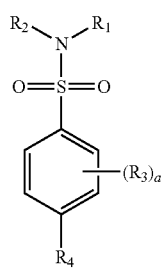

wherein:
R₁ is

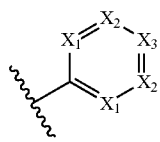

each $X_1$ is independently N or $CR_a$;
each $X_2$ is independently N or $CR_b$;
$X_3$ is N or CRC;
each $R_a$ is independently selected from H, $CF_3$, halo, $C_{1-4}$alkyl and $C_{1-4}$alkoxy;
each $R_b$ is independently selected from H, $CF_3$, halo, $CH_3$ and $OCH_3$;
each $R_c$ is independently selected from H, $C_{1-4}$alkyl, $C_{2-4}$alkenyl, $C_{1-4}$alkoxy, $CF_3$, halo, CN, $C_{3-6}$cycloalkyl and $C_{3-6}$heterocycloalkyl;
$R_2$ is selected from the group consisting of $C_{3-5}$alkyl, —$CH_2C_{3-4}$cycloalkyl, and —$CH_2$oxetanyl; each $R_3$ is independently selected from the group consisting of $C_{1-3}$alkyl, $C_{1-3}$alkoxy, halo, OH and $CH_2OH$;
$R_4$ is the group —$X(CHR_5)_bR_6$;
X is selected from the group consisting of O, $CH_2$, CHOH and $CHCH_2OH$;
each $R_5$ is independently selected from the group consisting of H, OH and $CH_2OH$;
$R_6$ is isoxazole, morpholine, piperidine, pyrrolidine, tetrahydro-2H-pyran, tetrahydrofuran, —$NHR_7$ or is a 5- or 6-membered heteroaryl group, wherein $R_6$ may be unsubstituted or substituted with one or two substitutents independently selected from halo and $CH_3$;
$R_7$ is oxetanyl or tetrahydrofuran, wherein $R_7$ may be unsubstituted or substituted with one or two substitutents independently selected from halo and $CH_3$;
a is 0, 1 or 2;
b is 0, 1 or 2;
with the proviso that $R_1$ contains one or two nitrogen atoms.

In one aspect, the present invention provides a pharmaceutical composition comprising a) a compound of formula (I), or a pharmaceutically acceptable salt thereof, and b) one or more pharmaceutically acceptable excipients.

In a further aspect, the present invention provides a compound of formula (I), or a pharmaceutically acceptable salt thereof, for use in therapy.

Compounds of formula (I), and pharmaceutically acceptable salts thereof, are modulators of RORγ and can be useful in the treatment of inflammatory, metabolic and autoimmune diseases mediated by RORγ, such as asthma, chronic obstructive pulmonary disease (COPD) and bronchitis, allergic diseases including allergic rhinitis and atopic dermatitis, cystic fibrosis, lung allograph rejection, multiple sclerosis, rheumatoid arthritis, juvenile rheumatoid arthritis, Osteoarthritis, ankylosing spondylitis, systemic lupus erythematosus, psoriasis, Hashimoto's disease, pancreatisis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myastehnia Gravis, uveitis, Guillain-Barre syndrome, psoriatic arthritis, Graves' disease, scleritis.

In a further aspect, the present invention provides a compound of formula (I), or a pharmaceutically acceptable salt thereof, for use in the treatment of asthma or chronic obstructive pulmonary disease.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

DETAILED DESCRIPTION OF THE INVENTION

In a first aspect, the present invention is directed to a compound of formula (I), or a pharmaceutically acceptable salt thereof:

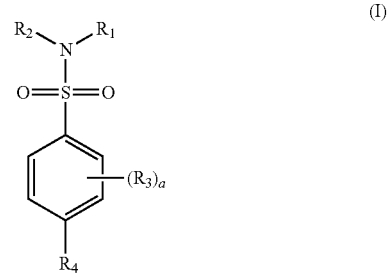

wherein:
R₁ is

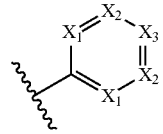

each $X_1$ is independently N or $CR_a$;
each $X_2$ is independently N or $CR_b$;
$X_3$ is N or CRC;
each $R_a$ is independently selected from H, $CF_3$, halo, $C_{1-4}$alkyl and $C_{1-4}$alkoxy;
each $R_b$ is independently selected from H, $CF_3$, halo, $CH_3$ and $OCH_3$;
each $R_c$ is independently selected from H, $C_{1-4}$alkyl, $C_{2-4}$alkenyl, $C_{1-4}$alkoxy, $CF_3$, halo, CN, $C_{3-6}$cycloalkyl and $C_{3-6}$heterocycloalkyl;

$R_2$ is selected from the group consisting of $C_{3-5}$alkyl, —$CH_2C_{3-4}$cycloalkyl, and —$CH_2$oxetanyl; each $R_3$ is independently selected from the group consisting of $C_{1-3}$alkyl, $C_{1-3}$alkoxy, halo, OH and $CH_2OH$;

$R_4$ is the group —$X(CHR_5)_bR_6$;

X is selected from the group consisting of O, $CH_2$, CHOH and $CHCH_2OH$;

each $R_5$ is independently selected from the group consisting of H, OH and $CH_2OH$;

$R_6$ is isoxazole, morpholine, piperidine, pyrrolidine, tetrahydro-2H-pyran, tetrahydrofuran, —$NHR_7$ or is a 5- or 6-membered heteroaryl group, wherein $R_6$ may be unsubstituted or substituted with one or two substitutents independently selected from halo and $CH_3$;

$R_7$ is oxetanyl or tetrahydrofuran, wherein $R_7$ may be unsubstituted or substituted with one or two substitutents independently selected from halo and $CH_3$;

a is 0, 1 or 2;

b is 0, 1 or 2;

with the proviso that $R_1$ contains one or two nitrogen atoms.

In a further aspect of the present invention, $R_1$ is selected from the group consisting of:

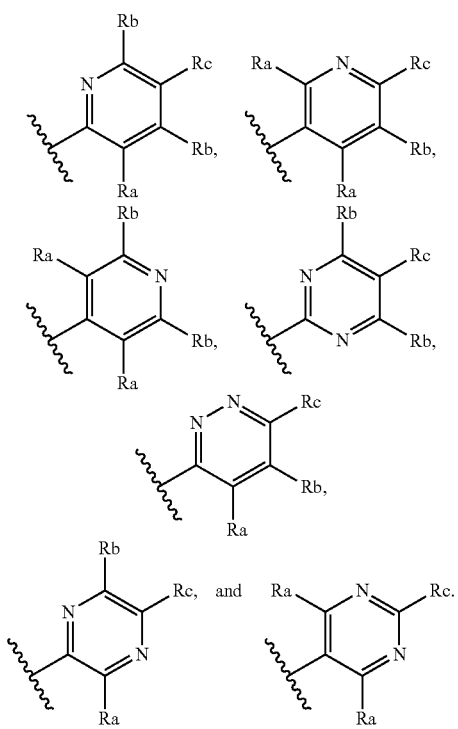

In a further aspect of the present invention, $R_1$ is selected from the group consisting of:

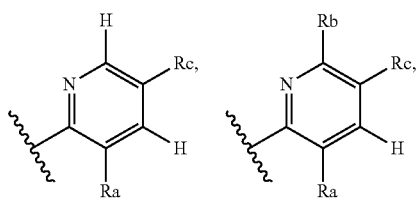

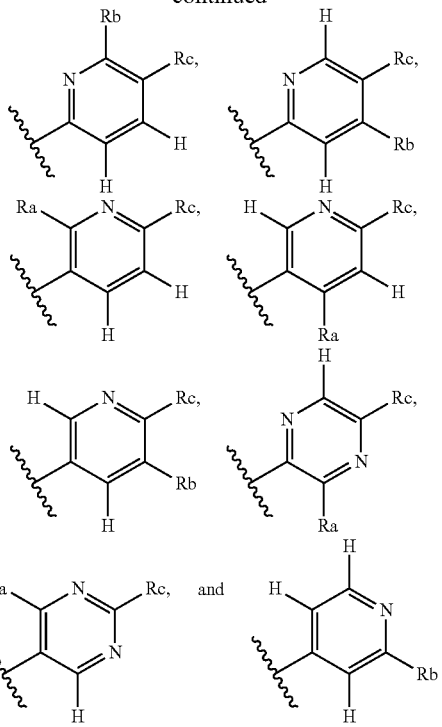

In a further aspect of the present invention, each Ra represents H.

In a further aspect of the present invention, each Ra is independently selected from $CH_3$, —$CH_2CH_3$, —$OCH_3$, —$OCH_2CH_3$ and halo.

In a further aspect of the present invention, each Ra is $CH_3$.

In a further aspect of the present invention, each Rb represents H.

In a further aspect of the present invention, each Rb is independently selected from $CH_3$, —$OCH_3$ and halo.

In a further aspect of the present invention, Rc represents H.

In a further aspect of the present invention, Rc represents $C_{1-4}$alkyl.

In a further aspect of the present invention, Rc represents isopropyl.

In a further aspect of the present invention, $R_2$ is selected from the group consisting of isopropyl, isobutyl, isopentyl and 3-methylbutan-2-yl.

In a further aspect of the present invention, $R_2$ is isobutyl.

In a further aspect of the present invention, X is O.

In a further aspect of the present invention, b is 1.

In a further aspect of the present invention, b is 2.

In a further aspect of the present invention, $R_5$ is H.

In a further aspect of the present invention, $R_6$ is isoxazole, morpholine, piperidine, pyrrolidine, tetrahydro-2H-pyran, or tetrahydrofuran, and further wherein $R_6$ may be unsubstituted or substituted with one or two substitutents independently selected from halo and $CH_3$.

In a further aspect of the present invention, $R_6$ is isoxazole or tetrahydro-2H-pyran, and further wherein $R_6$ may be unsubstituted or substituted with one or two substitutents independently selected from halo and $CH_3$.

In a further aspect of the present invention, $R_6$ is —$NHR_7$.

In a further aspect of the present invention, $R_7$ is unsubstituted oxetanyl.

In a further aspect of the present invention, $R_6$ is a 5- or 6-membered heteroaryl group, wherein $R_6$ may be unsubstituted or substituted with one or two substitutents independently selected from halo and $CH_3$.

In a further aspect of the present invention, $R_6$ is unsubstituted.

In a further aspect of the present invention, $R_6$ is 3,5-dimethylisoxazole, of formula:

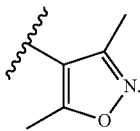 [SMILES: *c1c(C)noc1C]

In a further aspect of the present invention, a is 0.
In a further aspect of the present invention, a is 1.
In a further aspect of the present invention, $R_3$ is selected from the group consisting of $CH_3$, —$OCH_3$, halo, OH and $CH_2OH$.

It is understood that the present invention covers all combinations of substituent groups referred to herein above.

Specific examples of compounds of formula (I) are:
4-((3,5-dimethylisoxazol-4-yl)methoxy)-N-(4,6-dimethylpyrimidin-2-yl)-N-isobutylbenzenesulfonamide;
4-((3,5-dimethylisoxazol-4-yl)methoxy)-N-isobutyl-N-(5-isopropylpyridin-2-yl)benzenesulfonamide;
4-((3,5-dimethylisoxazol-4-yl)methoxy)-N-isobutyl-N-(5-methylpyridin-2-yl)benzenesulfonamide;
4-((3,5-dimethylisoxazol-4-yl)methoxy)-N-isobutyl-N-(4-methylpyridin-2-yl)benzenesulfonamide;
4-((3,5-dimethylisoxazol-4-yl)methoxy)-N-isobutyl-N-(6-methylpyridin-2-yl)benzenesulfonamide;
4-((3,5-dimethylisoxazol-4-yl)methoxy)-N-isobutyl-N-(3-methylpyridin-2-yl)benzenesulfonamide;
N-(5-chloropyridin-2-yl)-4-((3,5-dimethylisoxazol-4-yl)methoxy)-N-isobutylbenzenesulfonamide;
4-((3,5-dimethylisoxazol-4-yl)methoxy)-N-(5-fluoropyridin-2-yl)-N-isobutylbenzenesulfonamide;
4-((3,5-dimethylisoxazol-4-yl)methoxy)-N-(2,6-dimethylpyridin-3-yl)-N-isobutylbenzenesulfonamide;
4-((3,5-dimethylisoxazol-4-yl)methoxy)-N-isobutyl-N-(6-methylpyridin-3-yl)benzenesulfonamide;
4-((3,5-dimethylisoxazol-4-yl)methoxy)-N-isobutyl-N-(4-methylpyridin-3-yl)benzenesulfonamide;
4-((3,5-dimethylisoxazol-4-yl)methoxy)-N-(3,5-dimethylpyrazin-2-yl)-N-isobutylbenzenesulfonamide;
4-((3,5-dimethylisoxazol-4-yl)methoxy)-N-isobutyl-N-(2-methylpyridin-4-yl)benzenesulfonamide;
4-{[(3,5-dimethyl-4-isoxazolyl)methyl]oxy}-N-(2-methylpropyl)-N-[4-(trifluoromethyl)-2-pyrimidinyl]benzenesulfonamide;
4-{[(3,5-dimethyl-4-isoxazolyl)methyl]oxy}-N-(3,5-dimethyl-2-pyridinyl)-N-(2-methylpropyl)benzenesulfonamide;
4-{[(3,5-dimethyl-4-isoxazolyl)methyl]oxy}-N-[2-methyl-6-(2-oxo-1,3-oxazolidin-3-yl)-3-pyridinyl]-N-(2-methylpropyl)benzenesulfonamide;
4-{[(3,5-dimethyl-4-isoxazolyl)methyl]oxy}-N-[2-methyl-6-(4-morpholinyl)-3-pyridinyl]-N-(2-methylpropyl)benzenesulfonamide;
2-chloro-N-(3,5-dimethylpyridin-2-yl)-N-isobutyl-4-((tetrahydro-2H-pyran-4-yl)methoxy)benzenesulfonamide;
4-((3,5-dimethylisoxazol-4-yl)methoxy)-N-isobutyl-N-(6-methoxypyridazin-3-yl)benzenesulfonamide;
4-((3,5-dimethylisoxazol-4-yl)methoxy)-N-(6-ethoxypyridazin-3-yl)-N-isobutylbenzenesulfonamide;
4-((3,5-dimethylisoxazol-4-yl)methoxy)-N-(5-ethylpyrimidin-2-yl)-N-isobutylbenzenesulfonamide;
4-((3,5-dimethylisoxazol-4-yl)methoxy)-N-isobutyl-N-(5-methylpyridin-2-yl)benzenesulfonamide;
N-(3,5-dimethylpyridin-2-yl)-N-isobutyl-4-((tetrahydro-2H-pyran-4-yl)methoxy)benzenesulfonamide;
4-((3,5-dimethylisoxazol-4-yl)methoxy)-N-(3-ethyl-6-methylpyridin-2-yl)-N-isobutylbenzenesulfonamide; isobutylbenzenesulfonamide;
4-{[(3,5-dimethyl-4-isoxazolyl)methyl]oxy}-N-[6-(methyloxy)-2-pyridinyl]-N-(2-methylpropyl)benzenesulfonamide;
N-isobutyl-N-(6-methoxypyridin-2-yl)-4-(pyridin-4-ylmethoxy)benzenesulfonamide;
4-{[(3,5-dimethyl-4-isoxazolyl)methyl]oxy}-N-(4,6-dimethyl-3-pyridinyl)-N-(2-methylpropyl)benzenesulfonamide;
4-((3,5-dimethylisoxazol-4-yl)methoxy)-N-(3,6-dimethylpyrazin-2-yl)-N-isobutylbenzenesulfonamide;
4-((3,5-dimethylisoxazol-4-yl)methoxy)-N-isobutyl-N-(4-methylpyrimidin-5-yl)benzenesulfonamide;
4-((3,5-dimethylisoxazol-4-yl)methoxy)-N-isobutyl-N-(2-methyl-6-(pyrrolidin-3-yl)pyridin-3-yl)benzenesulfonamide;
N-isobutyl-N-(5-isopropyl-3-methylpyridin-2-yl)-4-((tetrahydro-2H-pyran-4-yl)methoxy)benzenesulfonamide;
N-isobutyl-N-(3-methyl-5-(prop-1-en-2-yl)pyridin-2-yl)-4-((tetrahydro-2H-pyran-4-yl)methoxy)benzenesulfonamide;
N-isobutyl-N-(5-isopropylpyridin-2-yl)-4-((tetrahydro-2H-pyran-4-yl)methoxy)benzenesulfonamide;
N-(5-chloro-3-methylpyridin-2-yl)-N-isobutyl-4-((tetrahydro-2H-pyran-4-yl)methoxy)benzenesulfonamide;
4-((cis-3-fluoropiperidin-4-yl)methoxy)-N-isobutyl-N-(5-isopropyl-3-methylpyridin-2-yl)benzenesulfonamide;
4-((cis-3-fluoropiperidin-4-yl)methoxy)-N-isobutyl-N-(5-isopropylpyridin-2-yl)benzenesulfonamide;
4-((3,5-dimethylisoxazol-4-yl)methoxy)-N-isopentyl-N-(5-isopropylpyridin-2-yl)benzenesulfonamide;
N-(5-isopropylpyridin-2-yl)-N-(3-methylbutan-2-yl)-4-((tetrahydro-2H-pyran-4-yl)methoxy)benzenesulfonamide;
N-isobutyl-N-(5-isopropyl-3-methoxypyridin-2-yl)-4-((tetrahydro-2H-pyran-4-yl)methoxy)benzenesulfonamide;
N-(2-cyclopropylpyrimidin-5-yl)-4-((3,5-dimethylisoxazol-4-yl)methoxy)-N-isobutylbenzenesulfonamide;
N-(5-isopropylpyridin-2-yl)-N-(oxetan-3-ylmethyl)-4-((tetrahydro-2H-pyran-4-yl)methoxy)benzenesulfonamide;
4-{[(3,5-dimethyl-4-isoxazolyl)methyl]oxy}-N-(2-methylpropyl)-N-[2-(trifluoromethyl)-4-pyrimidinyl]benzenesulfonamide;
4-((3,5-dimethylisoxazol-4-yl)methoxy)-N-isobutyl-N-(pyrazin-2-yl)benzenesulfonamide;
4-((3,5-dimethylisoxazol-4-yl)methoxy)-N-isobutyl-N-(pyrimidin-5-yl)benzenesulfonamide;
4-((3,5-dimethylisoxazol-4-yl)methoxy)-N-isobutyl-N-(2-methylpyrimidin-5-yl)benzenesulfonamide;
4-((3,5-dimethylisoxazol-4-yl)methoxy)-N-isobutyl-N-(5-methylpyridin-3-yl)benzenesulfonamide;
N-(cyclobutylmethyl)-4-((3,5-dimethylisoxazol-4-yl)methoxy)-N-(5-isopropylpyridin-2-yl)benzenesulfonamide;
N-(6-cyclopropylpyridazin-3-yl)-4-((3,5-dimethylisoxazol-4-yl)methoxy)-N-isobutylbenzenesulfonamide;
4-((3,5-dimethylisoxazol-4-yl)methoxy)-N-(5-isopropylpyridin-2-yl)-N-(2-methylbutyl)benzenesulfonamide;

4-(1-hydroxy-2-morpholinoethyl)-N-isobutyl-N-(5-isopropylpyridin-2-yl)benzenesulfonamide; and 4-(1-hydroxy-2-((3-methyloxetan-3-yl)amino)ethyl)-N-isobutyl-N-(5-isopropylpyridin-2-yl)benzenesulfonamide.

As used herein, the term "alkyl" refers to a saturated hydrocarbon chain having the specified number of member atoms. For example, $C_{1-4}$ alkyl refers to an alkyl group having from 1 to 4 member atoms. Unless otherwise stated, alkyl groups are unsubstituted. Alkyl groups may be straight chain or branched. The term "alkyl" includes, but is not limited to, methyl, ethyl, propyl (n-propyl and isopropyl), butyl (n-butyl, sec-butyl, isobutyl and tert-butyl).

As used herein, the term "alkenyl" refers to an unsaturated hydrocarbon chain having the specified number of member atoms and having one or more carbon-carbon double bond within the chain, such as one or two. For example, $C_{2-4}$ alkenyl refers to an alkenyl group having from 2 to 4 member atoms. Alkenyl groups may be straight or branched, and are unsubstituted unless otherwise stated.

As used herein, the term "alkoxy" refers to an —O-alkyl group wherein "alkyl" is defined above.

As used herein, the term "heterocycloalkyl" refers to a saturated or unsaturated monocyclic ring having the specified number of member atoms. Heterocycloalkyl groups must contain 1, 2 or 3 non-carbon atoms, which are selected from nitrogen, oxygen, and sulfur. Heterocycloalkyl groups may contain one or more C(O), S(O) or $SO_2$ groups. However, heterocycloalkyl groups are not aromatic. Heterocycloalkyl groups containing more than one heteroatom may contain different heteroatoms. Heterocycloalkyl includes, but is not limited to, pyrrolidine, piperidine, oxetane, tetrahydrofuran, tetrahydro-2H-pyran, morpholine, morpholine-3-one, piperidin-2-one, pyrimidine-2,4(1H, 3H)-dione, thiomorpholine, thiomorpholine 1,1-dioxide.

As used herein, the term "cycloalkyl" refers to a saturated hydrocarbon ring having the specified number of member atoms. Cycloalkyl groups are monocyclic ring systems. For example, $C_{3-6}$ cycloalkyl refers to a cycloalkyl group having from 3 to 6 member atoms. Cycloalkyl includes cyclopropyl, cyclobutyl, cyclopentyl and cyclohexyl.

As used herein, the term "halo" refers to the halogen radicals fluoro, chloro, bromo and iodo.

As used herein, the phrase "5- or 6-membered heteroaryl" indicates an aromatic ring containing 5 or 6 member atoms, wherein the member atoms are either carbon or nitrogen. The 5- or 6-membered heteroaryl group may contain one, two, three or four nitrogen atoms as member atoms of the ring.

As used herein, the term "RORγ" refers to all isoforms of this member of the ROR family, including RORγ1 and RORγt.

As used herein, the term "RORγ modulator" refers to a chemical compound of formula (I) that inhibits, either directly or indirectly, the activity of RORγ. RORγ modulators include antagonists and inverse agonists of RORγ.

The compounds of formula (I) and pharmaceutically acceptable salts thereof may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of formula (I), or in any chemical structure illustrated herein, is not specified the structure is intended to encompass all individual stereoisomers and all mixtures thereof. Thus, compounds of formula (I) and pharmaceutically acceptable salts thereof containing one or more chiral center may be used as racemic mixtures, enantiomerically enriched mixtures, or as enantiomerically pure individual stereoisomers.

Individual stereoisomers of a compound of formula (I), or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

In certain aspects, compounds of formula (I) may contain an acidic functional group. In certain other embodiments, compounds of formula (I) may contain a basic functional group. Thus, the skilled artisan will appreciate that pharmaceutically-acceptable salts of the compounds of formula (I) may be prepared. Indeed, in certain embodiments of the invention, pharmaceutically-acceptable salts of the compounds of formula (I) may be preferred over the respective free base or free acid because such salts may impart greater stability or solubility to the molecule thereby facilitating formulation into a dosage form.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopaedia of Pharmaceutical Technology, Marcel Dekker Inc, New York 1996, Volume 13, page 453-497. Other salts that are not deemed pharmaceutically acceptable may be useful in the preparation of compounds of formula (I) and are included within the scope of the invention, such as ammonia and trifluoroacetic acid. The present invention encompasses all possible stoichiometric and non-stoichiometric forms of the salts of the compounds of formula (I).

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

The invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2H$, $^3H$, $^{13}C$, $^{14}C$, $^{15}N$, $^{17}O$, $^{18}O$, $^{18}F$ and $^{36}Cl$, respectively. Certain isotopic variations of a compound of formula (I) or a salt or solvate thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

A compound of formula (I), or a pharmaceutically acceptable salt thereof, may be in amorphous or crystalline form. Moreover, a compound of formula (I), or a pharmaceutically acceptable salt thereof, may exist in one or more crystalline forms. Consequently, the present invention includes within its scope all forms of a compound of formula (I), or a pharmaceutically acceptable salt thereof.

The person skilled in the art will appreciate that many organic compounds can form complexes with solvents in which they are reacted or from which they are precipitated or crystallised. These complexes are known as "solvates". Where the solvent is water the complex is known as a "hydrate". The present invention encompasses all solvates of the compounds of formula (I).

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

EXPERIMENTAL

Compounds of the invention may be prepared by methods known in the art of organic synthesis as set forth in part by the following synthesis schemes. In the following reaction schemes and hereafter, unless otherwise stated, all the groups are defined in the first aspect. It is also recognised that in all of the schemes described below, it is well understood that protecting groups for sensitive or reactive groups are employed where necessary in accordance with general principles of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the invention.

General Reaction Schemes

Experimental

Compounds of formula (I) may be prepared by methods known in the art of organic synthesis as set forth in part by the following synthesis schemes. In the following reaction schemes and hereafter, unless otherwise stated, all the groups are defined in the first aspect. It is also recognised that in all of the schemes described below, it is well understood that protecting groups for sensitive or reactive groups are employed where necessary in accordance with general principles of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as General Reaction Schemes Scheme 1

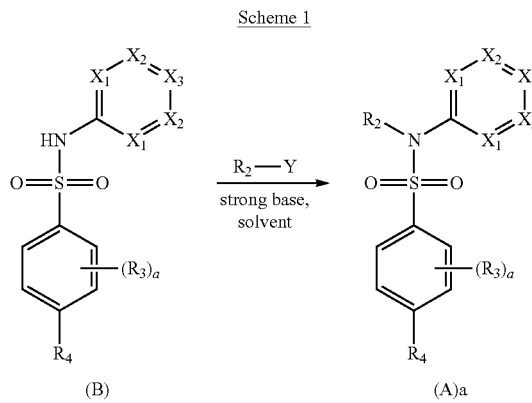

Y = suitable leaving group eg. Br, I, Cl, OTs

Compounds of formula (A)a, may be prepared from intermediate compounds of formula (B), by reaction with a suitable alkylating agent according to Scheme 1. Typical reaction conditions comprise mixing together a compound of formula (B), with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Scheme 2

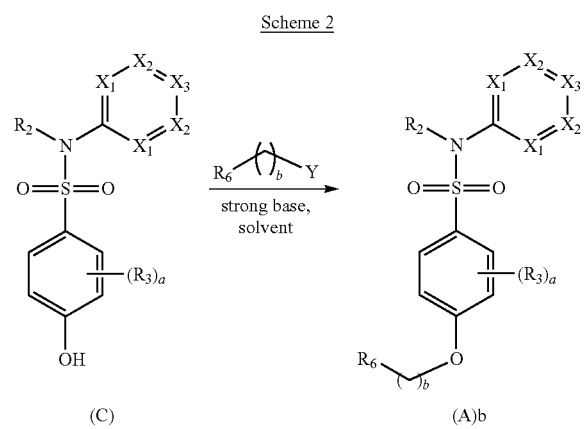

Y = suitable leaving group eg. Br, I, Cl, F, OTs
b = 1, 2

Compounds of formula (A)$_b$ may be prepared from intermediate compounds of formula (C), by reaction with an appropriate alkylating agent according to Scheme 2. Typical reaction conditions comprise mixing an intermediate compound of formula (C), with a strong base such as sodium hydride in a suitable solvent, such as dimethylsulfoxide, for a suitable time, such as 5 minutes, under nitrogen. The mixture is then treated with the alkylating agent and stirred at a suitable temperature such as ambient for a suitable time, such as 18 hours.

Scheme 3

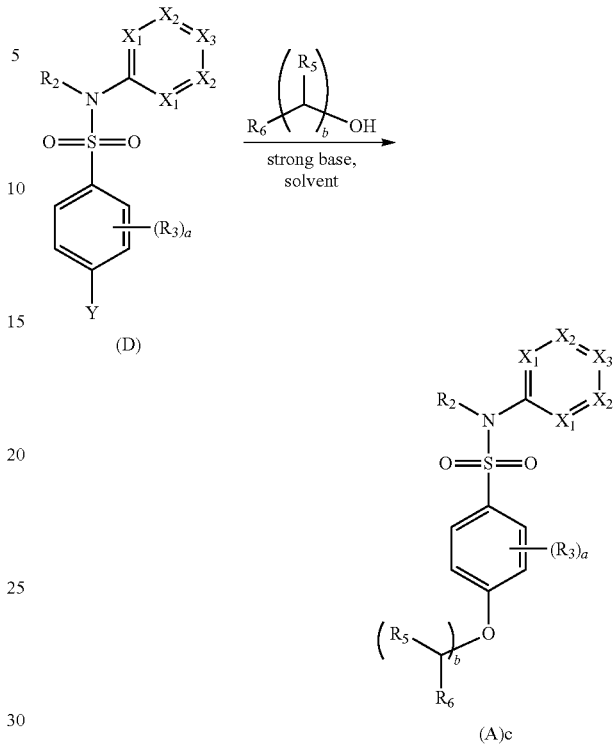

Y = suitable leaving group eg. Br, I, Cl, F, OTs
b = 0, 1, 2

Compounds of formula (A)c may be prepared from intermediate compounds of formula (D), by reaction with an appropriately substituted alkyl alcohol according to Scheme 3. Typical reaction conditions comprise mixing the alcohol together with an intermediate compound of formula (D), with a strong base such as sodium hydride, in a suitable solvent such as 2-methyltetrahydrofuran, under nitrogen at a suitable temperature, such as ambient for a suitable time, such as 3 hours.

Scheme 4

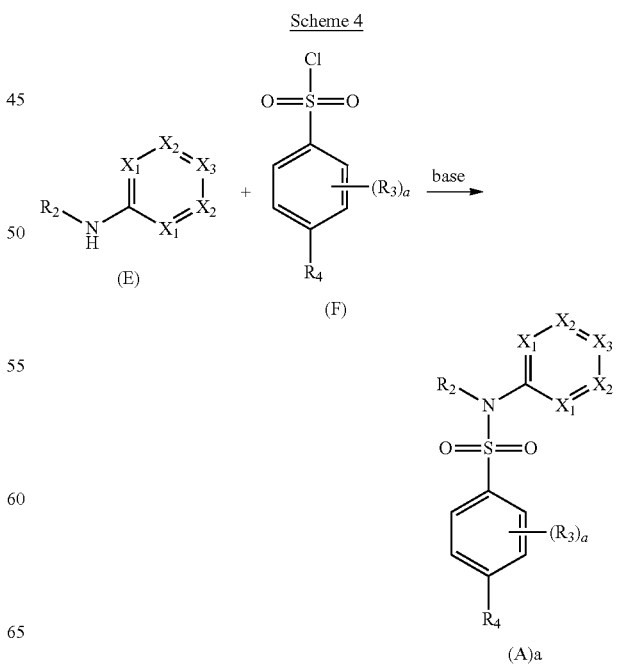

Compounds of formula (A)a may be prepared from sulfonyl chlorides of formula (F), by reaction with a heteroaryl-amine of formula (E), according to Scheme 4. Typical reaction conditions comprise mixing together a sulfonyl chloride of formula (F) with the appropriate heteroaryl-amine (E), in a basic solvent such as pyridine, for a suitable time, such as 16 hours, at a suitable temperature, such as ambient.

Scheme 5

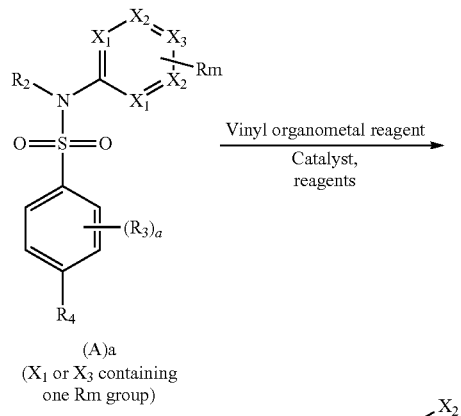

(A)a
($X_1$ or $X_3$ containing one Rm group)

Rm = suitable cross-coupling group, eg. halogen, OTf
R′, R″ = H or $C_{1-2}$ alkyl Vinyl containing compounds of formula (A)d, may be prepared from compounds of formula (A)a, by reaction with a vinyl organometal reagent, according to Scheme 5. Typical reaction conditions comprise mixing together compound (A)a with a suitable vinyl organometal reagent, such as potassium trifluoro(prop-1-en-2-yl)borate and a suitable catalyst such as Buchwald's Suzuki-Miyaura cross coupling pre-catalyst (J. Am. Chem. Soc. 2010, 132, 14073) in a suitable solvent, such as tetrahydrofuran. An appropriate base such as aqueous potassium phosphate is then added and the reaction heated in a sealed vessel to a suitable temperature, for example 110° C., by microwaves, for a suitable time, such as 30 minutes.

Scheme 6

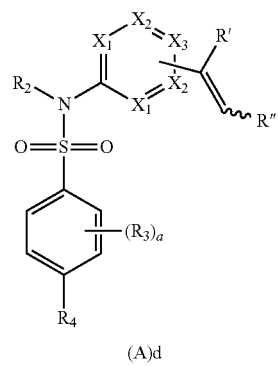

(A)d

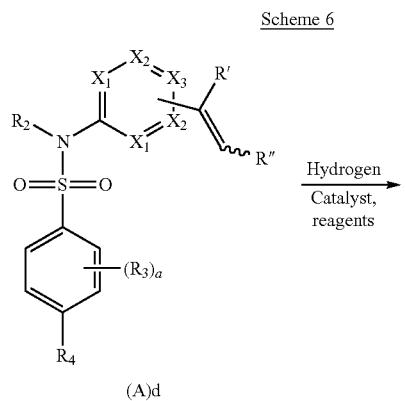

(A)d

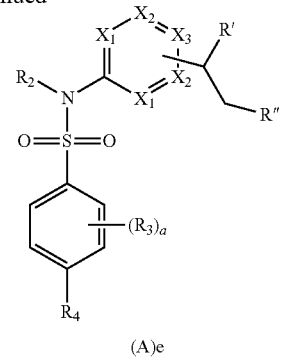

(A)e

R′, R″ = H or $C_{1-2}$ alkyl

Compounds of formula (A)e may be prepared from compounds of formula (A)d by reduction of the double bond, according to Scheme 6. Typical reaction conditions comprise dissolving a compound of formula (A)d in a suitable solvent system, such as methanol/ethyl-acetate and passing the mixture through a flow hydrogenator fitted with a suitable catalyst cartridge, such as 10% Pd/C and using suitable flow reaction conditions, such as room temperature, 1 bar hydrogen pressure and 1 mL/min flow rate.

Scheme 7

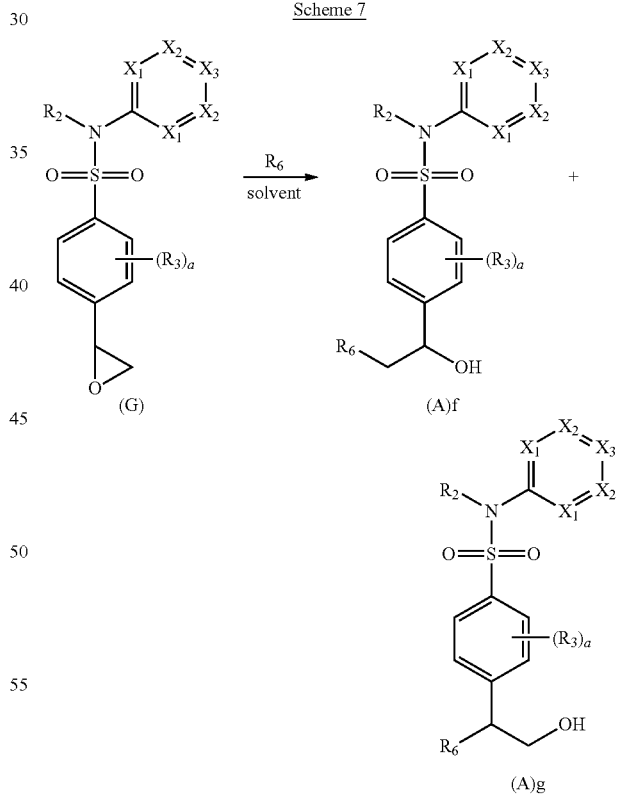

Where $R_6$ = heterocycloalkyl with free NH in ring system
or $R_6 = R_7NH_2$

Compounds of formula (A)f and (A)g may be prepared from epoxide-containing intermediate compounds of formula (G), by reaction with either an appropriate alkyl or heterocycloalkyl amine, according to Scheme 7. Typical reaction conditions comprise mixing together epoxide-containing intermediate compound (G) with an excess of the appropriate amine, in a suitable solvent, such as ethanol, at a suitable temperature, such as 50° C., for a suitable time, such as overnight. The ratio of products (A)f to (A)g may vary with selection of amine, and where a mixture of products results, separation may be achieved using a suitable purification system, such as preparative HPLC.

Scheme 8

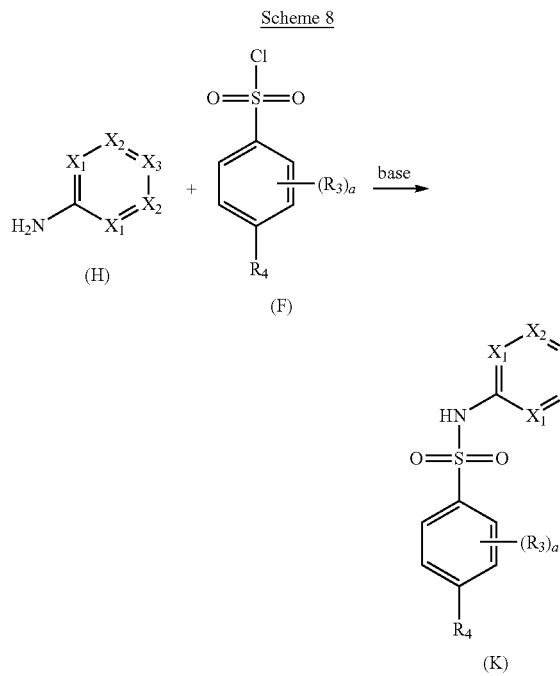

Secondary sulfonamide compounds of formula (K) may be prepared from sulfonyl chlorides of formula (F), by reaction with a primary heteroaryl-amine of formula (H), according to Scheme 8. Typical reaction conditions comprise mixing together a sulfonyl chloride of formula (F) with the appropriate heteroaryl-amine (H), in a basic solvent such as pyridine, for a suitable time, such as 16 hours, at a suitable temperature such as ambient, or with heating applied if necessary.

Scheme 9

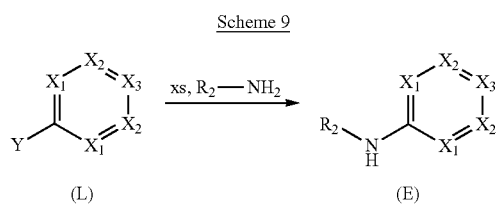

(L)
(One or both $X_1$ must be N)
Y = suitable leaving group eg. Br, I, Cl, F, OTs Intermediate compounds of formula (E) may be prepared from suitably substituted heteroaromatic compounds of formula (L) by reaction with a suitable primary alkyl amine, according to Scheme 9. Typical reaction conditions comprise mixing together a substituted heteroaromatic compound of formula (L) with an excess of primary alkyl amine and stirring the mixture at a suitable temperature, such as ambient, for a suitable time, such as 17 hours.

Scheme 10

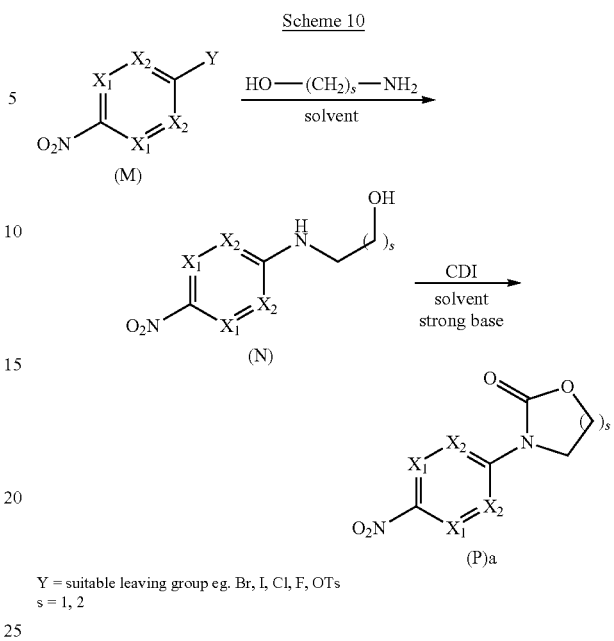

Y = suitable leaving group eg. Br, I, Cl, F, OTs
s = 1, 2

Intermediate compounds of formula (P)a may be prepared in two steps from substituted heteroaromatic compounds of formula (M), according to Scheme 10. Typical reaction conditions for the initial step, comprise mixing together a substituted heteroaromatic compound (M) with a suitable aminoalkylalcohol, in a suitable solvent, such as ethanol, for a suitable time, such as overnight, at a suitable temperature, such as ambient.

Once isolated, intermediates of formula (N) can then be transformed into compounds (P)a using a suitable coupling reagent and base. Typical reaction conditions for this step comprise mixing intermediate (N) with a suitable coupling reagent, such as 1,1'-carbonyldiimidazole (CDI), in a suitable solvent such as 2-methyltetrahydrofuran. The mixture is stirred for a suitable time, such as 4 hours, at a suitable temperature, such as ambient, then a suitable strong base, such as sodium hydride is added and the mixture stirred for a suitable additional time, such as 2 hours to complete the reaction.

Scheme 11

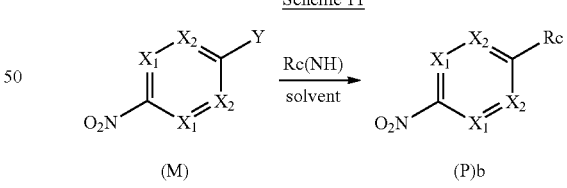

Y = suitable leaving group eg. Br, I, Cl, F, OTs
Rc(NH) = $C_{3-6}$ heterocycloalkyl with free NH in ring system Intermediate compounds of formula (P)$_b$ may be prepared from substituted heteroaromatic compounds of formula (M) by reaction with a suitable heterocycloalkyl compound containing a free NH group within the ring system, according to Scheme 11. Typical reaction conditions comprise mixing together a substituted heteroaromatic compound (M) with a suitable heterocycloalkyl compound containing a free NH group within the ring system, in a suitable solvent, such as ethanol, at a suitable temperature, such as 70° C., for a suitable time, such as 5 hours.

Scheme 12

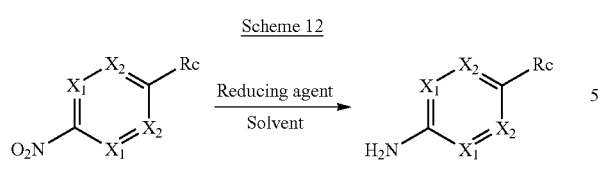

Intermediate compounds of formula (H) may be prepared from nitro-substituted heteroaromatic compounds of formula (P) by reduction of the nitro group according to Scheme 12. Typical reaction conditions comprise mixing the nitro-substituted heteroaromatic compound (P) with a suitable reducing agent, such as a 6:1 mixture of iron powder/ammonium chloride, in a suitable solvent system such as 3:1 ethanol/water and heating the mixture to a suitable temperature, such as reflux, for a suitable time, such as 2 hours.

Scheme 13

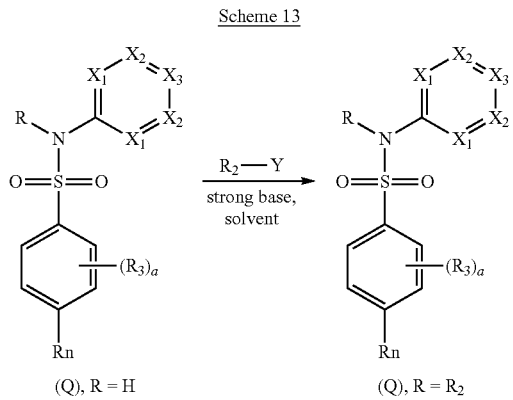

$R_n$ = -halo, —OMe/—OBn, —CH=CH$_2$
Y = suitable leaving group eg. Br, I, Cl, OTs Compounds of formula (Q) where R=R$_2$, may be prepared from intermediate compounds of formula (Q), where R=H, by reaction with a suitable alkylating agent according to Scheme 13. Typical reaction conditions comprise mixing together a compound of formula (Q), where R=H, with a strong base, such as Barton's base, in a suitable solvent such as acetonitrile, for a suitable time, such as 1 hour, at a suitable temperature such as ambient. The mixture is then treated with the appropriate alkylating agent and heated in a sealed vessel to a suitable temperature, for example 150° C., by microwaves, for a suitable time, such as 25 minutes.

Scheme 14

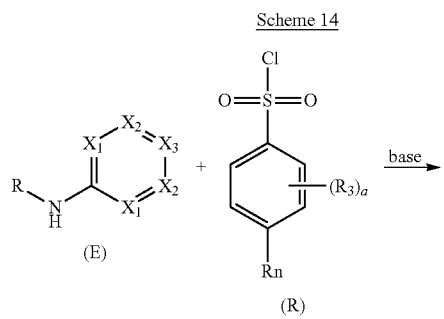

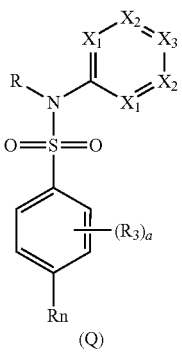

$R_n$ = -halo, —OMe/—OBn, —CH=CH$_2$
R = R$_2$ or H

Key intermediate compounds of formula (Q), where $R_n$ is a suitable functional group for later transformation into $R_6$; may be prepared from sulfonyl chlorides of formula (R), by reaction with a heteroaryl-amine of formula (E) according to Scheme 14. Typical reaction conditions comprise mixing together a sulfonyl chloride of formula (R) with the appropriate heteroaryl-amine (E) in a basic solvent such as pyridine, for a suitable time, such as 16 hours, at a suitable temperature such as ambient, or with heating applied if necessary.

$R_n$ may include functionality (which can be protected/masked) that is inert to reaction under the above conditions and may then be converted to $R_6$ in subsequent step(s). Suitable examples for $R_n$ can include -halo, —OMe/—OBn and —CH=CH$_2$.

Scheme 15

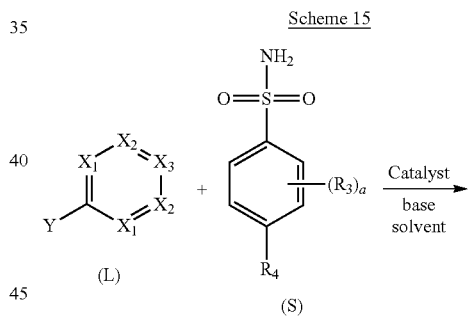

Y = suitable leaving group eg. Br, I, Cl, OTf

Intermediate compounds of formula (K) may be prepared from sulphonamides of formula (S), by reaction with a substituted heteroaryl compound of formula (L), according to Scheme 15. Typical reaction conditions comprise mixing a substituted heteroaryl compound (L), with a sulphonamide of formula (S), a suitable catalyst such as palladium(II) acetate, a suitable ligand such as Xantphos and a suitable base, such as cesium carbonate, in a suitable solvent, such as 1,4-dioxane. The mixture is then heated in a sealed vessel to a suitable temperature, for example 130° C., by microwaves, for a suitable time, such as 30 minutes.

Scheme 16

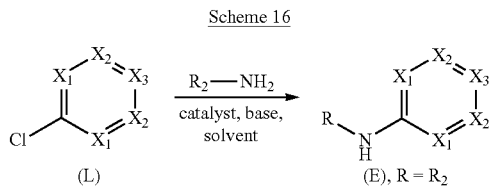

Where $X_1$-$X_5$ should not contain substituents which are reactive towards palladium cross-coupling Secondary anilines of formula (E), R=$R_2$ may be prepared from heteroaryl chlorides of formula (L), by reaction with an appropriate primary alkylamine according to Scheme 16. Typical reaction conditions comprise mixing together a heteroaryl chloride (L), with the appropriate primary alkyl amine, a suitable catalyst such as {1,3-bis[2,6-bis(1-methylethyl)phenyl]-2-imidazolidinyl}(chloro)(2-methyl-2-propen-1-yl)palladium and a suitable base such as lithium hexamethyldisilizide, in a suitable solvent, such as tetrahydrofuran. The mixture is then heated in a sealed vessel to a suitable temperature, for example 70° C., by microwaves, for a suitable time, such as 45 minutes.

Scheme 17

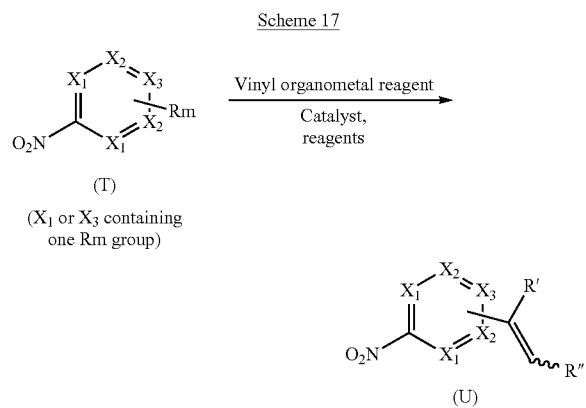

Rm = suitable cross-coupling group, eg. halogen, OTf
R', R" = H or $C_{1-2}$ alkyl Intermediate compounds of formula (U) may be prepared from substituted heteroaromatic compounds of formula (T), by reaction with a suitable vinyl organometal reagent, according to Scheme 17. Typical reaction conditions comprise mixing a substituted heteroaromatic compound of formula (T) with a suitable vinyl organometal reagent, such as 2-ethenyl-4,4,5,5-tetramethyl-1,3,2-dioxaborolane, a suitable catalyst such as palladium(II) acetate, a suitable ligand, such as X-phos and an appropriate base such as cesium carbonate. A suitable solvent, such as 2-methyltetrahydrofuran/water mixture is then added and the reaction heated to a suitable temperature, such as 60° C., for a suitable time, such as 1 hour.

Scheme 18

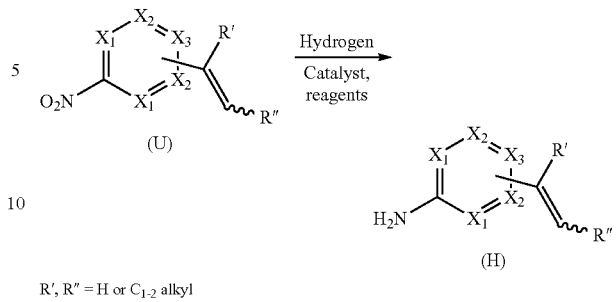

R', R" = H or $C_{1-2}$ alkyl

Compounds of formula (H) may be prepared from compounds of formula (U) by reduction of the double bond and nitro groups, according to Scheme 18. Typical reaction conditions comprise dissolving a compound of formula (U) in a suitable solvent, such as ethanol and passing the mixture through a flow hydrogenator fitted with a suitable catalyst cartridge, such as 10% Pd/C and using suitable flow reaction conditions, such as room temperature, 1 bar hydrogen pressure and 1 mL/min flow rate.

Scheme 19

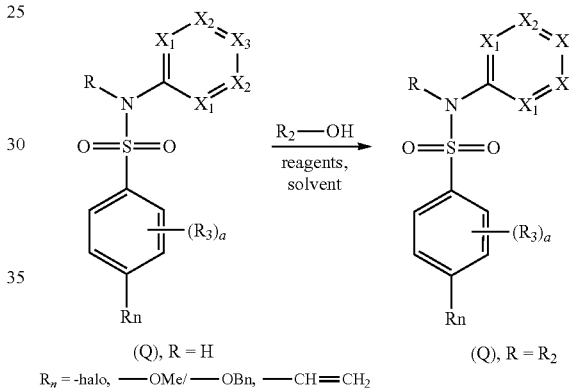

$R_n$ = -halo, —OMe/ —OBn, —CH=$CH_2$

Compounds of formula (Q), R=$R_2$, may be prepared from compounds of formula (Q), R=H, by coupling with a suitable alkyl alcohol, according to Scheme 19. Typical reaction conditions comprise mixing together a compound of formula (Q), R=H, with a suitable alkyl alcohol, in a suitable solvent, such as toluene and adding a suitable coupling reagent, such as 2-(tributylphosphoranylidene)acetonitrile. The mixture is then heated in a sealed vessel to a suitable temperature, for example 150° C., by microwaves, for a suitable time, such as 30 minutes.

Scheme 20

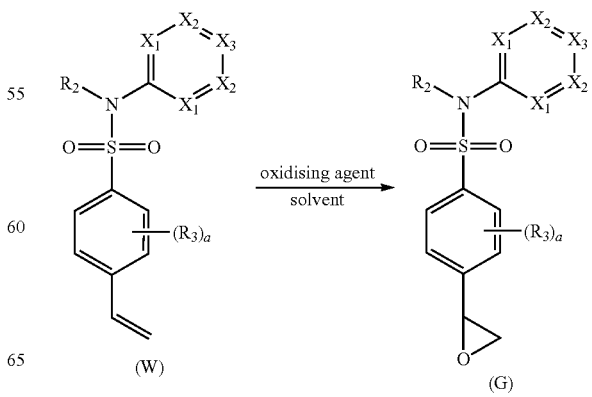

Epoxide-containing intermediate compounds of formula (G), may be prepared from intermediate compounds of formula (W), by oxidation of the double bond, according to Scheme 20. Typical reaction conditions comprise mixing together intermediate compound (W) with a suitable oxidising agent, such as m-chloroperbenzoic acid in an appropriate solvent such as dichloromethane, for a suitable time, such as 16 hours, at a suitable temperature, such as 0° C. to ambient.

Scheme 21

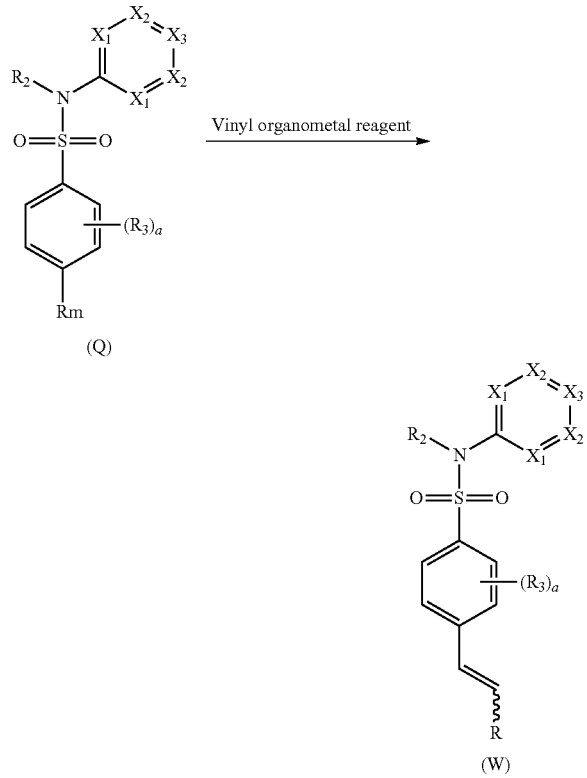

Rm = suitable cross-coupling group, eg. halogen, OTf
R = H, alkyl or substituted alkyl Vinyl containing intermediate compounds of formula (W), may be prepared from intermediate compounds of formula (Q), by reaction with a vinyl organometal reagent, according to Scheme 21. Typical reaction conditions comprise mixing together intermediate compound (Q) with a suitable vinyl organometal reagent, such as potassium trifluoro(vinyl)borate, an appropriate base such as cesium carbonate and a suitable catalyst such as palladium(II)chloride with a suitable ligand, such as triphenylphosphine. A suitable solvent, such as tetrahydrofuran/water mixture is then added and the reaction heated in a sealed vessel to a suitable temperature, for example 140° C., by microwaves, for a suitable time, such as 1 hour.

Example RORγ Modulators

The present invention is further illustrated by the following non-limiting examples of RORγ modulators, which have been prepared by a number of different methods.

Intermediate Preparation

Intermediate 1

N-(2-methylpropyl)-4-(trifluoromethyl)-2-pyrimidinamine

A mixture of 2-chloro-4-(trifluoromethyl)pyrimidine (548 mg, 3 mmol) in isobutylamine (1.5 mL) was stirred at room temperature for 17 hours. To the mixture was added water (5 mL) and dichloromethane (5 mL). The organic layer was separated and purified by flash silica (Si) chromatography (0-100% dichloromethane-cyclohexane gradient) to give the title compound (455 mg) as a colourless oil. LCMS (2 min, formic) Rt 1.20 min, m/z (ES$^+$) 220 (M+H).

Intermediate 2

4-hydroxy-N-(2-methylpropyl)-N-[4-(trifluoromethyl)-2-pyrimidinyl]benzenesulfonamide To a solution of N-(2-methylpropyl)-4-(trifluoromethyl)-2-pyrimidinamine (50 mg, 0.228 mmol) in N,N-dimethylformamide (0.5 mL), stirred under nitrogen at room temperature, was added sodium hydride (60% wt in mineral oil) (9.12 mg, 0.228 mmol). The reaction mixture was stirred at 20° C. for 5 min, then a solution of 4-{[(3,5-dimethyl-4-isoxazolyl)methyl]oxy}benzenesulfonyl chloride (68.8 mg, 0.228 mmol) in N,N-dimethylformamide (0.5 mL) was added dropwise over 1 min. The reaction mixture was stirred at 20° C. for 16 hours. The reaction was carefully quenched with water (1 mL) and extracted with dichloromethane (2×1 mL), then the organics separated by hydrophobic frit. The solvent was removed in vacuo and the crude material purified by flash silica (Si) (0-15% methanol-dichloromethane gradient). Analysis confirmed cleavage of the (3,5-dimethyl-4-isoxazolyl)methyl group had occurred to provide the unsubstituted phenol product (31 mg). LCMS (2 min, formic) Rt 1.17 min, m/z (ES$^+$) 376 (M+H).

Intermediate 3

3-(6-methyl-5-nitro-2-pyridinyl)-1,3-oxazolidin-2-one

To a solution of 2-((6-methyl-5-nitropyridin-2-yl)amino)ethanol (223 mg, 1.131 mmol) in 2-methyltetrahydrofuran (20 mL) was added 1,1'-carbonyldiimidazole (CDI) (220 mg, 1.357 mmol) and the reaction mixture stirred under nitrogen for 4 hours. The mixture was then left to stand for 20 hours. To this was added sodium hydride (60% wt in mineral oil) (100 mg, 2.488 mmol) and the reaction mixture stirred at room temperature for 2 hours. The reaction mixture was then diluted with water and ethyl acetate and the organic phase separated, washed with brine, then dried over magnesium sulphate. The solvent was removed in vacuo and the residue purified by flash silica (Si) chromatography (0-100% ethyl acetate-cyclohexane gradient) to give the title compound (0.213 g) as an off-white solid. LCMS (2 min, formic) Rt 0.85 min, m/z (ES$^+$) 224 (M+H).

Intermediate 4

3-(5-amino-6-methyl-2-pyridinyl)-1,3-oxazolidin-2-one

A solution of 3-(6-methyl-5-nitro-2-pyridinyl)-1,3-oxazolidin-2-one (which may be prepared, for example, according to Intermediate 3) (200 mg, 0.896 mmol) was stirred rapidly over 10% palladium on carbon (30 mg, 0.028 mmol) under an atmosphere of hydrogen at room temperature for 3 hours. The catalyst was then removed by filtration through a pad of celite. The filtrate was evaporated in vacuo to give the title compound (155 mg) as a white solid. LCMS (2 min, formic) Rt 0.38 min, m/z (ES$^+$) 194 (M+H).

Intermediate 5

4-(6-methyl-5-nitro-2-pyridinyl)morpholine

To a solution of 6-bromo-2-methyl-3-nitropyridine (2.05 g, 9.45 mmol) in ethanol (10 mL) was added morpholine (1.728 mL, 19.84 mmol) and the reaction mixture was stirred at 70° C. for 5 hours. The reaction mixture was allowed to cool to room temperature causing a precipitate. The solid was collected by filtration and washed with ethanol (5 mL), then dried in vacuo. The crude was redissolved in a mixture of saturated sodium carbonate solution and ethyl acetate. The organic phase was separated, washed with further saturated sodium carbonate solution, then dried over magnesium sulphate and evaporated in vacuo to give the title compound (1.47 g) as a yellow solid. LCMS (2 min, formic) Rt 0.92 min, m/z (ES$^+$) 224 (M+H).

Intermediate 6

2-methyl-6-(4-morpholinyl)-3-pyridinamine

A suspension of 4-(6-methyl-5-nitro-2-pyridinyl)morpholine (500 mg, 2.240 mmol), iron powder (375 mg, 6.72 mmol) and ammonium chloride (60 mg, 1.120 mmol) in ethanol (15 mL) and water (5 mL) was heated at reflux for 2 hours. The reaction mixture was filtered through a pad of celite and the pad washed with further ethyl acetate. The combined filtrate and washings were separated between ethyl acetate and saturated sodium bicarbonate and the organic phase was washed with water then brine. The organics were then separated, dried over magnesium sulphate and evaporated in vacuo to give the title compound (171 mg) as a pale brown solid. LCMS (2 min, formic) Rt 0.30 min, m/z (ES$^+$) 194 (M+H).

Intermediate 7

3,5-dimethyl-N-(2,4,4-trimethylpentan-2-yl)pyridin-2-amine

To a solution of 3,5-pyridine N-oxide (5 g, 40.6 mmol) in dichloromethane (120 mL) was added diisopropylamine (26.6 mL, 152 mmol), tert-octylamine (2,4,4-trimethylpentan-2-amine) (8.15 mL, 50.8 mmol) and bromo-tris-pyrrolidino-phosphonium hexafluorophosphate (24.61 g, 52.8 mmol). The mixture was stirred at room temperature for 18 hours, under nitrogen. Additional bromo-tris-pyrrolidino-phosphonium hexafluorophosphate (24.61 g, 52.8 mmol) and diisopropylamine (26.6 mL, 152 mmol) was added and the reaction was left to stir for 4 days. Sodium carbonate solution and dichloromethane were then added and the organic layer separated using a phase separator cartridge. The solvent was removed in vacuo and the crude purified by flash silica (Si) chromatography (0-25% ethyl acetate-cyclohexane gradient) to give the title compound (4.98 g), as a yellow oil. LCMS (2 min, High pH) Rt 1.64 mins, m/z (ES$^+$) 235 (M+H).

Intermediate 8

3,5-dimethylpyridin-2-amine 3,5-dimethyl-N-(2,4,4-trimethylpentan-2-yl)pyridin-2-amine (6.5 g, 27.7 mmol) was mixed with 2,2,2-trifluoroacetic acid (46 mL, 621 mmol) and heated to 50° C. for 4.5 hours. The mixture was concentrated in vacuo then diluted with dichloromethane (10 mL) and water (10 mL). The layers were partioned and aqueous phase was neutralised to pH 7-8 using saturated bicarbonate solution. The product was then extracted with dichloromethane (3×10 mL) and the organics were dried using a phase separator cartridge. The solvent was evaporated in vacuo to give the title compound (2.99 g) as a white solid. LCMS (2 min, High pH) Rt 0.69 min, m/z (ES$^+$) 123 (M+H).

Intermediate 9

2-chloro-N-(3,5-dimethylpyridin-2-yl)-4-fluorobenzenesulfonamide

To a solution of 2-chloro-4-fluorobenzenesulfonyl chloride (200 mg, 0.873 mmol) in pyridine (1 mL) at 25° C. was added 3,5-dimethylpyridin-2-amine (107 mg, 0.873 mmol) and the reaction mixture stirred at room temperature for 2 hours, then left to stand for 72 hours. The sample was passed through an aminopropyl (NH$_2$) solid phase extraction (SPE) cartridge eluting with methanol, then a sulphonic acid (SCX) SPE cartridge eluting with methanol followed by 2M ammonia/methanol to give the crude title compound (117 mg). This was used directly in the next step with no further purification. LCMS (2 min, High pH) Rt 0.94 min, m/z (ES$^+$) 315 (M+H).

Intermediate 10

2-chloro-N-(3,5-dimethylpyridin-2-yl)-4-fluoro-N-isobutylbenzenesulfonamide

To a solution of 2-chloro-N-(3,5-dimethylpyridin-2-yl)-4-fluorobenzenesulfonamide (117 mg, 0.372 mmol) in acetonitrile (4 mL) stirred at room temperature, was added N''-(1,1-dimethylethyl)-N,N,N',N'-tetramethylguanidine (127 mg, 0.743 mmol). The reaction mixture was stirred at room temperature for 1 hour, then 1-bromo-2-methylpropane (0.081 mL, 0.743 mmol) was added. The reaction vessel was sealed and heated under microwaves at 150° C. for 30 minutes. The solvent was evaporated in vacuo and the crude was purified by mass directed autoprep (ammonium carbonate modifier) to give the title compound (8.4 mg). LCMS (2 min, High pH) Rt 1.45 min, m/z (ES$^+$) 371 (M+H).

Intermediate 11

4-((3,5-dimethylisoxazol-4-yl)methoxy)benzenesulfonamide

4-{[(3,5-dimethyl-4-isoxazolyl)methyl]oxy}benzenesulfonyl chloride (300 mg, 0.994 mmol) was added to ammonia solution (2 mL, 92 mmol, 0.88 NH$_3$ in water). The reaction was stirred at 20° C. for 30 minutes, then left to stand overnight. The reaction mixture was diluted with methanol (5 mL) and passed sequentially through two separate aminopropyl (NH$_2$) solid phase extraction (SPE) cartridges eluting with methanol. The product-containing fractions were combined and evaporated in vacuo to give product as a yellow solid (196.2 mg). LCMS (2 min, formic) Rt 0.71 min, m/z (ES+) 283 (M+H).

Intermediate 12

N-(3,5-dimethylpyridin-2-yl)-4-fluorobenzene-sulfonamide

To a stirred solution of 3,5-dimethylpyridin-2-amine (129 mg, 1.056 mmol) in pyridine (5 mL) at room temperature, was added 4-fluorobenzene-1-sulfonyl chloride (205 mg, 1.056 mmol). The reaction mixture was stirred at 20° C. for 30 minutes, then left to stand for 16 hours. Additional 4-fluorobenzene-1-sulfonyl chloride (205 mg, 1.056 mmol) was then added and the reaction stirred for an additional 4 hours. The reaction mixture was concentrated in vacuo and purified by passing through an aminopropyl ($NH_2$) solid phase extraction (SPE) cartridge eluting with methanol, followed by a sulphonic acid (SCX) SPE cartridge eluting with methanol then 2M ammonia/methanol. Concentration of the product-containing fractions provided the title compound (84.1 mg) as a yellow oil. LCMS (2 min, formic) Rt 0.89 min, m/z (ES+) 281 (M+H).

Intermediate 13

N-(3,5-dimethylpyridin-2-yl)-4-fluoro-N-isobutyl-benzenesulfonamide

The title compound (53.7 mg) was prepared from N-(3,5-dimethylpyridin-2-yl)-4-fluorobenzenesulfonamide (84 mg, 0.300 mmol) and 1-bromo-2-methylpropane (0.065 mL, 0.599 mmol), following procedure described for Example 22. LCMS (2 min, formic) Rt 0.96 min, m/z (ES+) 337 (M+H).

Intermediate 14

6-(methyloxy)-N-(2-methylpropyl)-2-pyridinamine

To a mixture of 2-chloro-6-methoxypyridine (357 μL, 3 mmol), isobutylamine (596 μL, 6.00 mmol) and Caddick's Catalyst (prepared according to the literature reference *Org. Biomol. Chem.* 2008, 6, 2820) (35.3 mg, 0.060 mmol) under nitrogen, was added lithium hexamethyldisilazide in tetrahydrofuran (THF) (1 M, 3.750 mL, 3.75 mmol). This was warmed to 70° C. and stirred overnight, then cooled for analysis. The reaction was then further heated by microwaves to 150° C. for 30 minutes. After cooling, purification was attempted by flash silica (Si) chromatography (0-50% dichloromethane-cyclohexane gradient), but this failed to provide adequate separation. Purification was then repeated by flash silica (Si) chromatography (0-65% dichloromethane-cyclohexane gradient) to isolate the title compound (37.8 mg). LCMS (2 min, formic) Rt 0.75 min, m/z (ES+) 181 (M+H).

Intermediate 15

4-fluoro-N-isobutyl-N-(6-methoxypyridin-2-yl)ben-zenesulfonamide

A mixture of 2-(tert-butyl)-1,1,3,3-tetramethylguanidine (0.121 ml, 0.581 mmol), 1-bromo-2-methylpropane (0.126 ml, 1.162 mmol) and 4-fluoro-N-(6-methoxypyridin-2-yl) benzenesulfonamide (164 mg, 0.581 mmol) was prepared and dissolved in acetonitrile (4 mL). The reaction was heated by microwaves to 150° C. for 30 minutes, then again for a further 15 minutes. After cooling the reaction was quenched with sodium hydroxide in ethanol and concentrated in vacuo. The product was extracted to the organic phase of an acidic work up between ethyl acetate and 5% citric acid. The organic phase was dried by passing through a hydrophobic frit, concentrated in vacuo and purified by flash silica (Si) chromatography (0-25% ethyl acetate-cyclohexane gradient), to give the title compound (125.5 mg). LCMS (2 min, formic) Rt 1.33 min, m/z (ES+) 339 (M+H).

$^1$H NMR (400 MHz, DMSO-$d_6$) δ ppm 7.73-7.84 (m, 1H), 7.60-7.72 (m, 2H), 7.32-7.47 (m, 2H), 7.07 (d, 1H), 6.72 (d, 1H), 3.54 (s, 3H), 3.49 (d, 2H), 1.54 (m, 1H), 0.85 (d, 6H)

Intermediate 16

4-fluoro-N-(6-methoxypyridin-2-yl)benzenesulfona-mide

A solution of 4-fluorobenzenesulfonyl chloride (188 mg, 0.967 mmol) and 6-(methyloxy)-2-pyridinamine (100 mg, 0.806 mmol) was prepared in pyridine (5 mL). After standing, additional 4-fluorobenzenesulfonyl chloride (0.2 eq) was added and the reaction was left to stand over the weekend. The reaction mixture was then concentrated in vacuo and extracted to the organic phase of an acidic work up between ethyl acetate and 5% citric acid. The organic phase was concentrated in vacuo, to provide the title compound (164 mg) as a thick red oil. The material was used directly in the next step without further purification. LCMS (2 min, formic) Rt 0.96 min, m/z (ES+) 283 (M+H).

Intermediate 17

2-((6-methyl-5-nitropyridin-2-yl)amino)ethanol 6-bromo-2-methyl-3-nitropyridine (2 g, 9.22 mmol) was dissolved in ethanol (20 mL) and to this solution was added ethanolamine (1.115 mL, 18.43 mmol). The reaction was left to stir overnight under nitrogen, at room temperature. The reaction was concentrated in vacuo, then diluted with ethyl acetate and saturated sodium bicarbonate solution. The organic phase was separated and washed with saturated sodium bicarbonate and brine, then dried using a hydrophobic frit and concentrated in vacuo to give the title compound as a yellow solid (1.68 g). Crude material used directly in next step, without further purification. LCMS (2 min, formic) Rt 0.60 min, m/z (ES+) 198 (M+H).

Intermediate 18

3,6-dimethylpyrazin-2-amine

Ammonia in water (3 mL, 48.5 mmol) was added to 3-chloro-2,5-dimethylpyrazine (0.121 mL, 1 mmol) and the mixture heated by microwaves to 165° C. for 7 hours. Following LCMS analysis, the reaction was then reheated to 165° C. for a further 16 hours, by microwaves. After cooling, the solvent was removed under a stream of nitrogen and the crude redissolved in dichloromethane (20 mL). Water (25 mL) was added and the mixture basified to pH14 using sodium hydroxide solution (18 N). The organic layer was removed and the aqueous layer extracted with dichloromethane (5×25 mL). The organic phases were combined and dried using a hydrophobic frit, then evaporated in vacuo to give the title product (109 mg). This was used directly in the next step with no further purification. LCMS (2 min, high pH) Rt 0.47 min, m/z (ES+) 124 (M+H).

¹H NMR (400 MHz, CHLOROFORM-d) δ ppm 7.73 (s, 1H), 4.42 (br. s., 2H), 2.37 (s, 3H), 2.35 (s, 3H).

Intermediate 19

6-ethenyl-2-methyl-3-nitropyridine

A suspension/solution of 6-bromo-2-methyl-3-nitropyridine (500 mg, 2.304 mmol), 2-ethenyl-4,4,5,5-tetramethyl-1,3,2-dioxaborolane (0.782 mL, 4.61 mmol), palladium(II) acetate (25.9 mg, 0.115 mmol), X-phos (110 mg, 0.230 mmol) and cesium carbonate (3.0 g, 9.22 mmol) in 2-methyltetrahydrofuran (2-MeTHF) (8 mL) and water (2 mL) was stirred under nitrogen at 60° C. for 1 hour. The reaction mixture was cooled then separated between ethyl acetate and water. The organic phase was washed with brine and dried over magnesium sulphate. The solvent was removed in vacuo and the residue was dissolved in DCM (5 mL). This was applied to a silica cartridge and eluted with a gradient of 0-100% ethyl acetate in cyclohexane. This gave the crude product (440 mg) as a brown liquid which was used directly in the next step with no further purification. LCMS (2 min, formic) Rt 0.91 min, m/z (ES$^+$) 165 (M+H).
¹H NMR (400 MHz, CHLOROFORM-d) δ ppm 8.28 (d, 1H), 7.33 (d, 1H), 6.85 (dd, 1H), 6.40 (d, 1H), 5.70 (d, 1H), 2.89 (s, 3H).

Intermediate 20

2-methyl-3-nitro-6-[1-(phenylmethyl)-3-pyrrolidinyl]pyridine

To a solution of crude 6-ethenyl-2-methyl-3-nitropyridine (440 mg, 2.68 mmol) in dichloromethane (DCM) (5 mL) was added trifluoroacetic acid (0.268 mL, 3.48 mmol). To this stirred solution was added [(methyloxy)methyl](phenylmethyl)[(trimethylsilyl)methyl]amine (2.74 mL, 10.72 mmol) (carefully) and the reaction mixture was stirred under nitrogen for 1.5 hours. The reaction mixture was diluted with DCM and then treated with saturated sodium bicarbonate solution. The organic phase was separated and passed through a hydrophobic frit. The organic solvent was evaporated in vacuo and the residue was dissolved in DCM (5 mL). This was purified by silica (Si) chromatography (0-100% ethyl acetate-cyclohexane with 0-20% methanol gradient). The appropriate fractions were combined and evaporated in vacuo to give the crude product (201 mg) as a brown liquid. Used directly in next step without further purification. LCMS (2 min, formic) Rt 0.71 min, m/z (ES$^+$) 298 (M+H).
¹H NMR (400 MHz, CHLOROFORM-d) δ ppm 8.22 (d, 1H), 7.27-7.42 (m, 6H), 3.71 (d, 2H), 3.58-3.65 (m, 1H), 2.97-3.06 (m, 1H), 2.85 (s, 3H), 2.72-2.83 (m, 3H), 2.32-2.43 (m, 1H), 2.01-2.12 (m, 1H).

Intermediate 21

2-methyl-6-[1-(phenylmethyl)-3-pyrrolidinyl]-3-pyridinamine

To a solution of 2-methyl-3-nitro-6-[1-(phenylmethyl)-3-pyrrolidinyl]pyridine (200 mg, 0.673 mmol) in ethanol (6 mL) and water (2 mL) was added ammonium chloride (17.99 mg, 0.336 mmol) and iron powder (113 mg, 2.018 mmol). The reaction mixture was heated at reflux under nitrogen for 1 hour. The reaction mixture was filtered through a pad of celite and the pad washed with ethyl acetate. The combined filtrate and washings were separated between ethyl acetate and saturated sodium bicarbonate. The organic phase was washed with water and brine, then dried over magnesium sulphate and evaporated in vacuo to give the title product (153 mg) as a pale brown gum. LCMS (2 min, formic) Rt 0.35 min, m/z (ES$^+$) 268 (M+H).
¹H NMR (400 MHz, CHLOROFORM-d) δ ppm 7.22-7.40 (m, 5H), 6.96 (d, 1H), 6.88 (d, 1H), 3.68-3.74 (m, 2H), 3.43-3.50 (m, 3H), 2.95-3.12 (m, 1H), 2.69-2.86 (m, 2H), 2.63 (br. s., 1H), 2.40 (s, 3H), 2.26-2.36 (m, 1H), 1.92-2.09 (m, 1H).

Intermediate 22

5-isopropyl-3-methylpyridin-2-amine 3-methyl-2-nitro-5-(prop-1-en-2-yl)pyridine (221 mg, 1.24 mmol) was dissolved in ethanol (25 mL) and hydrogenated using a H-cube flow hydrogenator (settings: 20° C., 1 bar, 1 mL/min flow rate) and a 10% Pd/C CatCart (30 mm) as the catalyst. The collected solution was concentration in vacuo to give the title compound (177 mg, 95%). LCMS (2 min, formic) Rt 0.50 min, m/z (ES$^+$) 151 (M+H).

Intermediate 23

4-fluoro-N-(5-isopropyl-3-methylpyridin-2-yl)benzenesulfonamide 5-isopropyl-3-methylpyridin-2-amine (142 mg, 0.945 mmol) and 4-fluorobenzene-1-sulfonyl chloride (221 mg, 1.13 mmol) were dissolved in pyridine (3 mL) and left to stand overnight. Another 1 eq of 4-fluorobenzene-1-sulfonyl chloride was added to the mixture and the reaction left to stand for a further 6 hours. The reaction was concentrated in vacuo and the crude product extracted to the organic phase of an acidic work up between ethyl acetate and 5% citric acid. The organic phase was then passed through a hydrophobic frit, concentrated in vacuo and purified by flash silica (Si) chromatography (0-25% ethyl acetate-cyclohexane gradient). The relevant fractions were then combined and evaporated to give the title compound (127 mg). LCMS (2 min, formic) Rt 1.03 min, m/z (ES$^+$) 309 (M+H).

Intermediate 24

4-fluoro-N-isobutyl-N-(5-isopropyl-3-methylpyridin-2-yl)benzenesulfonamide 4-fluoro-N-(5-isopropyl-3-methylpyridin-2-yl)benzenesulfonamide (127 mg, 0.41 mmol) was dissolved in acetonitrile (3 mL) and to this solution was added 2-(tert-butyl)-1,1,3,3-tetramethylguanidine (0.09 mL, 0.41 mmol). The mixture was allowed to stir at room temperature for 30 minutes, 1-bromo-2-methylpropane (0.09 mL, 0.83 mmol) was then added to the mixture and the reaction vessel sealed and heated by microwaves to 150° C. for 1 hour. The reaction mixture was concentrated in vacuo and the crude product extracted to the organic phase of an aqueous workup between ethyl acetate and water. The organic phase was then passed through a hydrophobic frit, concentrated in vacuo and purified by mass directed autoprep (formic acid modifier) to give the title compound (73 mg). LCMS (2 min, formic) Rt 1.44 min, m/z (ES$^+$) 365 (M+H).

Intermediate 25

N-(5-chloro-3-methylpyridin-2-yl)-4-fluorobenzenesulfonamide

To a solution of 5-chloro-3-methylpyridin-2-amine (500 mg, 3.51 mmol) in pyridine (7 mL) stirred in air at room temperature was added a solution of 4-fluorobenzene-1-sulfonyl chloride (819 mg, 4.21 mmol) in pyridine (7 mL). The reaction mixture was stirred at 20° C. for 16 hours then the solvent was evaporated in vacuo. The crude was passed through an aminopropyl (NH$_2$) solid phase extraction (SPE) cartridge eluting with methanol followed by 2M ammonia/methanol, then a sulphonic acid (SCX) SPE cartridge eluting with methanol followed by 2M ammonia/methanol. The appropriate fractions were combined and evaporated under a stream of nitrogen to give the crude product. The crude was purified by flash silica (Si) chromatography (0-100% ethyl acetate-cyclohexane+0-20% methanol gradient). The appropriate fractions were combined and evaporated in vacuo to give the title compound (502 mg) as an off-white solid. LCMS (2 min, formic) Rt 1.02 min, m/z (ES$^+$) 301 (M+H).

Intermediate 26

N-(5-chloro-3-methylpyridin-2-yl)-4-fluoro-N-isobutylbenzenesulfonamide

N-(5-chloro-3-methylpyridin-2-yl)-4-fluorobenzenesulfonamide (502 mg, 1.67 mmol) was dissolved in acetonitrile (3.5 mL) and to this solution was added 2-(tert-butyl)-1,1,3,3-tetramethylguanidine (350 μL, 1.67 mmol). The solution was left to stir for 15 minutes then 1-bromo-2-methylpropane (363 μL, 3.34 mmol) was added. The reaction vessel was sealed and heated by microwaves to 150° C. for 1 hour. After cooling, additional 0.5 eq of 2-(tert-butyl)-1,1,3,3-tetramethylguanidine was added, along with 1 eq of 1-bromo-2-methylpropane. The reaction vessel was sealed and heated by microwaves to 150° C. for an additional 1 hour. The solution was concentrated in vacuo and the crude product extracted to the organic phase of an aqueous workup between ethyl acetate and water. The organic phase was passed through a hydrophobic frit, concentrated in vacuo and purified by flash silica (Si) chromatography (0-25% ethyl acetate-cyclohexane gradient). The relevant fractions were combined and evaporated to give the title compound (396 mg). LCMS (2 min, formic) Rt 1.38 min, m/z (ES$^+$) 357 (M+H).

Intermediate 27

4-fluoro-N-(5-isopropylpyridin-2-yl)benzenesulfonamide 5-isopropylpyridin-2-amine (300 mg, 2.20 mmol) and 4-fluorobenzene-1-sulfonyl chloride (557 mg, 2.86 mmol) were dissolved in pyridine (3 mL) and left to stand overnight. The reaction mixture was concentrated in vacuo and the crude product extracted to the organic phase of an acidic workup between ethyl acetate and 5% citric acid. The organic phase was passed through a hydrophobic frit and concentrated in vacuo to give the title compound (430 mg). LCMS (2 min, formic) Rt 0.90 min, m/z (ES$^+$) 295 (M+H).
$^1$H NMR (400 MHz, DMSO-d$_6$) δ ppm 8.00-7.76 (m, 3H), 7.69 (dd, 1H), 7.36 (t, 2H), 7.12 (d, 1H), 2.91-2.70 (m, 1H), 1.13 (d, 6H).

Intermediate 28

4-fluoro-N-isobutyl-N-(5-isopropylpyridin-2-yl)benzenesulfonamide 4-fluoro-N-(5-isopropylpyridin-2-yl)benzenesulfonamide (400 mg, 1.359 mmol) was dissolved in acetonitrile (4 mL), 2-(tert-butyl)-1,1,3,3-tetramethylguanidine (284 μL, 1.36 mmol) added and the mixture stirred for 20 minutes. 1-Bromo-2-methylpropane (296 μL, 2.72 mmol) was then added and the reaction vessel sealed and heated by microwaves to 150° C. for 1 hour. The reaction was cooled and concentrated in vacuo, then the crude product was extracted to the organic phase of an aqueous work up between ethyl acetate and water. The organic phase was passed through a hydrophobic frit, concentrated in vacuo and purified by mass directed autoprep (formic acid modifier) to give the title compound (117 mg). LCMS (2 min, formic) Rt 1.38 min, m/z (ES$^+$) 351 (M+H).

Intermediate 29

N-(2-methylpropyl)-2-(trifluoromethyl)-4-pyrimidinamine

A mixture of 4-chloro-2-(trifluoromethyl)pyrimidine (548 mg, 3 mmol) and triethylamine (0.460 mL, 3.30 mmol) in isobutylamine (1.5 mL) was stirred at room temperature for 11 hours and 30 minutes (Care: exotherm). The mixture was evaporated, then dichloromethane (DCM) (5 mL) and water (5 mL) added. The organic layer was separated and purified by silica (Si) chromatography (0-100% ethyl acetate-cyclohexane gradient). The relevant fractions were combined and concentrated to yield the title compound, 548 mg. LCMS (2 min, formic) Rt 1.08 min, m/z (ES$^+$) 220 (M+H).

Intermediate 30

4-fluoro-N-(5-isopropylpyridin-2-yl)-N-(3-methylbutan-2-yl)benzenesulfonamide

To a solution of 4-fluoro-N-(5-isopropylpyridin-2-yl)benzenesulfonamide (203 mg, 0.690 mmol) and 3-methylbutan-2-ol (60.8 mg, 0.690 mmol) in toluene (3 mL) stirred in air at room temperature was added a solution of 2-tributylphosphoranylidene)acetonitrile (166 mg, 0.690 mmol) in toluene (0.5 mL). The reaction vessel was sealed and heated by microwaves to 150° C. for 30 minutes. After cooling, the solvent was evaporated in vacuo and the crude purified by mass directed autoprep (formic acid modifier) to give the title product (32 mg) as a colourless oil. LCMS (2 min, formic) Rt 1.41 min, m/z (ES$^+$) 365 (M+H).

Intermediate 31

N-(5-bromo-3-methoxypyridin-2-yl)-4-fluorobenzenesulfonamide

To a solution of 5-bromo-3-methoxypyridin-2-amine (100 mg, 0.493 mmol) in pyridine (1 mL) stirred in air at room temperature was added a solution of 4-fluorobenzene-1-sulfonyl chloride (115 mg, 0.591 mmol) in pyridine (1 mL). The reaction mixture was stirred at 20° C. for 16 hours then the solvent was evaporated in vacuo to give the crude product. The crude was passed through an aminopropyl (NH$_2$) solid phase extraction (SPE) cartridge eluting with methanol followed by 2M ammonia/methanol, then a sulphonic acid (SCX) SPE cartridge eluting with methanol followed by 2M ammonia/methanol. The appropriate fractions were combined and evaporated under a stream of nitrogen to give the crude product. Final purification by flash silica (Si) chromatography (0-100% ethyl acetate-cyclohexane+0-20% methanol gradient), gave the title product (133 mg) as an off-white solid. LCMS (2 min, formic) Rt 1.03 min, m/z (ES$^+$) 361/363 (M+H).

Intermediate 32

4-fluoro-N-(3-methoxy-5-(prop-1-en-2-yl)pyridin-2-yl)benzenesulfonamide

Potassium trifluoro(prop-1-en-2-yl)borate (53.3 mg, 0.360 mmol), N-(5-bromo-3-methoxypyridin-2-yl)-4-fluorobenzenesulfonamide (130 mg, 0.360 mmol), caesium carbonate (352 mg, 1.080 mmol), palladium(II) chloride (1.276 mg, 7.20 μmol) and triphenylphosphine (5.66 mg, 0.022 mmol) were added to a microwave vial and suspended in tetrahydrofuran (THF) (2 mL) and water (0.2 mL). The reaction vessel was sealed and heated by microwaves to 140° C. for 30 minutes. After cooling, the mixture was diluted with dichloromethane (DCM) (5 mL) and water (5 mL), then passed through a celite column. The aqueous phase was washed with further DCM (5 mL) then the organics separated using a hydrophobic frit and concentrated in vacuo to give the crude product. This was purified by flash silica (Si) chromatography (0-50% ethyl acetate-cyclohexane gradient) to give the title product (75 mg). LCMS (2 min, formic) Rt 1.0 min, m/z (ES$^+$) 323 (M+H).

Intermediate 33

4-fluoro-N-(5-isopropyl-3-methoxypyridin-2-yl)benzenesulfonamide

A solution of 4-fluoro-N-(3-methoxy-5-(prop-1-en-2-yl)pyridin-2-yl)benzenesulfonamide (75 mg, 0.233 mmol) was prepared in ethanol (5 mL). The mixture was hydrogenated using a H-cube flow hydrogenator (settings: 20° C., 1 bar, 1 mL/min flow rate) and 10% Pd/C CatCart (30 mm) as the catalyst. The collected solvent was evaporated to give title product (55 mg). LCMS (2 min, formic) Rt 1.01 min, m/z (ES$^+$) 325 (M+H).

Intermediate 34

4-fluoro-N-isobutyl-N-(5-isopropyl-3-methoxypyridin-2-yl)benzenesulfonamide

The title compound (46.8 mg) was prepared from 4-fluoro-N-(5-isopropyl-3-methoxypyridin-2-yl)benzenesulfonamide (55 mg, 0.170 mmol), 2-(tert-butyl)-1,1,3,3-tetramethylguanidine (0.068 mL, 0.339 mmol) in acetonitrile (4 mL) and 1-bromo-2-methylpropane (0.037 mL, 0.339 mmol) following the procedure described for Example 40. LCMS (2 min, formic) Rt 1.34 min, m/z (ES$^+$) 381 (M+H).

Intermediate 35

4-((3,5-dimethylisoxazol-4-yl)methoxy)-N-(4,6-dimethylpyrimidin-2-yl)benzenesulfonamide To a solution of 4,6-dimethylpyrimidin-2-amine (84 mg, 0.682 mmol) in pyridine (8 mL), stirred under nitrogen at room temperature, was added 4-((3,5-dimethylisoxazol-4-yl)methoxy)benzene-1-sulfonyl chloride (346 mg, 1.147 mmol). The reaction mixture was stirred at room temperature overnight. 2-(tert-butyl)-1,1,3,3-tetramethylguanidine (0.142 mL, 0.682 mmol) was then added to the mixture and the reaction heated by microwaves to 150° C. for 15 minutes. Dichloromethane (DCM) (15 mL) was added to the mixture and the organic phase washed with water (2×25 mL), then dried using a hydrophobic frit. Solvent was removed in vacuo to give the crude product (100 mg) as an orange oil. This was used directly in the next step without further purification. LCMS (2 min, formic) Rt 0.81 min, m/z (ES$^+$) 389 (M+H).

Intermediate 36

4-((3,5-dimethylisoxazol-4-yl)-methoxy)-N-(5-isopropylpyridin-2-yl)benzenesulfonamide To a solution of 4-((3,5-dimethylisoxazol-4-yl)methoxy)benzene-1-sulfonyl chloride (241 mg, 0.800 mmol) in pyridine (5 mL), stirred under nitrogen at room temperature, was added 5-isopropylpyridin-2-amine (54.5 mg, 0.4 mmol). The mixture was then stirred at room temperature overnight. Dichloromethane (25 mL) was added to the mixture and the organic phase washed with water (25 mL) and brine (25 mL) then dried using a hydrophobic frit. Solvent was removed in vacuo to give the crude product. This was purified by flash silica (Si) chromatography (0-100% ethyl acetate-cyclohexane gradient), to provide the title compound (39 mg) as an off-white solid. LCMS (2 min, formic) Rt 0.96 min, m/z (ES$^+$) 402 (M+H).
$^1$H NMR (400 MHz, METHANOL-d$_4$) δ ppm 7.80-7.92 (m, 3H), 7.63 (dd, 1H), 7.16 (d, 1H), 7.07 (d, 2H), 4.94 (s, 2H), 2.77-2.92 (m, 1H), 2.39 (s, 3H), 2.23 (s, 3H), 1.20 (d, 6H).

Intermediate 37

4-((3,5-dimethylisoxazol-4-yl)-methoxy)-N-(5-methylpyridin-2-yl)benzenesulfonamide To a solution of 5-methylpyridin-2-amine (54 mg, 0.5 mmol) in pyridine (5 mL) stirred at room temperature, was added 4-((3,5-dimethylisoxazol-4-yl)methoxy)benzene-1-sulfonyl chloride (0.151 g, 0.5 mmol). The reaction was stirred at room temperature overnight. The solvent was then removed under a stream of nitrogen to give the crude product, which was used directly in the next reaction with no purification. LCMS (2 min, formic) Rt 0.84 min, m/z (ES$^+$) 374 (M+H).

Intermediate 38

4-((3,5-dimethylisoxazol-4-yl)-methoxy)-N-(4-methylpyridin-2-yl)benzenesulfonamide The title compound was prepared from 4-methylpyridin-2-amine (54 mg, 0.5 mmol) following the procedure described for Intermediate 37, and used directly in the next reaction with no purification. LCMS (2 min, formic) Rt 0.80 min, m/z (ES$^+$) 374 (M+H).

Intermediate 39

4-((3,5-dimethylisoxazol-4-yl)-methoxy)-N-(6-methylpyridin-2-yl)benzenesulfonamide The title compound was prepared from 6-methylpyridin-2-amine (54 mg, 0.5 mmol) following the procedure described for Intermediate 37, and used directly in the next reaction with no purification. LCMS (2 min, formic) Rt 0.79 min, m/z (ES$^+$) 374 (M+H).

Intermediate 40

4-((3,5-dimethylisoxazol-4-yl)-methoxy)-N-(3-methylpyridin-2-yl)benzenesulfonamide The title compound was prepared from 3-methylpyridin-2-amine (54 mg, 0.5 mmol) following the procedure described for Intermediate 37, and used directly in the next reaction with no purification. LCMS (2 min, formic) Rt 0.85 min, m/z (ES+) 374 (M+H).

Intermediate 41

N-(5-chloropyridin-2-yl)-4-((3,5-dimethylisoxazol-4-yl)methoxy)benzenesulfonamide The title compound was prepared from 5-chloropyridin-2-amine (64 mg, 0.5 mmol) following the procedure described for Intermediate 37, and used directly in the next reaction with no purification. LCMS (2 min, formic) Rt 1.01 min, m/z (ES+) 394 (M+H).

Intermediate 42

4-((3,5-dimethylisoxazol-4-yl)-methoxy)-N-(5-fluoropyridin-2-yl)benzenesulfonamide The title compound was prepared from 5-fluoropyridin-2-amine (56 mg, 0.5 mmol) following the procedure described for Intermediate 37, and used directly in the next reaction with no purification. LCMS (2 min, formic) Rt 0.93 min, m/z (ES+) 378 (M+H).

Intermediate 43

4-((3,5-dimethylisoxazol-4-yl)methoxy)-N-(2,6-dimethylpyridin-3-yl)benzenesulfonamide The title compound was prepared from 2,6-dimethylpyridin-3-amine (61 mg, 0.5 mmol) following the procedure described for Intermediate 37, and used directly in the next reaction with no purification. LCMS (2 min, formic) Rt 0.64 min, m/z (ES+) 388 (M+H).

Intermediate 44

4-((3,5-dimethylisoxazol-4-yl)-methoxy)-N-(6-methylpyridin-3-yl)benzenesulfonamide The title compound was prepared from 6-methylpyridin-3-amine (54 mg, 0.5 mmol) following the procedure described for Intermediate 37, and used directly in the next reaction with no purification. LCMS (2 min, formic) Rt 0.71 min, m/z (ES+) 374 (M+H).

Intermediate 45

4-((3,5-dimethylisoxazol-4-yl)-methoxy)-N-(4-methylpyridin-3-yl)benzenesulfonamide The title compound was prepared from 4-methylpyridin-3-amine (54 mg, 0.5 mmol) following the procedure described for Intermediate 37, and used directly in the next reaction with no purification. LCMS (2 min, formic) Rt 0.68 min, m/z (ES+) 374 (M+H).

Intermediate 46

4-((3,5-dimethylisoxazol-4-yl)methoxy)-N-(3,5-dimethylpyrazin-2-yl)benzenesulfonamide The title compound was prepared from 3,5-dimethylpyrazin-2-amine (62 mg, 0.5 mmol) following the procedure described for Intermediate 37, and used directly in the next reaction with no purification. LCMS (2 min, formic) Rt 0.86 min, m/z (ES+) 389 (M+H).

Intermediate 47

4-((3,5-dimethylisoxazol-4-yl)-methoxy)-N-(2-methylpyridin-4-yl)benzenesulfonamide The title compound was prepared from 2-methylpyridin-4-amine (54 mg, 0.5 mmol) following the procedure described for Intermediate 37, and used directly in the next reaction with no purification. LCMS (2 min, formic) Rt 0.63 min, m/z (ES+) 374 (M+H).

Intermediate 48

4-{[(3,5-dimethyl-4-isoxazolyl)methyl]oxy}-N-(3,5-dimethyl-2-pyridinyl)benzenesulfonamide To a solution of pyridine (0.083 mL, 1.023 mmol) and 3,5-dimethyl-2-pyridinamine (125 mg, 1.023 mmol) in dichloromethane (1 mL) was added 4-{[(3,5-dimethyl-4-isoxazolyl)methyl]oxy}benzenesulfonyl chloride (309 mg, 1.023 mmol). The mixture was heated at 70° C. for 4 hours. Water (5 mL) was added and the organic phase separated and purified by flash silica (Si) chromatography (50% dichloromethane-ethyl acetate gradient) to give the title compound (56 mg) as a bright yellow solid. LCMS (2 min, formic) Rt 0.93 min, m/z (ES+) 388 (M+H).

Intermediate 49

4-{[(3,5-dimethyl-4-isoxazolyl)methyl]oxy}-N-[2-methyl-6-(2-oxo-1,3-oxazolidin-3-yl)-3-pyridinyl]benzenesulfonamide To a solution of 3-(5-amino-6-methyl-2-pyridinyl)-1,3-oxazolidin-2-one (80 mg, 0.414 mmol) in dichloromethane (3 mL) and pyridine (0.033 mL, 0.414 mmol) was added 4-{[(3,5-dimethyl-4-isoxazolyl)methyl]oxy}benzenesulfonyl chloride (125 mg, 0.414 mmol). The reaction vessel was sealed and heated at 65° C. for 6 hours. The reaction mixture was then allowed to cool and separated between dichloromethane (40 mL) and saturated sodium bicarbonate solution (30 mL). The organic phase was separated using a hydrophobic frit and evaporated in vacuo. The crude was then purified by flash silica (Si) chromatography (0-100% ethyl acetate-cyclohexane gradient). The appropriate fractions were combined and evaporated in vacuo to give the title compound (137 mg) as a colourless glassy solid. LCMS (2 min, formic) Rt 0.92 min, m/z (ES+) 459 (M+H).

Intermediate 50

4-{[(3,5-dimethyl-4-isoxazolyl)methyl]oxy}-N-[2-methyl-6-(4-morpholinyl)-3-pyridinyl]benzenesulfonamide A mixture of 2-methyl-6-(4-morpholinyl)-3-pyridinamine (170 mg, 0.880 mmol) and 4-{[(3,5-dimethyl-4-isoxazolyl)methyl]oxy}benzenesulfonyl chloride (265 mg, 0.880 mmol) in dichloromethane (4 mL) and pyridine (0.142 mL, 1.759 mmol) was heated at 65° C. for 2 hours. The reaction mixture was allowed to cool and separated between dichloromethane and saturated sodium bicarbonate solution. The organic phase was passed through a hydrophobic frit and evaporated in vacuo. The crude was purified by flash silica (Si) chromatography (0-100% ethyl acetate-cyclohexane gradient) to give the title compound (271 mg) as an off-white solid. LCMS (2 min, formic) Rt 0.82 min, m/z (ES$^+$) 459 (M+H).

Intermediate 51

4-{[(3,5-dimethyl-4-isoxazolyl)methyl]oxy}-N-[6-(methyloxy)-3-pyridazinyl]benzenesulfonamide To a solution of 6-methoxypyridazin-3-amine (125 mg, 1.0 mmol) in pyridine (8 mL) at room temperature, was added 4-{[(3,5-dimethyl-4-isoxazolyl)methyl]oxy}benzenesulfonyl chloride (0.302 g, 1.0 mmol). The reaction mixture was stirred at 20° C. for 18 hours. The solvent was evaporated in vacuo and passed through an aminopropyl (NH$_2$) solid phase extraction (SPE) cartridge eluting with methanol, followed by a sulphonic acid (SCX) SPE cartridge eluting with methanol. The crude was then purified by flash silica (Si) chromatography (0-100% ethyl acetate-cyclohexane+0-25% methanol gradient), to provide the title compound (16 mg). LCMS (2 min, formic) Rt 0.83 min, m/z (ES$^+$) 391 (M+H).

Intermediate 52

4-((3,5-dimethylisoxazol-4-yl)-methoxy)-N-(6-ethoxypyridazin-3-yl)benzenesulfonamide The title compound (16 mg) was prepared from 6-ethoxypyridazin-3-amine (129 mg, 1.0 mmol) and 4-{[(3,5-dimethyl-4-isoxazolyl)methyl]oxy}benzenesulfonyl chloride (0.302 g, 1.0 mmol), following the procedure described for Intermediate 51. LCMS (2 min, formic) Rt 0.91 min, m/z (ES$^+$) 405 (M+H).

Intermediate 53

4-((3,5-dimethylisoxazol-4-yl)-methoxy)-N-(5-ethylpyrimidin-2-yl)benzenesulfonamide A suspension of 2-chloro-5-ethylpyrimidine (0.021 mL, 0.177 mmol), 4-{[(3,5-dimethyl-4-isoxazolyl)methyl] oxy}benzenesulfonamide (50 mg, 0.177 mmol), palladium (II) acetate (0.397 mg, 1.770 µmol), Xantphos (2.048 mg, 3.54 µmol) and cesium carbonate (144 mg, 0.443 mmol) was prepared in 1,4-dioxane (2 mL). The reaction vessel was sealed and heated by microwaves to 130° C. for 30 minutes. After cooling the reaction, additional Xantphos (2.048 mg, 3.54 µmol) and palladium(II) acetate (0.397 mg, 1.770 µmol) were added. The reaction was heated by microwaves to 130° C. for a further 30 minutes. The reaction mixture was then diluted with methanol (2 mL) and passed through a silica solid phase extraction (SPE) cartridge to remove particulates. The filtrate was evaporated in vacuo and purified by mass directed autoprep (formic acid modifier) to give the title compound (19 mg). LCMS (2 min, formic) Rt 0.93 min, m/z (ES$^+$) 389 (M+H)

Intermediate 54

N-(5-cyanopyridin-2-yl)-4-((3,5-dimethylisoxazol-4-yl)methoxy)benzenesulfonamide To a solution of 6-amino-3-pyridinecarbonitrile (30 mg, 0.252 mmol) in pyridine (1 mL) at room temperature, was added 4-{[(3,5-dimethyl-4-isoxazolyl)methyl]oxy}benzenesulfonyl chloride (84 mg, 0.277 mmol). The reaction mixture was stirred at 20° C. for 30 minutes, then left to stand overnight. The solvent was evaporated in vacuo. The sample was purified by passing through an aminopropyl (NH$_2$) solid phase extraction (SPE) cartridge eluting with methanol, followed by a sulphonic acid (SCX) SPE cartridge eluting with methanol then 2M ammonia/methanol. The product-containing fractions were concentrated to give the title compound (23 mg) as an off-white solid. LCMS (2 min, formic) Rt 0.88 min, m/z (ES$^+$) 385 (M+H)

Intermediate 55

4-((3,5-dimethylisoxazol-4-yl)-methoxy)-N-(3-ethyl-6-methylpyridin-2-yl)benzenesulfonamide The title compound (70.1 mg) was prepared from 3-ethyl-6-methylpyridin-2-amine (0.091 g, 0.3 mmol) and 4-((3,5-dimethylisoxazol-4-yl)methoxy)benzene-1-sulfonyl chloride (0.136 g, 0.45 mmol), following the procedure described for Intermediate 54. LCMS (2 min, formic) Rt 1.02 min, m/z (ES$^+$) 402 (M+H).

Intermediate 56

4-((3,5-dimethylisoxazol-4-yl)methoxy)-N-(3,6-dimethylpyrazin-2-yl)benzenesulfonamide The title compound (44 mg) was prepared from 3,6-dimethylpyrazin-2-amine (46 mg, 0.374 mmol) following the procedure described for Intermediate 35, and used directly in the next reaction with no purification. LCMS (2 min, formic) Rt 0.88 min, m/z (ES$^+$) 389 (M+H).

Intermediate 57

4-((3,5-dimethylisoxazol-4-yl)-methoxy)-N-(4-methylpyrimidin-5-yl)benzenesulfonamide The title compound (187 mg) was prepared from 4-methylpyrimidin-5-amine (55 mg, 0.5 mmol) following the procedure described for Intermediate 37, and used directly in the next reaction with no purification. LCMS (2 min, formic) Rt 0.80 min, m/z (ES$^+$) 375 (M+H).

Intermediate 58

4-{[(3,5-dimethyl-4-isoxazolyl)methyl]oxy}-N-{2-methyl-6-[1-(phenylmethyl)-3-pyrrolidinyl]-3-pyridinyl}benzenesulfonamide To a solution of 2-methyl-6-[1-(phenylmethyl)-3-pyrrolidinyl]-3-pyridinamine (150 mg, 0.561 mmol) in dichloromethane (DCM) (4 mL) and pyridine (0.045 mL, 0.561 mmol) was added 4-{[(3,5-dimethyl-4-isoxazolyl)methyl] oxy}benzenesulfonyl chloride (169 mg, 0.561 mmol). The reaction vessel was sealed and heated at 65° C. for 2 hours. Additional 4-{[(3,5-dimethyl-4-isoxazolyl)methyl] oxy}benzenesulfonyl chloride (169 mg, 0.561 mmol) and pyridine (0.045 mL, 0.561 mmol) were added and the reaction mixture was heated for a further 4 hours at 65° C. The reaction mixture was then cooled and separated between DCM (40 mL) and saturated sodium bicarbonate solution (30 mL). The organic phase was passed through a hydrophobic frit and evaporated in vacuo. The sample was purified by flash silica (Si) chromatography (0-25% methanol-dichloromethane gradient). The appropriate fractions were combined and evaporated in vacuo to give the title product (211 mg) as a brown gum (approx 71% pure). LCMS (2 min, formic) Rt 0.80 min, m/z (ES+) 533 (M+H)

Intermediate 59

N-(6-(1-benzylpyrrolidin-3-yl)-2-methylpyridin-3-yl)-4-((3,5-dimethylisoxazol-4-yl)methoxy)-N-isobutylbenzenesulfonamide To a solution of 4-{[(3,5-dimethyl-4-isoxazolyl)methyl]oxy}-N-{2-methyl-6-[1-(phenylmethyl)-3-pyrrolidinyl]-3-pyridinyl}benzenesulfonamide (211 mg, 0.396 mmol) and N''-(1,1-dimethylethyl)-N,N,N',N'-tetramethylguanidine (67.9 mg, 0.396 mmol) in acetonitrile (3 mL) was added 1-bromo-2-methylpropane (0.086 mL, 0.792 mmol). The reaction vessel was sealed and heated at 80° C. for 8 hours. The reaction mixture was separated between ethyl acetate and saturated sodium bicarbonate solution. The organic phase was washed with brine and dried over magnesium sulphate. The solvent was removed in vacuo. The sample was purified by flash silica (Si) chromatography (0-25% methanol-dichloromethane gradient). The appropriate fractions were combined and evaporated in vacuo to give the required product (114 mg) as a brown gum. LCMS (2 min, formic) Rt 1.01 min, m/z (ES+) 589 (M+H)

$^1$H NMR (400 MHz, CHLOROFORM-d) δ ppm 7.60 (d, 2H), 7.29-7.43 (m, 4H), 6.94-7.06 (m, 5H), 4.86 (s, 2H), 3.66-3.74 (m, 2H), 3.31-3.60 (m, 2H), 2.93-3.19 (m, 2H), 2.67-2.84 (m, 3H), 2.42-2.50 (m, 6H), 2.32 (s, 3H), 2.00-2.12 (m, 2H), 1.22-1.31 (m, 1H), 1.01 (d, 3H), 0.85 (dd, 3H).

Intermediate 60 tert-butyl cis-3-fluoro-4-((4-(N-isobutyl-N-(5-isopropyl-3-methylpyridin-2-yl)sulfamoyl)phenoxy)methyl)piperidine-1-carboxylate 4-fluoro-N-isobutyl-N-(5-isopropyl-3-methylpyridin-2-yl)benzenesulfonamide (35 mg, 0.10 mmol) was dissolved in N,N-dimethylformamide (DMF) (3 mL) and to this solution was added sodium hydride (2 mg, 0.10 mmol, 60% wt in mineral oil) followed by tert-butyl cis-3-fluoro-4-(hydroxymethyl)piperidine-1-carboxylate (22 mg, 0.10 mmol). The reaction was stirred overnight at room temperature, under nitrogen, then quenched with water and concentrated in vacuo. The crude product was extracted to the organic phase of an aqueous workup between ethyl acetate and water. The organic phase was then passed through a hydrophobic frit and concentrated in vacuo to give the title compound (53 mg). LCMS (2 min, formic) Rt 1.53 min, m/z (ES+) 578 (M+H).

Intermediate 61 tert-butyl cis-3-fluoro-4-((4-(N-isobutyl-N-(5-isopropylpyridin-2-yl)sulfamoyl)phenoxy)methyl)piperidine-1-carboxylate 4-fluoro-N-isobutyl-N-(5-isopropylpyridin-2-yl)benzenesulfonamide (30 mg, 0.10 mmol) was dissolved in N,N-dimethylformamide (DMF) (3 mL) and to this solution was added sodium hydride (2 mg, 0.10 mmol, 60% wt in mineral oil) followed by tert-butyl cis-3-fluoro-4-(hydroxymethyl)piperidine-1-carboxylate (24 mg, 0.10 mmol). The reaction was stirred for 3 hours at room temperature, under nitrogen, then quenched with water and concentrated in vacuo. The crude product was extracted to the organic phase of an aqueous workup between ethyl acetate and water. The organic phase was then passed through a hydrophobic frit and concentrated in vacuo to give the title compound (47 mg). LCMS (2 min, formic) Rt 1.50 min, m/z (ES+) 564 (M+H).

Intermediate 62

4-((3,5-dimethylisoxazol-4-yl)methoxy)-N-(5-isopropylpyridin-2-yl)benzenesulfonamide To a stirred solution of 4-((3,5-dimethylisoxazol-4-yl)methoxy)benzene-1-sulfonyl chloride (500 mg, 1.66 mmol) in pyridine (5 mL) at 25° C. was added 5-isopropylpyridin-2-amine (226 mg, 1.66 mmol). The reaction mixture was stirred at 25° C. for 2 hours, then left to stand at this temperature overnight. The crude reaction mixture was then purified by flash silica (Si) chromatography (0-50% ethyl acetate-cyclohexane gradient). The appropriate fractions were combined and concentrated in vacuo to give the title compound (454 mg) as an orange solid. LCMS (2 min, formic) Rt 1.00 min, m/z (ES+) 402 (M+H).

Intermediate 63

N-(2-cyclopropylpyrimidin-5-yl)-4-((3,5-dimethylisoxazol-4-yl)methoxy)benzenesulfonamide To a solution of 2-cyclopropylpyrimidin-5-amine (50 mg, 0.370 mmol) in pyridine (1 mL) stirred in air at room temperature was added 4-{[(3,5-dimethyl-4-isoxazolyl)methyl]oxy}benzenesulfonyl chloride (123 mg, 0.407 mmol). The reaction mixture was stirred at 20° C. for 30 minutes, to ensure dissolution and then left to stand overnight. The solvent was evaporated in vacuo to give the crude product which was purified by mass directed autoprep (formic acid modifier) to give the title product (74.5 mg). LCMS (2 min, formic) Rt 0.94 min, m/z (ES+) 401 (M+H).

Intermediate 64

N-(5-isopropylpyridin-2-yl)-4-vinylbenzenesulfonamide

To a solution of 5-isopropylpyridin-2-amine (400 mg, 2.94 mmol) in pyridine (5 mL), stirred at room temperature, was added 4-vinylbenzene-1-sulfonyl chloride (760 mg, 3.75 mmol). The reaction mixture was stirred for 30 minutes then stood overnight. The solvent was evaporated in vacuo and the crude sample purified by normal phase chromatography on silica (Si) (0-50% ethyl acetate-cyclohexane gradient). The appropriate fractions were combined and evaporated in vacuo to give the title product, 670 mg, as an off-white solid. LCMS (2 min, formic) Rt 0.98 min, m/z (ES+) 303 (M+H).

Intermediate 65

N-isobutyl-N-(5-isopropylpyridin-2-yl)-4-vinylbenzenesulfonamide

To a solution of N-(5-isopropylpyridin-2-yl)-4-vinylbenzenesulfonamide (507 mg, 1.677 mmol) in acetonitrile (10 mL), was added 2-(tert-butyl)-1,1,3,3-tetramethylguanidine (0.676 mL, 3.35 mmol). The mixture was stirred at room temperature for 1 hour, then 1-bromo-2-methylpropane (0.676 mL, 3.35 mmol) added. The reaction was then heated by microwaves to 150° C., for 30 minutes. After cooling, the solvent was removed under a stream of nitrogen and the crude purified by normal phase chromatography on silica (Si)

(0-50% ethyl acetate-cyclohexane gradient). The appropriate fractions were combined and evaporated in vacuo to give the title product, 179 mg, as a yellow oil which solidified on standing. LCMS (2 min, High pH) Rt 1.49 min, m/z (ES$^+$) 359 (M+H).

Intermediate 66

2-(N-isobutyl-4-(oxiran-2-yl)phenylsulfonamido)-5-isopropylpyridine 1-oxide

A solution of N-isobutyl-N-(5-isopropylpyridin-2-yl)-4-vinylbenzenesulfonamide (179 mg, 0.499 mmol) was prepared in dichloromethane (DCM) (10 mL) and meta-chloroperoxybenzoic acid (345 mg, 1.997 mmol) added at 0° C. The reaction was warmed to room temperature and stirred overnight at 20° C. The reaction mixture was then washed with water (30 mL), sodium hydroxide solution (2M, 2×30 mL) and brine (30 mL), then dried with a hydrophobic frit and concentrated in vacuo to give the product, 176 mg. This was used directly in the next step without further purification. LCMS (2 min, High pH) Rt 1.10 min, m/z (ES$^+$) 391 (M+H).

Intermediate 67

2-(4-(1-hydroxy-2-((3-methyloxetan-3-yl)-amino)ethyl)-N-isobutylphenylsulfonamido)-5-isopropylpyridine 1-oxide A solution of 2-(N-isobutyl-4-(oxiran-2-yl)phenylsulfonamido)-5-isopropylpyridine 1-oxide (145 mg, 0.371 mmol) was prepared in ethanol (3 mL) and 3-methyloxetan-3-amine (0.129 mL, 1.485 mmol) added. The reaction was heated to 50° C. and stirred for 24 hours. The solvent was evaporated in vacuo to give the crude product which was purified by mass-directed autoprep (ammonium carbonate modifier). The solvent was removed under a stream of nitrogen to give the title product, 71.9 mg. LCMS (2 min, formic) Rt 0.73 min, m/z (ES$^+$) 478 (M+H).

Intermediate 68

4-fluoro-N-(5-isopropylpyridin-2-yl)-N-(oxetan-3-ylmethyl)benzenesulfonamide

To a solution of 4-fluoro-N-(5-isopropylpyridin-2-yl)benzenesulfonamide (100 mg, 0.340 mmol) and oxetan-3-ylmethanol (20.95 mg, 0.238 mmol) in toluene (1.5 mL) stirred in air at room temperature was added a solution of 2-(tributylphosphoranylidene)acetonitrile (82 mg, 0.340 mmol) in toluene (0.5 mL). The reaction mixture was stirred at 20° C. for 16 hours. Additional 2-(tributylphosphoranylidene)acetonitrile (82 mg, 0.340 mmol) and oxetan-3-ylmethanol (20.95 mg, 0.238 mmol) were added and the solution stirred for a further 24 hours. The reaction solution was then purified on an aminopropyl (NH$_2$) solid phase extraction (SPE) cartridge eluting with a 0-50% ethyl acetate-cyclohexane gradient, to give the title product (63 mg) as a colourless gum. LCMS (2 min, formic) Rt 1.12 min, m/z (ES$^+$) 365 (M+H).

Intermediate 69

4-((3,5-dimethylisoxazol-4-yl)methoxy)-N-(pyrazin-2-yl)benzenesulfonamide

The title compound (180 mg) was prepared from pyrazin-2-amine (48 mg, 0.5 mmol) following the procedure described for Intermediate 37 and used directly in the next reaction with no purification. LCMS (2 min, formic) Rt 0.80 min, m/z (ES$^+$) 361 (M+H).

Intermediate 70

4-((3,5-dimethylisoxazol-4-yl)methoxy)-N-(pyrimidin-5-yl)benzenesulfonamide

The title compound (180 mg) was prepared from pyrimidin-5-amine (48 mg, 0.5 mmol) following the procedure described for Intermediate 37 and used directly in the next reaction with no purification. LCMS (2 min, formic) Rt 0.80 min, m/z (ES$^+$) 361 (M+H).

Intermediate 71

4-((3,5-dimethylisoxazol-4-yl)methoxy)-N-(2-methylpyrimidin-5-yl)benzenesulfonamide The title compound (187 mg) was prepared from 2-methylpyrimidin-5-amine (55 mg, 0.5 mmol) following the procedure described for Intermediate 37 and used directly in the next reaction with no purification. LCMS (2 min, formic) Rt 0.81 min, m/z (ES$^+$) 375 (M+H).

Intermediate 72

4-((3,5-dimethylisoxazol-4-yl)-methoxy)-N-(5-methylpyridin-3-yl)benzenesulfonamide The title compound (187 mg) was prepared from 5-methylpyridin-3-amine (54 mg, 0.5 mmol) following the procedure described for Intermediate 37 and used directly in the next reaction with no purification. LCMS (2 min, formic) Rt 0.77 min, m/z (ES$^+$) 374 (M+H).

Intermediate 73

4-{[(3,5-dimethyl-4-isoxazolyl)methyl]oxy}-N-(4,6-dimethyl-3-pyridinyl)benzenesulfonamide 4-{[(3,5-dimethyl-4-isoxazolyl)methyl]oxy}benzenesulfonyl chloride (247 mg, 0.819 mmol) was added to a solution of triethylamine (0.114 mL, 0.819 mmol) and 4,6-dimethyl-3-pyridinamine (100 mg, 0.819 mmol) in dichloromethane (1 mL). The mixture was heated at 70° C. for 2 hours. To the mixture was added water (5 mL) then the organic layer separated and purified by silica (Si) chromatography (100% ethyl acetate). The relevant fractions were combined and concentrated to give the title product (310 mg) as a yellow solid. LCMS (2 min, formic) Rt 0.63 mins, m/z (ES$^+$) 388 (M+H).

Intermediate 74

N-(6-cyclopropylpyridazin-3-yl)-4-((3,5-dimethylisoxazol-4-yl)methoxy)benzenesulfonamide To a solution of 6-cyclopropylpyridazin-3-amine (50 mg, 0.370 mmol) in pyridine (1 mL), stirred under nitrogen at room temperature, was added 4-((3,5-dimethylisoxazol-4-yl)methoxy)benzene-1-sulfonyl chloride (346 mg, 1.147 mmol). The reaction mixture was stirred at room temperature for 16 hours. The mixture was evaporated and purified by solid phase extraction (SPE) using an aminopropyl (NH$_2$) cartridge with sequential solvents methanol then 2M ammonia/methanol. The appropriate fractions were combined and evaporated in vacuo to give the crude product. The crude was further purified by mass directed autoprep (formic acid modifier). The relevant fractions were removed under a stream of nitrogen to give the title product (51 mg). LCMS (2 min, formic) Rt 0.86 min, m/z (ES⁺) 401 (M+H).

Intermediate 75

2-(4-(1-hydroxy-2-morpholinoethyl)-N-isobutylphenylsulfonamido)-5-isopropylpyridine 1-oxide A solution of 2-(N-isobutyl-4-(oxiran-2-yl)phenylsulfonamido)-5-isopropylpyridine 1-oxide (176 mg, 0.451 mmol) was prepared in ethanol (3 mL) and morpholine (0.157 mL, 1.803 mmol) added. The reaction was heated at 50° C. and stirred for 18 hours. After cooling, the solvent was evaporated in vacuo and the crude sample purified by mass directed autoprep (ammonium carbonate modifier). The relevant fractions were evaporated under a stream of nitrogen to give the title product, 130 mg. LCMS (2 min, High pH) Rt 1.01 min, m/z (ES⁺) 478 (M+H).

EXAMPLE PREPARATION

Example 1

4-((3,5-dimethylisoxazol-4-yl)methoxy)-N-(4,6-dimethylpyrimidin-2-yl)-N-isobutylbenzenesulfonamide

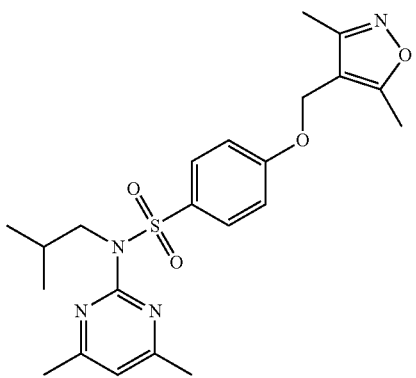 [SMILES: Cc1cc(C)nc(N(CC(C)C)S(=O)(=O)c2ccc(OCc3c(C)noc3C)cc2)n1]

To a solution of 4-((3,5-dimethylisoxazol-4-yl)methoxy)-N-(4,6-dimethylpyrimidin-2-yl)benzenesulfonamide (100 mg, 0.257 mmol) in acetonitrile (5 mL) stirred at room temperature, was added 2-(tert-butyl)-1,1,3,3-tetramethylguanidine (0.054 mL, 0.257 mmol). The mixture was stirred at room temperature for 1 hour, then 1-bromo-2-methylpropane (0.056 mL, 0.515 mmol) added. The reaction was then heated by microwaves to 150° C., for 25 minutes. After cooling the solvent was removed under a stream of nitrogen and the crude sample purified by mass directed autoprep (formic acid modifier). The solvent was removed under a stream of nitrogen to give the title product (11.7 mg) as a yellow oil which solidified. LCMS (2 min, formic) Rt 1.31 min, m/z (ES⁺) 445 (M+H).

¹H NMR (400 MHz, METHANOL-d₄) δ ppm 7.97 (d, 2H), 7.09 (d, 2H), 6.73 (s, 1H), 4.96 (s, 2H), 4.05 (d, 2H), 2.39 (s, 3H), 2.30 (s, 6H), 2.24 (s, 3H), 2.12-2.23 (m, 1H), 0.94 (d, 6H)

Example 2

4-((3,5-dimethylisoxazol-4-yl)-methoxy)-N-isobutyl-N-(5-isopropylpyridin-2-yl)benzenesulfonamide

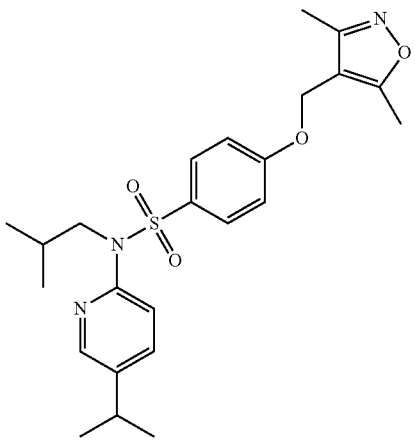 [SMILES: Cc1noc(C)c1COc1ccc(S(=O)(=O)N(CC(C)C)c2ccc(C(C)C)cn2)cc1]

The title compound (7.6 mg) was prepared from 4-((3,5-dimethylisoxazol-4-yl)methoxy)-N-(5-isopropylpyridin-2-yl)benzenesulfonamide (39 mg, 0.097 mmol) and 2-(tert-butyl)-1,1,3,3-tetramethylguanidine (0.020 mL, 0.097 mmol) in acetonitrile (2 mL), following the procedure described for Example 1. LCMS (2 min, formic) Rt 1.37 min, m/z (ES⁺) 458 (M+H).

¹H NMR (400 MHz, METHANOL-d₄) δ ppm 8.17 (d, 1H), 7.73 (dd, 1H), 7.50 (d, 2H), 7.46 (d, 1H), 7.07 (d, 2H), 4.96 (s, 2H), 3.49 (d, 2H), 2.96 (m, 1H), 2.41 (s, 3H), 2.25 (s, 3H), 1.53 (m, 1H), 1.27 (d, 6H), 0.86 (d, 6H).

Example 3

4-((3,5-dimethylisoxazol-4-yl)-methoxy)-N-isobutyl-N-(5-methylpyridin-2-yl)benzenesulfonamide

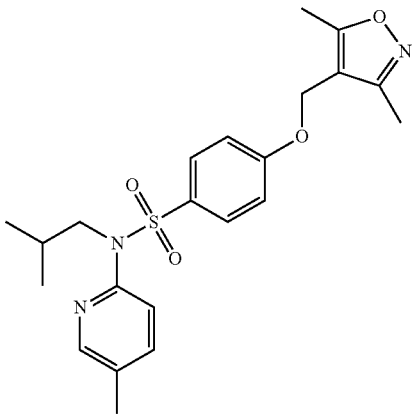 [SMILES: Cc1ccc(N(CC(C)C)S(=O)(=O)c2ccc(OCc3c(C)noc3C)cc2)nc1]

To a solution of 4-((3,5-dimethylisoxazol-4-yl)methoxy)-N-(5-methylpyridin-2-yl)benzenesulfonamide (187 mg, 0.5 mmol) in acetonitrile (5 mL) stirred at room temperature, was added 2-(tert-butyl)-1,1,3,3-tetramethylguanidine (0.261 mL, 1.250 mmol). The mixture was stirred at room temperature for 1 hour, then 1-bromo-2-methylpropane (0.190 mL, 1.750 mmol) added. The reaction was then heated by microwaves to 160° C., for 25 minutes. After cooling, dichlormethane (5 mL) was added to the mixture and the organic phase washed with water (5 mL) then separated using a hydrophobic frit. The solvent was removed under a stream of nitrogen and the crude sample purified by mass directed autoprep (ammonium carbonate modifier) to give the title product (8.5 mg). LCMS (3 min, High pH) Rt 1.88 min, m/z (ES+) 430 (M+H).

$^1$H NMR (600 MHz, DMSO-$d_6$) δ ppm 8.18 (s, 1H), 7.70 (d, 1H), 7.47 (d, 2H), 7.40 (d, 1H), 7.12 (d, 2H), 5.00 (s, 2H), 3.43 (d, 2H), 2.41 (s, 3H), 2.28 (s, 3H), 2.21 (s, 3H), 1.45 (m, 1H), 0.80 (d, 6H).

Example 4

4-((3,5-dimethylisoxazol-4-yl)methoxy)-N-isobutyl-N-(4-methylpyridin-2-yl)benzenesulfonamide

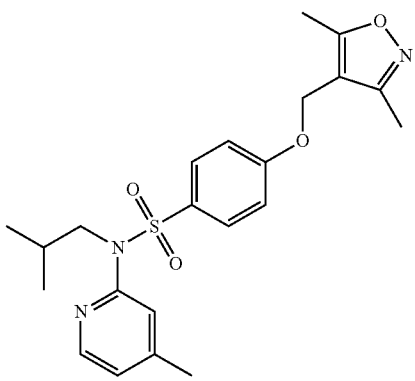 [SMILES: Cc1ccnc(N(CC(C)C)S(=O)(=O)c2ccc(OCc3c(C)noc3C)cc2)c1]

The title compound (9 mg) was prepared from 4-((3,5-dimethylisoxazol-4-yl)methoxy)-N-(4-methylpyridin-2-yl)benzenesulfonamide (187 mg, 0.5 mmol) following the procedure described for Example 3. LCMS (3 min, High pH) Rt 1.88 min, m/z (ES+) 430 (M+H).

$^1$H NMR (600 MHz, DMSO-$d_6$) δ ppm 8.20 (d, 1H), 7.48 (d, 2H), 7.36 (s, 1H), 7.10-7.17 (m, 3H), 5.00 (br. s., 2H), 3.45 (d, 2H), 2.41 (s, 3H), 2.37 (s, 3H), 2.20 (s, 3H), 1.42-1.51 (m, 1H), 0.81 (d, 6H).

Example 5

4-((3,5-dimethylisoxazol-4-yl)-methoxy)-N-isobutyl-N-(6-methylpyridin-2-yl)benzenesulfonamide

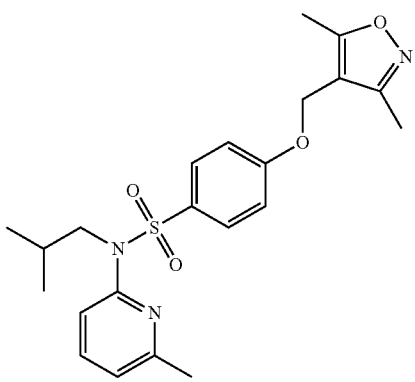 [SMILES: Cc1cccc(N(CC(C)C)S(=O)(=O)c2ccc(OCc3c(C)noc3C)cc2)n1]

The title compound (26.9 mg) was prepared from 4-((3,5-dimethylisoxazol-4-yl)methoxy)-N-(6-methylpyridin-2-yl)benzenesulfonamide (187 mg, 0.5 mmol) following the procedure described for Example 3. LCMS (3 min, High pH) Rt 1.91 min, m/z (ES+) 430 (M+H).

$^1$H NMR (600 MHz, DMSO-$d_6$) δ ppm 7.74 (t, 1H), 7.53 (d, 2H), 7.29 (d, 1H), 7.11-7.15 (m, 3H), 5.01 (s, 2H), 3.47 (d, 2H), 2.40 (s, 3H), 2.32 (s, 3H), 2.20 (s, 3H), 1.52-1.57 (m, 1H), 0.81 (d, 6H).

Example 6

4-((3,5-dimethylisoxazol-4-yl)methoxy)-N-isobutyl-N-(3-methylpyridin-2-yl)benzenesulfonamide

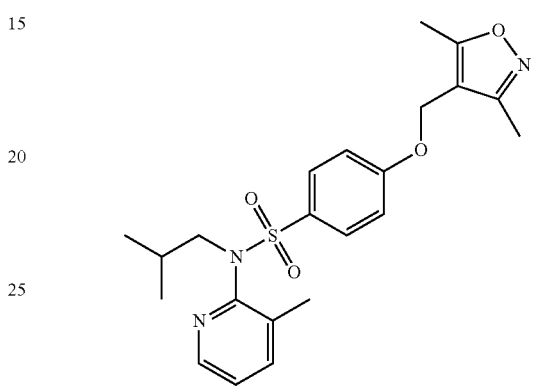

The title compound (4.9 mg) was prepared from 4-((3,5-dimethylisoxazol-4-yl)methoxy)-N-(3-methylpyridin-2-yl)benzenesulfonamide (187 mg, 0.5 mmol) following the procedure described for Example 3. LCMS (3 min, High pH) Rt 1.88 min, m/z (ES+) 430 (M+H).

$^1$H NMR (600 MHz, DMSO-$d_6$) δ ppm 8.23 (d, 1H), 7.81 (d, 1H), 7.52 (d, 2H), 7.31 (dd, 1H), 7.16 (d, 2H), 5.03 (s, 2H), 3.25 (br. s., 2H), 2.47 (s, 3H), 2.43 (s, 3H), 2.23 (s, 3H), 1.27-1.33 (m, 1H), 0.81 (br. s., 6H).

Example 7

N-(5-chloropyridin-2-yl)-4-((3,5-dimethylisoxazol-4-yl)-methoxy)-N-isobutylbenzenesulfonamide

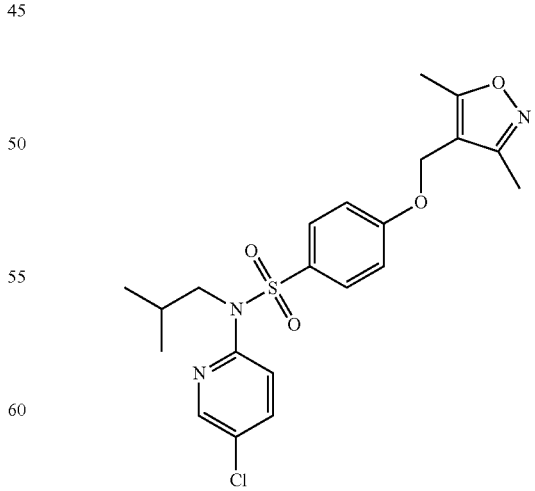

The title compound (15.9 mg) was prepared from N-(5-chloropyridin-2-yl)-4-((3,5-dimethylisoxazol-4-yl)methoxy)benzenesulfonamide (197 mg, 0.5 mmol) following the procedure described for Example 3. LCMS (3 min, High pH) Rt 2.04 min, m/z (ES+) 450 (M+H).

¹H NMR (600 MHz, DMSO-d₆) δ ppm 8.42 (d, 1H), 8.02 (dd, 1H), 7.58 (d, 1H), 7.51 (d, 2H), 7.14 (d, 2H), 5.00 (s, 2H), 3.47 (d, 2H), 2.41 (s, 3H), 2.21 (s, 3H), 1.48-1.55 (m, 1H), 0.81 (d, 6H).

Example 8

4-((3,5-dimethylisoxazol-4-yl)-methoxy)-N-(5-fluoropyridin-2-yl)-N-isobutyl benzenesulfonamide

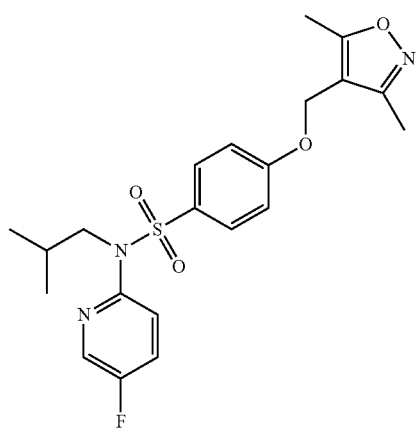 [SMILES: Cc1noc(C)c1COc1ccc(S(=O)(=O)N(CC(C)C)c2ccc(F)cn2)cc1]

The title compound (34.1 mg) was prepared from 4-((3,5-dimethylisoxazol-4-yl)methoxy)-N-(5-fluoropyridin-2-yl) benzenesulfonamide (189 mg, 0.5 mmol) following the procedure described for Example 3. LCMS (3 min, High pH) Rt 1.9 min, m/z (ES+) 434 (M+H).

¹H NMR (600 MHz, DMSO-d₆) δ ppm 8.37 (d, 1H), 7.85 (td, 1H), 7.59 (dd, 1H), 7.48 (d, 2H), 7.13 (d, 2H), 5.00 (s, 2H), 3.42 (d, 2H), 2.41 (s, 3H), 2.21 (s, 3H), 1.42-1.48 (m, 1H), 0.81 (d, 6H).

Example 9

4-((3,5-dimethylisoxazol-4-yl)methoxy)-N-(2,6-dimethylpyridin-3-yl)-N-isobutyl benzenesulfonamide

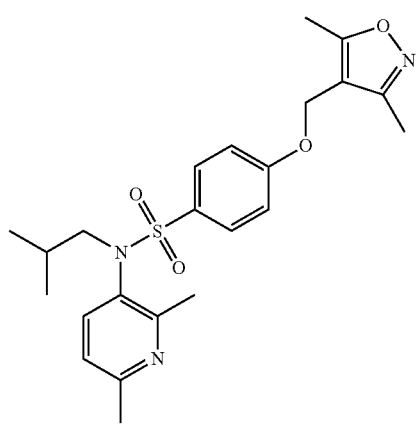 [SMILES: Cc1ccc(N(CC(C)C)S(=O)(=O)c2ccc(OCc3c(C)noc3C)cc2)c(C)n1]

The title compound (77.6 mg) was prepared from 4-((3,5-dimethylisoxazol-4-yl)methoxy)-N-(2,6-dimethylpyridin-3-yl)benzenesulfonamide (194 mg, 0.5 mmol) following the procedure described for Example 3. LCMS (3 min, High pH) Rt 1.7 min, m/z (ES+) 444 (M+H).

¹H NMR (600 MHz, DMSO-d₆) δ ppm 7.54 (d, 2H), 7.20 (d, 2H), 7.03 (d, 1H), 6.98 (d, 1H), 5.04 (s, 2H), 3.36-3.41 (m, 1H), 3.08 (dd, 1H), 2.43 (s, 3H), 2.42 (s, 3H), 2.41 (s, 3H), 2.22 (s, 3H), 1.36-1.44 (m, 1H), 0.93 (d, 3H), 0.77 (d, 3H).

Example 10

4-((3,5-dimethylisoxazol-4-yl)methoxy)-N-isobutyl-N-(6-methylpyridin-3-yl)benzenesulfonamide

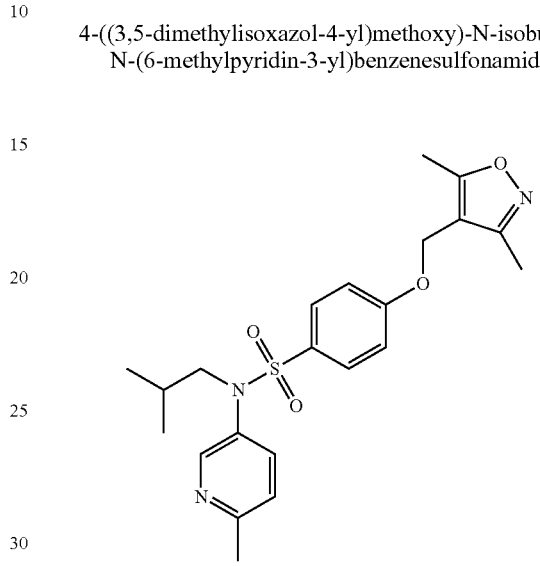

The title compound (70.2 mg) was prepared from 4-((3,5-dimethylisoxazol-4-yl)methoxy)-N-(6-methylpyridin-3-yl) benzenesulfonamide (187 mg, 0.5 mmol) following the procedure described for Example 3. LCMS (3 min, High pH) Rt 1.68 min, m/z (ES+) 430 (M+H).

¹H NMR (600 MHz, DMSO-d₆) δ ppm 8.17 (s, 1H), 7.49 (d, 2H), 7.37 (dd, 1H), 7.24 (d, 1H), 7.18 (d, 2H), 5.02 (s, 2H), 3.32 (d, 2H), 2.46 (s, 3H), 2.42 (s, 3H), 2.22 (s, 3H), 1.40 (m, 1H), 0.84 (d, 6H).

Example 11

4-((3,5-dimethylisoxazol-4-yl)methoxy)-N-isobutyl-N-(4-methylpyridin-3-yl)benzenesulfonamide

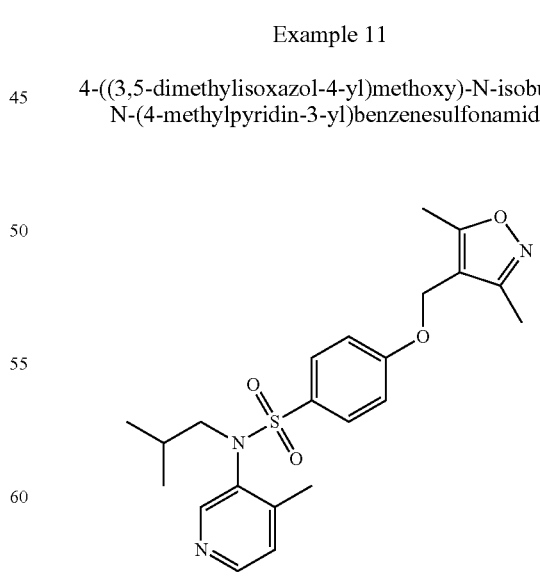

The title compound (34.2 mg) was prepared from 4-((3,5-dimethylisoxazol-4-yl)methoxy)-N-(4-methylpyridin-3-yl) benzenesulfonamide (187 mg, 0.5 mmol) following the procedure described for Example 3. LCMS (3 min, High pH) Rt 1.69 min, m/z (ES+) 430 (M+H).

$^1$H NMR (600 MHz, DMSO-d$_6$) δ ppm 8.36 (d, 1H), 7.85 (s, 1H), 7.57 (d, 2H), 7.35 (d, 1H), 7.21 (d, 2H), 5.05 (d, 2H), 3.39-3.43 (m, 1H), 3.23 (dd, 1H), 2.43 (s, 3H), 2.28 (s, 3H), 2.23 (s, 3H), 1.43 (m, 1H), 0.93 (d, 3H), 0.78 (d, 3H).

Example 12

4-((3,5-dimethylisoxazol-4-yl)methoxy)-N-(3,5-dimethylpyrazin-2-yl)-N-isobutylbenzenesulfonamide

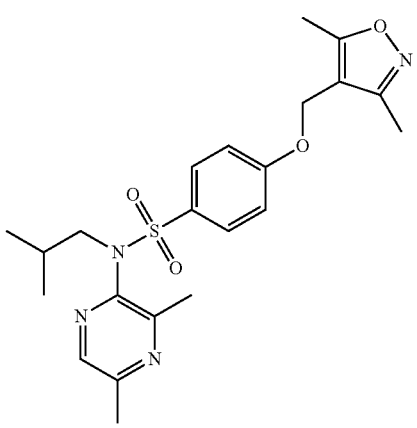 [SMILES: Cc1cnc(N(CC(C)C)S(=O)(=O)c2ccc(OCc3c(C)noc3C)cc2)c(C)n1]

The title compound (23.3 mg) was prepared from 4-((3,5-dimethylisoxazol-4-yl)methoxy)-N-(3,5-dimethylpyrazin-2-yl)benzenesulfonamide (194 mg, 0.5 mmol) following the procedure described for Example 3. LCMS (3 min, High pH) Rt 1.79 min, m/z (ES+) 445 (M+H).

$^1$H NMR (600 MHz, DMSO-d$_6$) δ ppm 8.20 (s, 1H), 7.52 (d, 2H), 7.17 (d, 2H), 5.03 (s, 2H), 3.24 (d, 2H), 2.64 (s, 3H), 2.49 (s, 3H), 2.43 (s, 3H), 2.23 (s, 3H), 1.33 (m, 1H), 0.82 (br. s., 6H).

Example 13

4-((3,5-dimethylisoxazol-4-yl)methoxy)-N-isobutyl-N-(2-methylpyridin-4-yl)benzenesulfonamide

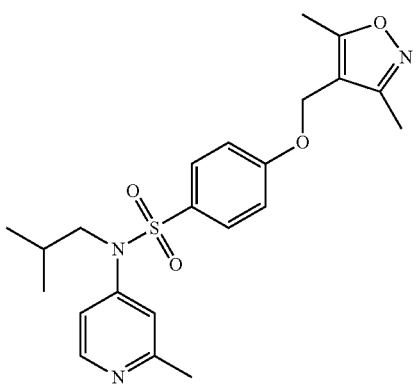 [SMILES: Cc1cc(N(CC(C)C)S(=O)(=O)c2ccc(OCc3c(C)noc3C)cc2)ccn1]

The title compound (10.8 mg) was prepared from 4-((3,5-dimethylisoxazol-4-yl)methoxy)-N-(2-methylpyridin-4-yl)benzenesulfonamide (187 mg, 0.5 mmol) following the procedure described for Example 3. LCMS (3 min, High pH) Rt 1.66 min, m/z (ES+) 430 (M+H).

$^1$H NMR (600 MHz, DMSO-d$_6$) δ ppm 8.37 (d, 1H), 7.53 (d, 2H), 7.16 (d, 2H), 7.13 (s, 1H), 6.96-7.06 (m, 1H), 5.01 (s, 2H), 3.40 (d, 2H), 2.43 (s, 3H), 2.41 (s, 3H), 2.20 (s, 3H), 1.51 (m, 1H), 0.83 (d, 6H).

Example 14

4-{[(3,5-dimethyl-4-isoxazolyl)methyl]oxy}-N-(2-methylpropyl)-N-[4-(trifluoromethyl)-2-pyrimidinyl]benzenesulfonamide

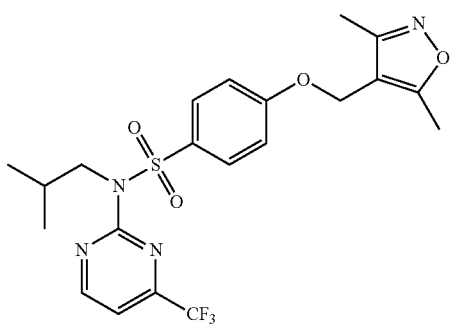 [SMILES: Cc1noc(C)c1COc1ccc(S(=O)(=O)N(CC(C)C)c2nccc(C(F)(F)F)n2)cc1]

To a suspension of 4-hydroxy-N-(2-methylpropyl)-N-[4-(trifluoromethyl)-2-pyrimidinyl]benzenesulfonamide (31 mg, 0.083 mmol) and potassium fluoride on alumina (30 mg, 0.207 mmol) in acetonitrile (0.5 mL) stirred under nitrogen at room temperature was added a solution of 4-(chloromethyl)-3,5-dimethylisoxazole (12 mg, 0.083 mmol) in acetonitrile (0.5 mL). The reaction mixture was stirred at 20° C. for 16 hours. The reaction mixture was filtered to remove the potassium fluoride on alumina and the filtrate evaporated. The sample was purified by mass directed autoprep (TFA modifier). The solvent was evaporated under a stream of nitrogen and then freeze-dried from water/dioxane to give the title compound (49 mg). LCMS (2 min, formic) Rt 1.35 min, m/z (ES+) 485 (M+H).

$^1$H NMR (400 MHz, DMSO-d$_6$) δ ppm 8.99-8.87 (m, 1H), 8.06-7.93 (m, 2H), 7.61-7.49 (m, 1H), 7.23-7.04 (m, 2H), 5.01 (s, 2H), 4.10-3.97 (m, 2H), 2.39 (s, 3H), 2.28-2.12 (m, 4H), 0.93 (d, 6H).

Example 15

4-{[(3,5-dimethyl-4-isoxazolyl)methyl]oxy}-N-(3,5-dimethyl-2-pyridinyl)-N-(2-methylpropyl)benzenesulfonamide

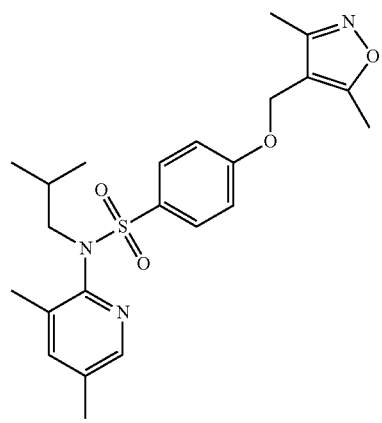 [SMILES: Cc1cnc(N(CC(C)C)S(=O)(=O)c2ccc(OCc3c(C)noc3C)cc2)c(C)c1]

To a solution of 4-{[(3,5-dimethyl-4-isoxazolyl)methyl]oxy}-N-(3,5-dimethyl-2-pyridinyl)benzenesulfonamide (56 mg, 0.145 mmol) in acetonitrile (1 mL) was added N''-(1,1-dimethylethyl)-N,N,N',N'-tetramethylguanidine (25 mg, 0.145 mmol) and the mixture was stirred at room temperature for 1 hour, 1-bromo-2-methylpropane (0.031 mL, 0.289 mmol) was then added and the mixture was stirred at 70° C. for 125 hours. The mixture was concentrated in vacuo and partitioned between dichloromethane (5 mL) and water (5 mL). The organic layer was then purified by mass directed autoprep (formic acid modifier) to give the title compound (30 mg) as a white solid. LCMS (2 min, formic) Rt 1.31 min, m/z (ES$^+$) 444 (M+H).

$^1$H NMR (400 MHz, METHANOL-d$_4$) δ ppm 7.99 (d, 1H), 7.57-7.59 (m, 1H), 7.55 (d, 2H), 7.11 (d, 2H), 4.99 (s, 2H), 3.26-3.29 (m, 2H), 2.48 (s, 3H), 2.43 (s, 3H), 2.31 (s, 3H), 2.27 (s, 3H), 1.33-1.45 (m, 1H), 0.86 (br. s., 6H).

Example 16

4-{[(3,5-dimethyl-4-isoxazolyl)methyl]oxy}-N-[2-methyl-6-(2-oxo-1,3-oxazolidin-3-yl)-3-pyridinyl]-N-(2-methylpropyl)benzenesulfonamide

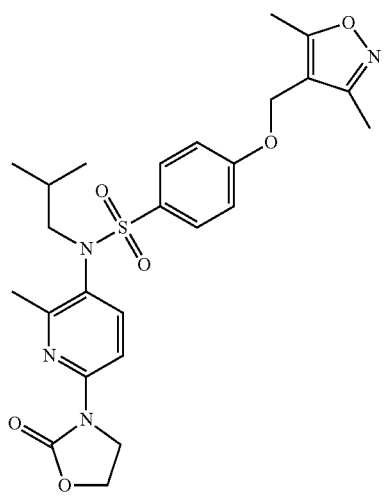 [SMILES: Cc1nc(N2CCOC2=O)ccc1N(CC(C)C)S(=O)(=O)c1ccc(OCc2c(C)noc2C)cc1]

To a solution of 4-{[(3,5-dimethyl-4-isoxazolyl)methyl]oxy}-N-[2-methyl-6-(2-oxo-1,3-oxazolidin-3-yl)-3-pyridinyl]benzenesulfonamide (137 mg, 0.299 mmol) and N''-(1,1-dimethylethyl)-N,N,N',N'-tetramethylguanidine (51 mg, 0.299 mmol) in acetonitrile (2 mL) was added 1-bromo-2-methylpropane (0.065 mL, 0.598 mmol). The reaction vessel was heated at 80° C. for 8 hours. The reaction mixture was then separated between ethyl acetate and saturated sodium bicarbonate solution. The organic phase was washed with brine, dried over magnesium sulphate then concentrated in vacuo. The crude was purified by flash silica (Si) chromatography (0-100% ethyl acetate-cyclohexane gradient) to give the title compound (100 mg) as a white foam. LCMS (2 min, formic) Rt 1.21 min, m/z (ES$^+$) 515 (M+H).

$^1$H NMR (400 MHz, CHLOROFORM-d) δ ppm 8.00-7.88 (m, 1H), 7.58 (d, 2H), 7.07-6.95 (m, 2H), 6.88 (d, 1H), 4.87 (d, 2H), 4.49 (d, 2H), 4.39-4.23 (m, 2H), 3.56-3.42 (m, 1H), 3.00 (d, 1H), 2.59 (s, 3H), 2.46 (s, 3H), 2.33 (s, 3H), 1.62-1.50 (m, 1H), 1.05 (d, 3H), 0.83 (d, 3H).

Example 17

4-{[(3,5-dimethyl-4-isoxazolyl)methyl]oxy}-N-[2-methyl-6-(4-morpholinyl)-3-pyridinyl]-N-(2-methylpropyl)benzenesulfonamide

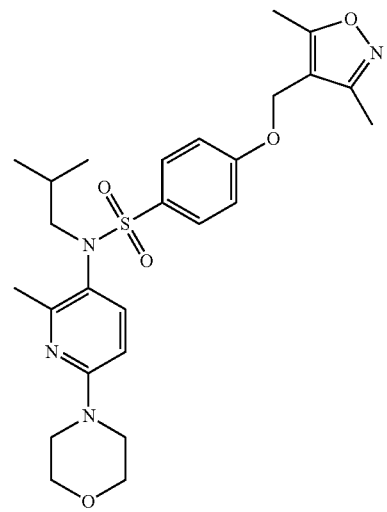 [SMILES: Cc1nc(N2CCOCC2)ccc1N(CC(C)C)S(=O)(=O)c1ccc(OCc2c(C)noc2C)cc1]

The title compound (104 mg) was prepared as an off-white foam, from 4-{[(3,5-dimethyl-4-isoxazolyl)methyl]oxy}-N-[2-methyl-6-(4-morpholinyl)-3-pyridinyl]benzenesulfonamide (105 mg, 0.229 mmol), following the procedure described for Example 16, with reaction time reduced to 2 hours. LCMS (2 min, formic) Rt 0.18 min, m/z (ES$^+$) 515 (M+H).

$^1$H NMR (400 MHz, CHLOROFORM-d) δ ppm 7.67-7.56 (m, 2H), 7.04-6.94 (m, 2H), 6.87 (d, 1H), 6.34 (d, 1H), 3.88-3.76 (m, 4H), 3.59-3.46 (m, 4H), 3.36 (dd, 1H), 3.08 (dd, 1H), 2.50-2.39 (m, 3H), 2.37-2.27 (m, 6H), 1.70-1.50 (m, 3H), 1.01 (d, 3H) and 0.86 (d, 3H).

Example 18

2-chloro-N-(3,5-dimethylpyridin-2-yl)-N-isobutyl-4-((tetrahydro-2H-pyran-4-yl)methoxy)benzenesulfonamide

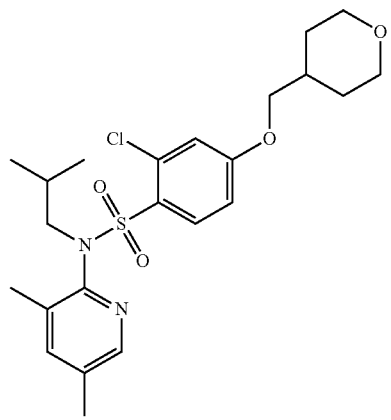 [SMILES: Cc1cnc(N(CC(C)C)S(=O)(=O)c2ccc(OCC3CCOCC3)cc2Cl)c(C)c1]

To a stirred solution of 4-(hydroxylmethyl)tetrahydro-2H-pyran (2.63 mg, 0.023 mmol) and 2-chloro-N-(3,5-dimethylpyridin-2-yl)-4-fluoro-N-isobutylbenzenesulfonamide (8.4 mg, 0.023 mmol) in dimethyl sulfoxide (200 µL) at room temperature was added sodium hydride (60% wt in mineral oil) (0.906 mg, 0.023 mmol) and the reaction stirred for 2 hours. The reaction was quenched with methanol (2 mL) and water (2 mL), then the solvents evaporated in vacuo. The crude product was purified by flash silica (Si) chromatography (25% ethyl acetate-cyclohexane gradient) to give the title compound (5.2 mg). LCMS (2 min, High pH) Rt 1.48 min, m/z (ES+) 468 (M+H).

$^1$H NMR (400 MHz, METHANOL-d$_4$) δ ppm 7.97 (d, 1H), 7.76 (d, 1H), 7.59-7.49 (m, 1H), 7.09-6.99 (m, 1H), 6.94 (dd, 1H), 4.03-3.86 (m, 4H), 3.54-3.40 (m, 4H), 3.34 (s, 3H), 2.46 (s, 3H), 2.30 (s, 3H), 2.08 (m, 1H), 1.81-1.69 (m, 2H) and 0.88 (d, 6H).

Example 19

4-((3,5-dimethylisoxazol-4-yl)-methoxy)-N-isobutyl-N-(6-methoxypyridazin-3-yl)benzenesulfonamide

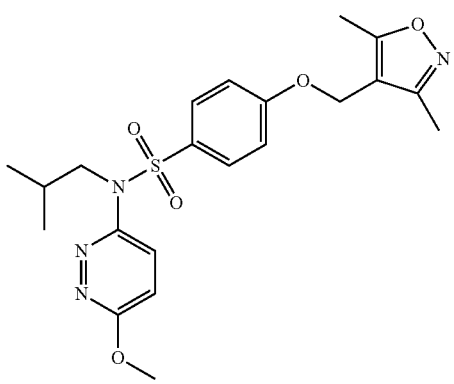 [SMILES: COc1ccc(N(CC(C)C)S(=O)(=O)c2ccc(OCc3c(C)noc3C)cc2)nn1]

To a solution of 4-{[(3,5-dimethyl-4-isoxazolyl)methyl]oxy}-N-[6-(methyloxy)-3-pyridazinyl]benzenesulfonamide (16 mg, 0.041 mmol) in acetonitrile (1 mL) stirred at room temperature was added N''-(1,1-dimethylethyl)-N,N,N',N'-tetramethylguanidine (7.02 mg, 0.041 mmol). The reaction mixture was stirred at 20° C. for 1 hour, then 1-bromo-2-methylpropane (8.91 µL, 0.082 mmol) was added. The reaction was heated by microwaves to 150° C. for 15 minutes. After cooling, the reaction mixture was diluted with methanol and passed through an aminopropyl (NH$_2$) solid phase extraction (SPE) cartridge followed by a sulphonic acid (SCX) SPE cartridge, eluting with methanol. The appropriate fractions were combined and evaporated under a stream of nitrogen to give the crude product. The crude was purified by mass directed autoprep (formic acid modifier), to provide the title compound (1.0 mg). LCMS (2 min, formic) Rt 1.27 min, m/z (ES+) 447 (M+H).

$^1$H NMR (400 MHz, METHANOL-d$_4$) δ ppm 7.76 (d, 1H), 7.47-7.60 (m, 2H), 7.21 (d, 1H), 7.06-7.15 (m, 2H), 4.97 (s, 2H), 4.06 (s, 3H), 3.55 (d, 2H), 2.42 (s, 3H), 2.26 (s, 3H), 1.59 (m, 1H), 0.87 (d, 6H).

Example 20

4-((3,5-dimethylisoxazol-4-yl)methoxy)-N-(6-ethoxypyridazin-3-yl)-N-isobutylbenzenesulfonamide

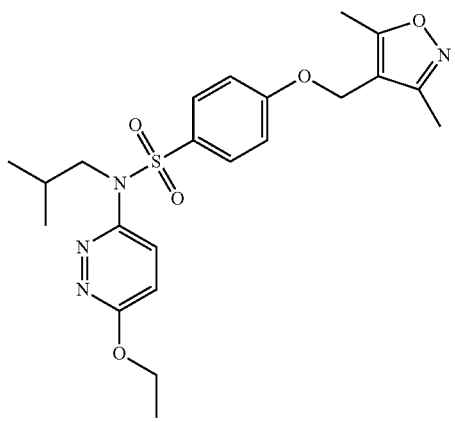 [SMILES: CCOc1ccc(N(CC(C)C)S(=O)(=O)c2ccc(OCc3c(C)noc3C)cc2)nn1]

The title compound (1.7 mg) was prepared from 4-{[(3,5-dimethyl-4-isoxazolyl)methyl]oxy}-N-[6-(ethyloxy)-3-pyridazinyl]benzenesulfonamide (16 mg, 0.040 mmol), following the procedure described for Example 19. LCMS (2 min, formic) Rt 1.27 min, m/z (ES+) 461 (M+H).

$^1$H NMR (400 MHz, METHANOL-d$_4$) δ ppm 7.77 (d, 1H), 7.48-7.60 (m, 2H), 7.20 (d, 1H), 7.08-7.16 (m, 2H), 4.98 (s, 2H), 4.48 (q, 2H), 3.56 (d, 2H), 2.43 (s, 3H), 2.27 (s, 3H), 1.60 (m, 1H), 1.44 (t, 3H), 0.89 (d, 6H).

Example 21

4-((3,5-dimethylisoxazol-4-yl)methoxy)-N-(5-ethylpyrimidin-2-yl)-N-isobutylbenzenesulfonamide

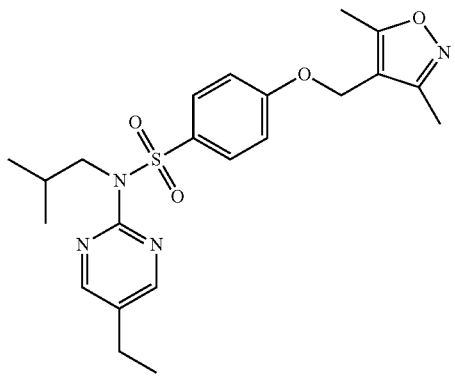 [SMILES: CCc1cnc(N(CC(C)C)S(=O)(=O)c2ccc(OCc3c(C)noc3C)cc2)nc1]

The title compound (8.1 mg) was prepared from 4-{[(3,5-dimethyl-4-isoxazolyl)methyl]oxy}-N-(5-ethyl-2-pyrimidinyl)benzenesulfonamide (19 mg, 0.049 mmol), following the procedure described for Example 19. LCMS (2 min, formic) Rt 1.30 min, m/z (ES+) 445 (M+H).

$^1$H NMR (600 MHz, METHANOL-d$_4$) δ ppm 8.46 (s, 2H), 7.96 (d, 2H), 7.14 (d, 2H), 5.00 (s, 2H), 3.95 (d, 2H), 2.52 (q, 2H), 2.40 (s, 3H), 2.20 (s, 3H), 2.04-2.15 (m, 1H), 1.14 (t, 3H), 0.86 (d, 6H).

Example 22

4-((3,5-dimethylisoxazol-4-yl)methoxy)-N-isobutyl-N-(5-methylpyridin-2-yl)benzenesulfonamide

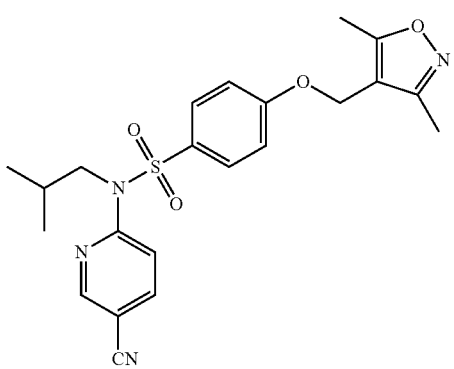 [SMILES: Cc1noc(C)c1COc1ccc(S(=O)(=O)N(CC(C)C)c2ccc(C#N)cn2)cc1]

To a solution of N-(5-cyano-2-pyridinyl)-4-{[(3,5-dimethyl-4-isoxazolyl)methyl]oxy}benzenesulfonamide (23 mg, 0.060 mmol) in acetonitrile (0.5 mL) at room temperature was added N"-(1,1-dimethylethyl)-N,N,N',N'-tetramethylguanidine (0.024 mL, 0.120 mmol). The reaction mixture was stirred at 20° C. for 1 hour, then 1-bromo-2-methylpropane (0.013 mL, 0.120 mmol) was added. The reaction was heated by microwaves to 150° C. for 30 minutes. After cooling, the reaction mixture was diluted with methanol and passed through an aminopropyl (NH$_2$) solid phase extraction (SPE) cartridge followed by a sulphonic acid (SCX) SPE cartridge, eluting with methanol. The appropriate fractions were combined and evaporated under a stream of nitrogen to give the crude product. The crude was purified by mass directed autoprep (formic acid modifier), to provide the title compound (1.8 mg). LCMS (2 min, formic) Rt 1.25 min, m/z (ES$^+$) 441 (M+H).

$^1$H NMR (400 MHz, METHANOL-d$_4$) δ ppm 8.62 (dd, 1H), 8.10 (dd, 1H), 7.80 (dd, 1H), 7.50-7.66 (m, 2H), 6.95-7.15 (m, 2H), 4.95 (s, 2H), 3.75 (d, 2H), 2.40 (s, 3H), 2.24 (s, 3H), 1.75 (m, 1H), 0.89 (d, 6H).

Example 23

N-(3,5-dimethylpyridin-2-yl)-N-isobutyl-4-((tetrahydro-2H-pyran-4-yl)methoxy)benzenesulfonamide

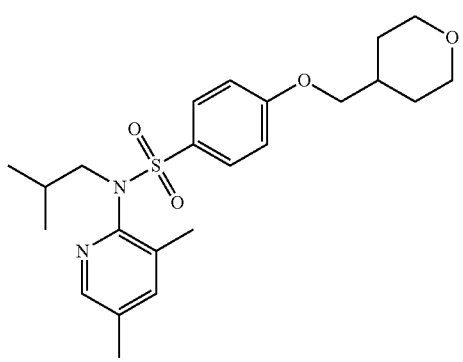 [SMILES: Cc1cnc(N(CC(C)C)S(=O)(=O)c2ccc(OCC3CCOCC3)cc2)c(C)c1]

To a solution of N-(3,5-dimethylpyridin-2-yl)-4-fluoro-N-isobutylbenzenesulfonamide (53.7 mg, 0.160 mmol) and (tetrahydro-2H-pyran-4-yl)methanol (18.54 mg, 0.160 mmol) in dimethyl sulfoxide (DMSO) (1 mL) stirred at room temperature, was added sodium hydride (4.79 mg, 0.160 mmol, 60% wt in mineral oil). The reaction mixture was stirred at 20° C. for 2 hour, then left to stand overnight. Additional sodium hydride (4.79 mg, 0.160 mmol, 60% wt in mineral oil) was added and the reaction stirred for a further 2 hours. The reaction was quenched with methanol (0.5 mL) and water (0.5 mL), then concentrated in vacuo. The crude was purified by mass directed autoprep (formic acid modifier) to give the title compound (31.3 mg). LCMS (2 min, formic) Rt 1.38 min, m/z (ES$^+$) 433 (M+H).

$^1$H NMR (400 MHz, CHLOROFORM-d) δ ppm 8.01 (d, 1H), 7.51-7.67 (m, 2H), 7.45 (d, 1H), 6.83-7.00 (m, 2H), 4.03 (dd, 2H), 3.86 (d, 2H), 3.46 (td, 2H), 3.29 (d, 2H), 2.55 (s, 3H), 2.31 (s, 3H), 1.99-2.18 (m, 1H), 1.76 (dd, 2H), 1.38-1.58 (m, 3H), 0.88 (br. s., 6H).

Example 24

4-((3,5-dimethylisoxazol-4-yl)methoxy)-N-(3-ethyl-6-methylpyridin-2-yl)-N-isobutylbenzenesulfonamide

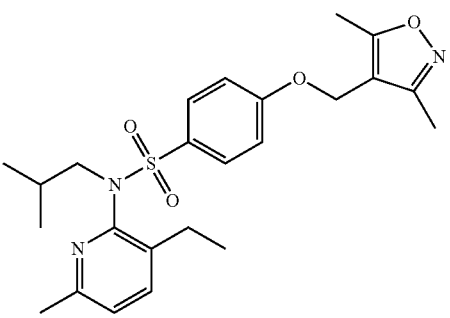 [SMILES: CCc1ccc(C)nc1N(CC(C)C)S(=O)(=O)c1ccc(OCc2c(C)noc2C)cc1]

The title compound (24.3 mg) was prepared from 4-((3,5-dimethylisoxazol-4-yl)methoxy)-N-(3-ethyl-6-methylpyridin-2-yl)benzenesulfonamide (60.2 mg, 0.150 mmol), following the procedure described for Example 22. LCMS (2 min, formic) Rt 1.42 min, m/z (ES$^+$) 458 (M+H).

$^1$H NMR (400 MHz, DMSO-d$_6$) δ ppm 7.73 (d, 1H), 7.47-7.57 (m, 2H), 7.21 (d, 1H), 7.13-7.19 (m, 2H), 5.04 (s, 2H), 3.21 (br. s., 2H), 2.84 (q, 2H), 2.43 (s, 3H), 2.26 (s, 3H), 2.23 (s, 3H), 1.36 (m, 1H), 1.21 (t, 3H), 0.82 (br. s., 6H).

Example 25

4-{[(3,5-dimethyl-4-isoxazolyl)methyl]oxy}-N-[6-(methyloxy)-2-pyridinyl]-N-(2-methylpropyl)benzenesulfonamide

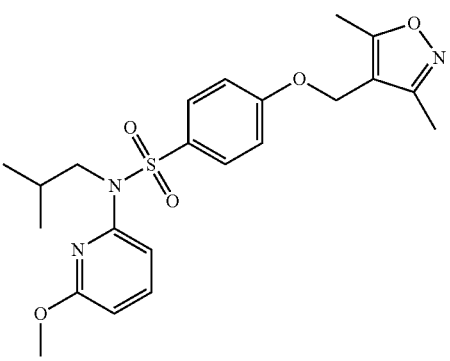 [SMILES: COc1cccc(N(CC(C)C)S(=O)(=O)c2ccc(OCc3c(C)noc3C)cc2)n1]

A solution of (4-{[(3,5-dimethyl-4-isoxazolyl)methyl]oxy}benzenesulfonyl chloride) (69.6 mg, 0.231 mmol) and 6-(methyloxy)-N-(2-methylpropyl)-2-pyridinamine (37.8 mg, 0.210 mmol) was prepared in pyridine (1 mL) and left to stand overnight. The mixture was concentrated and purified by mass directed autoprep (formic acid modifier), to give the title compound (28.0 mg). LCMS (2 min, formic) Rt 1.31 min, m/z (ES$^+$) 446 (M+H).

$^1$H NMR (400 MHz, DMSO-d$_6$) δ ppm 7.75 (t, 1H), 7.49-7.62 (m, 2H), 7.11-7.23 (m, 2H), 7.08 (d, 1H), 6.69 (d, 1H), 5.01 (s, 2H), 3.56 (s, 3H), 3.50 (d, 2H), 2.40 (s, 3H), 2.20 (s, 3H), 1.57 (m, 1H), 0.85 (d, 6H).

Example 26

N-isobutyl-N-(6-methoxypyridin-2-yl)-4-(pyridin-4-ylmethoxy)benzenesulfonamide

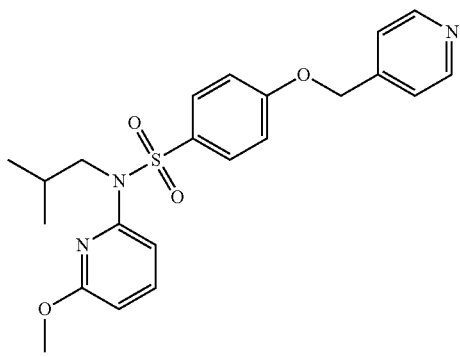 [SMILES: COc1cccc(N(CC(C)C)S(=O)(=O)c2ccc(OCc3ccncc3)cc2)n1]

Pyridin-4-ylmethanol (20.22 mg, 0.185 mmol) and 4-fluoro-N-isobutyl-N-(6-methoxypyridin-2-yl)benzenesulfonamide (62.7 mg, 0.185 mmol) were dissolved in N,N-dimethylformamide (DMF) (3 mL) and sodium hydride (7.41 mg, 0.185 mmol, 60% wt in mineral oil) added. Reaction left to stir at room temperature, under nitrogen, for 3 hours. The reaction was then quenched by adding water (2 mL). The mixture was concentrated in vacuo and the product extracted to the organic phase of an aqueous work up between ethyl acetate and water. The organic phase was dried by passing it through a hydrophobic frit, concentrated and then purified by mass directed autoprep (formic acid modifier), to give the title compound (21.2 mg). LCMS (2 min, formic) Rt 1.05 min, m/z (ES$^+$) 428 (M+H).

$^1$H NMR (400 MHz, DMSO-d$_6$) δ ppm 8.50-8.65 (m, 2H), 7.75 (t, 1H), 7.50-7.58 (m, 2H), 7.42 (d, 2H), 7.12-7.20 (m, 2H), 7.06 (d, 1H), 6.68 (d, 1H), 5.27 (s, 2H), 3.48 (d, 2H), 3.32 (s, 3H), 1.55 (m, 1H), 0.84 (d, 6H).

Example 27

4-{[(3,5-dimethyl-4-isoxazolyl)methyl]oxy}-N-(4,6-dimethyl-3-pyridinyl)-N-(2-methylpropyl)benzenesulfonamide

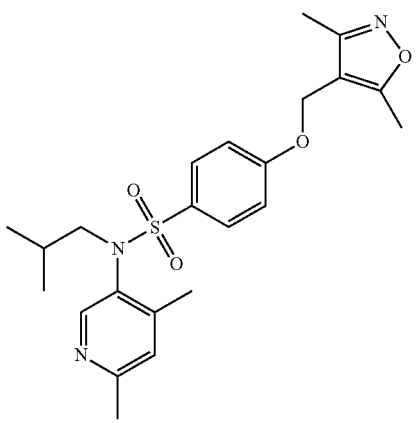 [SMILES: Cc1cc(C)c(N(CC(C)C)S(=O)(=O)c2ccc(OCc3c(C)noc3C)cc2)cn1]

4-{[(3,5-dimethyl-4-isoxazolyl)methyl]oxy}-N-(4,6-dimethyl-3-pyridinyl)benzenesulfonamide (100 mg, 0.258 mmol) and 2-(tert-butyl)-1,1,3,3-tetramethylguanidine (44.2 mg, 0.258 mmol) were dissolved in acetonitrile (1 mL). The mixture was stirred at room temperature for 1 hour, then 1-bromo-2-methylpropane (0.028 mL, 0.258 mmol) was added. The reaction was stirred at room temperature for 20 hours, then additional 2-(tert-butyl)-1,1,3,3-tetramethylguanidine (44.2 mg, 0.258 mmol) and 1-bromo-2-methylpropane (0.028 mL, 0.258 mmol) were added. The reaction was heated to 60° C. and stirred for a further 2 hours. The solvent was removed in vacuo and the residue was partitioned between water (5 mL) and dichloromethane (5 mL). The organic layer was separated, concentrated and purified by mass directed autoprep (formic acid modifier). The required fractions were combined and concentrated to provide the title compound (17 mg) as a colourless oil. LCMS (2 min, formic) Rt 1.04 mins, m/z (ES$^+$) 444 (M+H).

Example 28

4-((3,5-dimethylisoxazol-4-yl)methoxy)-N-(3,6-dimethylpyrazin-2-yl)-N-isobutylbenzenesulfonamide

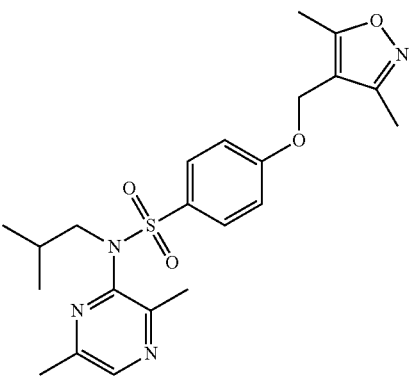 [SMILES: Cc1cnc(C)c(N(CC(C)C)S(=O)(=O)c2ccc(OCc3c(C)noc3C)cc2)n1]

The title compound (3.1 mg) was prepared from 4-((3,5-dimethylisoxazol-4-yl)methoxy)-N-(3,6-dimethylpyrazin-2-yl)benzenesulfonamide (44 mg, 0.11 mmol) following the procedure described for Example 1. LCMS (2 min, formic) Rt 1.22 min, m/z (ES$^+$) 445 (M+H). $^1$H NMR (400 MHz, METHANOL-d$_4$) δ ppm 8.31 (s, 1H), 7.53 (d, 2H), 7.13 (d, 2H), 5.01 (s, 2H), 2.70 (s, 3H), 2.43 (s, 3H), 2.35 (s, 3H), 2.27 (s, 3H), 1.38-1.46 (m, 1H), 1.27-1.35 (m, 1H), 0.90-0.96 (m, 1H), 0.88 (s, 3H), 0.86 (s, 3H).

Example 29

4-((3,5-dimethylisoxazol-4-yl)methoxy)-N-isobutyl-N-(4-methylpyrimidin-5-yl)benzenesulfonamide

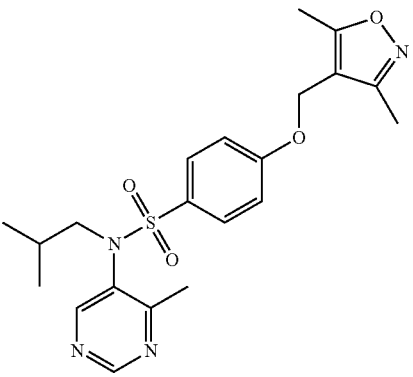 [SMILES: Cc1ncncc1N(CC(C)C)S(=O)(=O)c1ccc(OCc2c(C)noc2C)cc1]

The title compound (47 mg) was prepared from 4-((3,5-dimethylisoxazol-4-yl)methoxy)-N-(4-methylpyrimidin-5-yl)benzenesulfonamide (187 mg, 0.5 mmol) following the procedure described for Example 3. LCMS (3 min, High pH) Rt 1.59 min, m/z (ES$^+$) 431 (M+H).

$^1$H NMR (600 MHz, DMSO-d$_6$) δ ppm 8.99 (s, 1H), 8.17 (s, 1H), 7.58 (d, 2H), 7.22 (d, 2H), 5.04 (br. s., 2H), 3.44-3.52

(m, 1H), 3.24-3.34 (m, 1H), 2.43 (s, 3H), 2.42 (s, 3H), 2.22 (s, 3H), 1.41-1.50 (m, 1H), 0.92 (d, 3H), 0.79 (d, 3H).

Example 30

4-((3,5-dimethylisoxazol-4-yl)methoxy)-N-isobutyl-N-(2-methyl-6-(pyrrolidin-3-yl)pyridin-3-yl)benzenesulfonamide

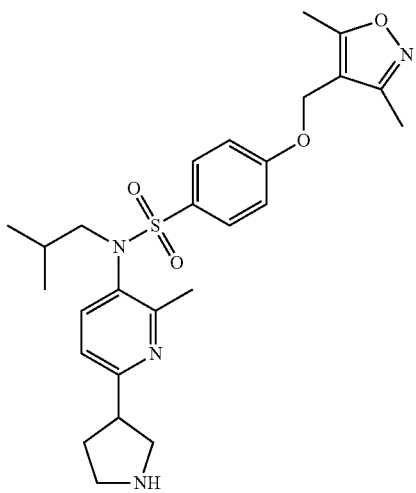 [SMILES: Cc1nc(C2CCNC2)ccc1N(CC(C)C)S(=O)(=O)c1ccc(OCc2c(C)noc2C)cc1]

To a solution of 4-{[(3,5-dimethyl-4-isoxazolyl)methyl]oxy}-N-{2-methyl-6-[1-(phenylmethyl)-3-pyrrolidinyl]-3-pyridinyl}-N-(2-methylpropyl)benzenesulfonamide (114 mg, 0.194 mmol) in acetonitrile (3 mL) was added 1-chloroethyl chloroformate (0.027 mL, 0.252 mmol) and the reaction mixture was heated at reflux under nitrogen for 2 hours. To this was added methanol (3 mL) and the reaction mixture was refluxed under nitrogen for 1 hour. The solvent was removed in vacuo. The sample was then purified by mass directed autoprep (formic acid buffered) to give the required product as formic acid salt (33 mg). LCMS (2 min, formic) Rt 0.86 min, m/z (ES$^+$) 499 (M+H).

$^1$H NMR (400 MHz, CHLOROFORM-d) δ ppm 8.55 (br. s., 1H), 7.60 (t, 2H), 6.95-7.07 (m, 3H), 4.87 (s, 2H), 3.35-3.64 (m, 5H), 3.10 (td, 1H), 2.50 (d, 3H), 2.45 (s, 3H), 2.42 (dd, 2H), 2.32 (s, 3H), 2.10-2.24 (m, 2H), 1.50-1.60 (m, 1H), 1.01 (d, 3H), 0.86 (t, 3H).

Example 31

N-isobutyl-N-(5-isopropyl-3-methylpyridin-2-yl)-4-((tetrahydro-2H-pyran-4-yl)methoxy)benzenesulfonamide

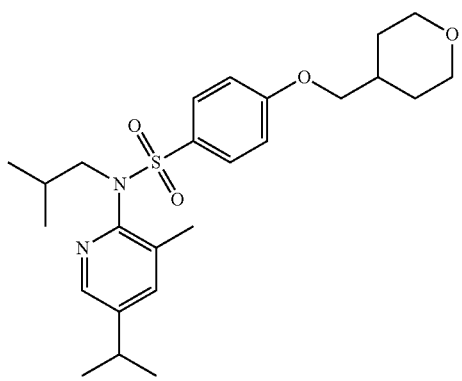 [SMILES: Cc1cc(C(C)C)cnc1N(CC(C)C)S(=O)(=O)c1ccc(OCC2CCOCC2)cc1]

N-isobutyl-N-(3-methyl-5-(prop-1-en-2-yl)pyridin-2-yl)-4-((tetrahydro-2H-pyran-4-yl)methoxy)benzenesulfonamide (83 mg, 0.18 mmol) was dissolved in ethyl acetate (3 mL) and methanol (3 mL). The reaction was hydrogenated using an H-cube flow hydrogenator (settings: room temperature, 1 bar, 1 mL/min flow rate) and a 10% Pd/C CatCart as the catalyst. Two clean fractions of product were collected along with a third impure fraction, the impure fraction was then purified by mass directed autoprep (formic acid modifier). The two clean product fractions and purified third fraction were then combined and evaporated to give the title compound (61 mg). LCMS (2 min, formic) Rt 1.45 min, m/z (ES$^+$) 461 (M+H).

$^1$H NMR (400 MHz, DMSO-d$_6$) δ ppm 8.12 (d, 1H), 7.68 (d, 1H), 7.61-7.43 (m, 2H), 7.17-6.99 (m, 2H), 4.00-3.79 (m, 4H), 3.40-3.31 (m, 2H), 3.24-3.14 (m, 2H), 2.99-2.87 (m, 1H), 2.44 (s, 3H), 2.10-1.97 (m, 1H), 1.74-1.64 (m, 2H), 1.42-1.19 (m, 9H), 0.80 (br. s., 6H).

Example 32

N-isobutyl-N-(3-methyl-5-(prop-1-en-2-yl)pyridin-2-yl)-4-((tetrahydro-2H-pyran yl)methoxy)benzenesulfonamide

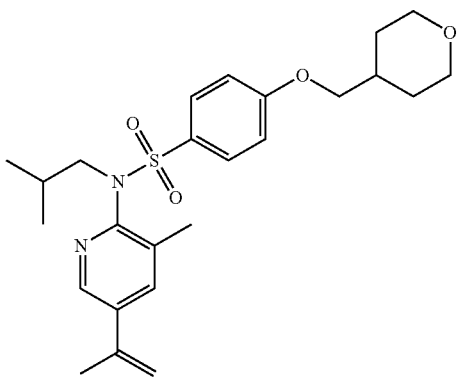 [SMILES: C=C(C)c1cnc(N(CC(C)C)S(=O)(=O)c2ccc(OCC3CCOCC3)cc2)c(C)c1]

N-(5-chloro-3-methylpyridin-2-yl)-N-isobutyl-4-((tetrahydro-2H-pyran-4-yl)methoxy)benzenesulfonamide (140 mg, 0.31 mmol), potassium trifluoro(prop-1-en-2-yl)borate (69 mg, 464 μmol) and Buchwald's Suzuki-Miyaura cross-coupling pre-catalyst (prepared according to ref. *J. Am. Chem. Soc.* 2010, 132, 14073) (5 mg, 6.18 μmol) were dissolved in anhydrous THF (1 mL). To this solution was added degassed potassium phosphate (0.5 M aqueous) (2 mL, 1.0 mmol) then the reaction vessel sealed and heated by microwaves to 110° C. for 30 minutes. The reaction was cooled, combined with a previous identical trial reaction on a smaller (0.06 mmol) scale and concentrated in vacuo. The crude product was then extracted to the organic phase of an aqueous work up between ethyl acetate and water. The organic phase was passed through a hydrophobic frit, concentrated in vacuo, then purified by mass directed autoprep (formic acid modifier) to give the title compound 85% purity (87 mg). LCMS (2 min, formic) Rt 1.44 min, m/z (ES$^+$) 459 (M+H).

$^1$H NMR (400 MHz, DMSO-d$_6$) δ ppm 8.39 (d, 1H), 7.91 (d, 1H), 7.52 (d, 2H), 7.09 (d, 2H), 5.57 (s, 1H), 5.23 (s, 1H), 3.94 (d, 2H), 3.89 (dd, 2H), 3.34 (td, 2H), 3.24 (d, 2H), 2.48

(s, 3H), 2.13 (s, 3H), 1.96-2.08 (m, 1H), 1.68 (d, 2H), 1.27-1.42 (m, 3H), 0.82 (br. s., 6H).

Example 33

N-isobutyl-N-(5-isopropylpyridin-2-yl)-4-((tetrahydro-2H-pyran-4-yl)methoxy)benzenesulfonamide

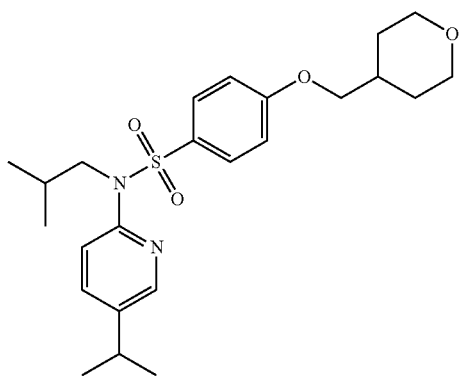 [SMILES: CC(C)CN(c1ccc(C(C)C)cn1)S(=O)(=O)c1ccc(OCC2CCOCC2)cc1]

4-fluoro-N-isobutyl-N-(5-isopropylpyridin-2-yl)benzenesulfonamide (30 mg, 0.086 mmol) was dissolved in N,N-dimethylformamide (DMF) (3 mL) and to this solution was added (tetrahydro-2H-pyran-4-yl)methanol (12 mg, 0.10 mmol) and sodium hydride (2 mg, 0.10 mmol, 60% wt in mineral oil). The reaction was stirred under nitrogen for 2 hours at room temperature. The reaction was quenched then concentrated in vacuo and the crude product extracted to the organic phase of an aqueous work up between ethyl acetate and water. The organic phase was passed through a hydrophobic frit, concentrated in vacuo and purified by mass directed autoprep (formic acid modifier) to give the title compound (17 mg). LCMS (2 min, formic) Rt 1.41 min, m/z (ES$^+$) 447 (M+H).

$^1$H NMR (400 MHz, DMSO-d$_6$) δ ppm 8.24 (d, 1H), 7.78 (dd, 1H), 7.52-7.35 (m, 3H), 7.13-6.94 (m, 2H), 3.96-3.79 (m, 4H), 3.44 (d, 2H), 3.38-3.31 (m, 2H), 3.00-2.88 (m, 1H), 2.09-1.93 (m, 1H), 1.71-1.62 (m, 2H), 1.53-1.40 (m, 1H), 1.40-1.26 (m, 2H), 1.22 (d, 6H), 0.80 (d, 6H).

Example 34

N-(5-chloro-3-methylpyridin-2-yl)-N-isobutyl-4-((tetrahydro-2H-pyran-4-yl)methoxy)benzenesulfonamide

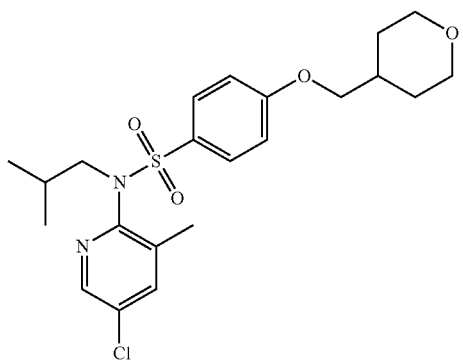 [SMILES: Cc1cc(Cl)cnc1N(CC(C)C)S(=O)(=O)c1ccc(OCC2CCOCC2)cc1]

N-(5-chloro-3-methylpyridin-2-yl)-4-fluoro-N-isobutyl-benzenesulfonamide (200.5 mg, 0.562 mmol) was dissolved in dimethyl sulfoxide DMSO (2 mL) and to this solution was added (tetrahydro-2H-pyran-4-yl)methanol (98 mg, 0.84 mmol) and sodium hydride (33 mg, 0.84 mmol, 60% wt in mineral oil). The reaction was left to stir overnight at room temperature, under nitrogen. The reaction was concentrated under a stream of nitrogen, then the crude product was extracted to the organic phase of an aqueous work up between ethyl acetate and water. The organic phase was passed through a hydrophobic frit and concentrated in vacuo to give the title compound (224 mg). LCMS (2 min, formic) Rt 1.42 min, m/z (ES$^+$) 453 (M+H).

$^1$H NMR (400 MHz, CHLOROFORM-d) δ ppm 8.14 (d, 1H), 7.64 (d, 1H), 7.59-7.47 (m, 2H), 7.01-6.84 (m, 2H), 4.09-3.96 (m, 2H), 3.87 (d, 2H), 3.56-3.34 (m, 3H), 3.28 (d, 2H), 2.59 (s, 3H), 2.17-2.03 (m, 1H), 1.83-1.70 (m, 2H), 1.52-1.42 (m, 2H), 0.88 (br. s., 6H).

Example 35

4-((cis-3-fluoropiperidin-4-yl)methoxy)-N-isobutyl-N-(5-isopropyl-3-methylpyridin-2-yl)benzenesulfonamide

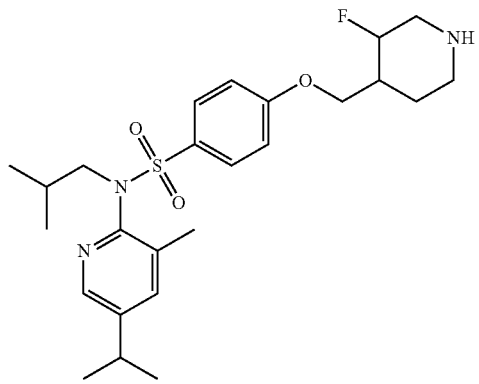 [SMILES: Cc1cc(C(C)C)cnc1N(CC(C)C)S(=O)(=O)c1ccc(OCC2CCNCC2F)cc1]

tert-Butyl cis-3-fluoro-4-((4-(N-isobutyl-N-(5-isopropyl-3-methylpyridin-2-yl)sulfamoyl)phenoxy)methyl)piperidine-1-carboxylate (53 mg, 0.09 mmol) was dissolved in trifluoroacetic acid (TFA) (1 mL) and dichloromethane (DCM) (1 mL) and stirred under nitrogen, at room temperature for 30 minutes. The reaction was concentrated under a stream of nitrogen, then purified by mass directed autoprep (ammonium carbonate modifier) to give the title compound (22 mg). LCMS (2 min, formic) Rt 1.06 min, m/z (ES$^+$) 478 (M+H).

$^1$H NMR (400 MHz, CHLOROFORM-d) δ ppm 8.12-8.00 (m, 1H), 7.59 (d, 2H), 7.53-7.39 (m, 1H), 6.95 (d, 2H), 4.92-4.67 (m, 1H), 4.10 (t, 1H), 3.88 (dd, 1H), 3.46-3.09 (m, 4H), 3.00-2.80 (m, 2H), 2.80-2.64 (m, 2H), 2.57 (s, 3H), 2.32-1.99 (m, 1H), 1.72-1.39 (m, 2H), 1.29 (d, 6H), 0.89 (br. s., 6H).

Example 36

4-((cis-3-fluoropiperidin-4-yl)methoxy)-N-isobutyl-N-(5-isopropylpyridin-2-yl)benzenesulfonamide

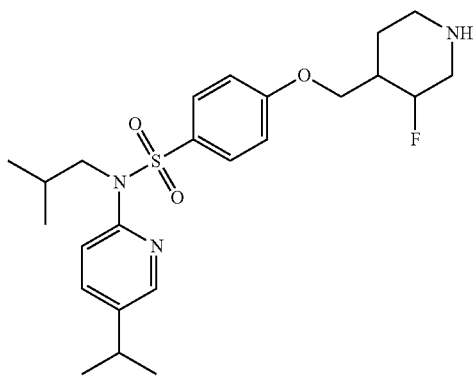 [SMILES: CC(C)CN(c1ccc(C(C)C)cn1)S(=O)(=O)c1ccc(OCC2CCNCC2F)cc1]

The title compound (20 mg) was prepared from tert-butyl cis-3-fluoro-4-((4-(N-isobutyl-N-(5-isopropylpyridin-2-yl)sulfamoyl)phenoxy)methyl)piperidine-1-carboxylate (47 mg, 0.084 mmol) following the procedure described for Example 35. LCMS (2 min, formic) Rt 1.00 min, m/z (ES$^+$) 464 (M+H).

$^1$H NMR (400 MHz, DMSO-d$_6$) δ ppm 8.25 (d, 1H), 7.83-7.74 (m, 1H), 7.53-7.34 (m, 3H), 7.07 (d, 2H), 4.85-4.57 (m, 1H), 4.02 (s, 1H), 3.97-3.82 (m, 1H), 3.44 (d, 2H), 3.19-3.02 (m, 1H), 3.00-2.82 (m, 2H), 2.24-1.96 (m, 2H), 1.55-1.33 (m, 4H), 1.22 (d, 6H), 0.80 (d, 6H).

Example 37

4-((3,5-dimethylisoxazol-4-yl)methoxy)-N-isopentyl-N-(5-isopropylpyridin-2-yl)benzenesulfonamide

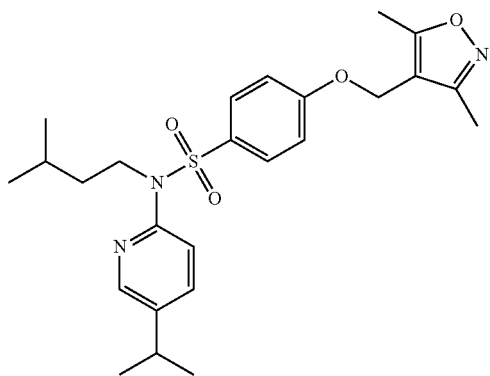 [SMILES: Cc1noc(C)c1COc1ccc(S(=O)(=O)N(CCC(C)C)c2ccc(C(C)C)cn2)cc1]

To a stirred solution of 4-((3,5-dimethylisoxazol-4-yl)methoxy)-N-(5-isopropylpyridin-2-yl)benzenesulfonamide (150 mg, 0.37 mmol) in acetonitrile (4 mL) was added 2-(tert-butyl)-1,1,3,3-tetramethylguanidine (128 mg, 0.75 mmol). The reaction mixture was stirred at 20° C. for 1 hour. 1-Bromo-3-methylbutane (0.09 mL, 0.75 mmol) was then added and the reaction vessel sealed and heated by microwaves to 150° C. for 30 minutes. The reaction mixture was concentrated in vacuo and diluted with ethyl acetate. The organic phase was washed with water, dried using a hydrophobic frit and evaporated in vacuo to give the crude product. The crude was then purified by flash silica (Si) chromatography (0-25% ethyl acetate-cyclohexane gradient). The appropriate fractions were combined and evaporated in vacuo to give the title compound (48 mg) as a yellow oil. LCMS (2 min, HpH) Rt 1.50 min, m/z (ES$^+$) 472 (M+H).

$^1$H NMR (400 MHz, METHANOL-d$_4$) δ ppm 8.18 (d, 1H), 7.78-7.67 (m, 1H), 7.52 (d, 2H), 7.42 (d, 1H), 7.07 (d, 2H), 4.96 (s, 2H), 3.72 (t, 2H), 3.07-2.81 (m, 1H), 2.41 (s, 3H), 2.25 (s, 3H), 1.75-1.48 (m, 1H), 1.36-1.16 (m, 8H), 0.90-0.74 (m, 6H).

Example 38

N-(5-isopropylpyridin-2-yl)-N-(3-methylbutan-2-yl)-4-((tetrahydro-2H-pyran-4-yl)methoxy)benzenesulfonamide

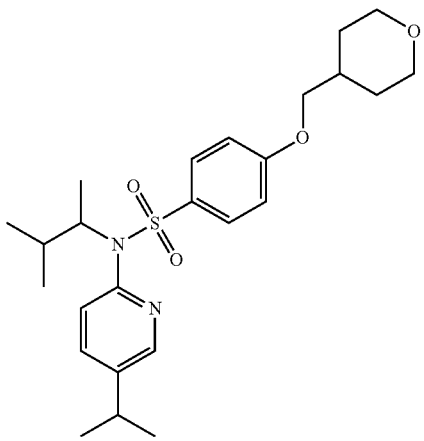 [SMILES: CC(C)c1ccc(N(C(C)C(C)C)S(=O)(=O)c2ccc(OCC3CCOCC3)cc2)nc1]

To a solution of (tetrahydro-2H-pyran-4-yl)methanol (10.20 mg, 0.088 mmol) and 4-fluoro-N-(5-isopropylpyridin-2-yl)-N-(3-methylbutan-2-yl)benzenesulfonamide (32 mg, 0.088 mmol) in dimethyl sulfoxide (DMSO) (1 mL) stirred in air at room temperature was added sodium hydride (3.51 mg, 0.088 mmol, 60% wt in mineral oil). The reaction mixture was stirred at 20° C. for 2 hours. Additional (tetrahydro-2H-pyran-4-yl)methanol (10.20 mg, 0.088 mmol) and sodium hydride (3.51 mg, 0.088 mmol, 60% wt in mineral oil) were added and the reaction mixture stirred overnight. The reaction was carefully quenched with isopropanol (1 mL) and water (1 mL). The solvent was evaporated in vacuo and the residue partitioned between water (5 mL) and dichloromethane (2×5 mL), then separated using a hydrophobic frit. The solvent was removed in vacuo and the crude was purified by mass directed autoprep (formic acid modifier) to give the title product (32 mg). LCMS (2 min, formic) Rt 1.41 min, m/z (ES$^+$) 461 (M+H).

$^1$H NMR (400 MHz, METHANOL-d$_4$) δ ppm 8.29-8.35 (m, 1H) 7.77 (d, 2H) 7.63-7.72 (m, 1H) 7.22 (d, 1H) 7.03 (d, 2H) 3.88-4.03 (m, 4H) 3.77 (dd, 1H) 3.46 (td, 2H) 2.91-3.04 (m, 1H) 2.02-2.15 (m, 1H) 1.76 (dd, 2H) 1.36-1.57 (m, 3H) 1.22-1.33 (m, 6H) 1.05-1.14 (m, 3H) 0.96 (d, 3H) 0.79 (d, 3H).

Example 39

N-isobutyl-N-(5-isopropyl-3-methoxypyridin-2-yl)-4-((tetrahydro-2H-pyran-4-yl)methoxy)benzenesulfonamide

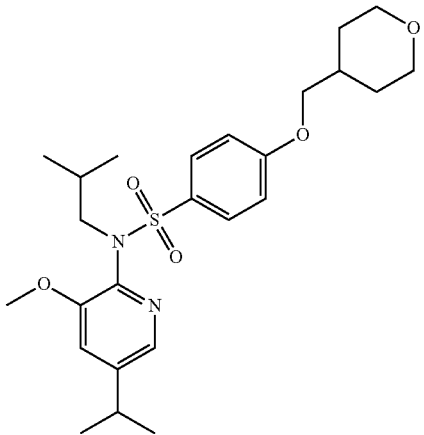 [SMILES: COc1cc(C(C)C)cnc1N(CC(C)C)S(=O)(=O)c1ccc(OCC2CCOCC2)cc1]

To a solution of (tetrahydro-2H-pyran-4-yl)methanol (14.29 mg, 0.123 mmol) and 4-fluoro-N-isobutyl-N-(5-isopropyl-3-methoxypyridin-2-yl)benzenesulfonamide (46.8 mg, 0.123 mmol) in dimethyl sulfoxide (DMSO) (200 μL) stirred in air at room temperature was added sodium hydride (4.92 mg, 0.123 mmol, 60% wt in mineral oil). The reaction mixture was stirred for 4 days then carefully quenched with isopropanol (1 mL) and evaporated in vacuo. The crude sample was purified by mass directed autoprep (formic acid modifier) to give the title product, 42.9 mg. LCMS (2 min, formic) Rt 1.36 min, m/z (ES$^+$) 477 (M+H).

$^1$H NMR (400 MHz, METHANOL-d$_4$) δ ppm 7.91 (d, 1H) 7.73 (d, 2H) 7.39 (d, 1H) 7.08 (d, 2H) 3.92-4.05 (m, 4H) 3.84 (s, 3H) 3.43-3.55 (m, 2H) 3.31 (d, 2H) 3.03 (dt, 1H) 2.06-2.19 (m, 1H) 1.80 (dd, 2H) 1.37-1.56 (m, 3H) 1.34 (d, 6H) 0.84 (d, 6H).

Example 40

N-(2-cyclopropylpyrimidin-5-yl)-4-((3,5-dimethylisoxazol-4-yl)methoxy)-N-isobutylbenzenesulfonamide

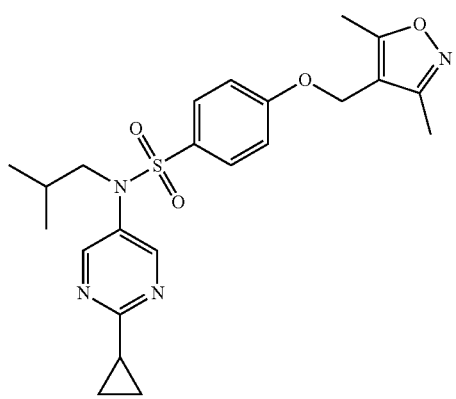 [SMILES: Cc1noc(C)c1COc1ccc(S(=O)(=O)N(CC(C)C)c2cnc(C3CC3)nc2)cc1]

To a solution of N-(2-cyclopropylpyrimidin-5-yl)-4-((3,5-dimethylisoxazol-4-yl)methoxy)benzenesulfonamide (74 mg, 0.185 mmol) in acetonitrile (0.1 mL) stirred at room temperature, was added 2-(tert-butyl)-1,1,3,3-tetramethylguanidine (0.074 mL, 0.370 mmol). The mixture was stirred at room temperature for 1 hour, then 1-bromo-2-methylpropane (0.04 mL, 0.370 mmol) added. The reaction was then heated by microwaves to 150° C., for 30 minutes. After cooling the reaction was diluted with acetonitrile (0.5 mL) and water (0.5 mL) and the crude sample purified by mass directed autoprep (formic acid modifier) to give the title product (43.75 mg). LCMS (2 min, High pH) Rt 1.27 min, m/z (ES$^+$) 457 (M+H).

$^1$H NMR (400 MHz, METHANOL-d$_4$) δ ppm 8.30 (s, 2H) 7.48-7.57 (m, 2H) 7.16 (s, 2H) 4.99 (s, 2H) 3.38 (d, 2H) 2.42 (s, 3H) 2.24-2.29 (m, 3H) 2.16-2.25 (m, 1H) 1.55 (m, 1H) 1.04-1.13 (m, 4H) 0.90 (d, 6H).

Example 41

N-(5-isopropylpyridin-2-yl)-N-(oxetan-3-ylmethyl)-4-((tetrahydro-2H-pyran-4-yl)methoxy)benzenesulfonamide

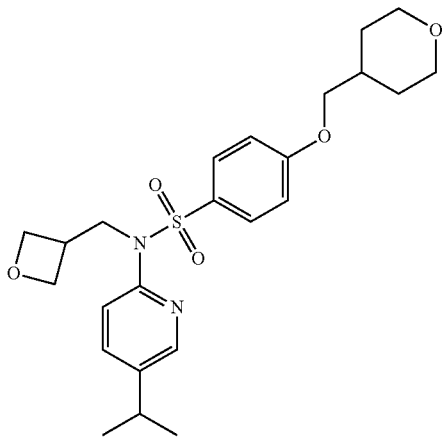 [SMILES: CC(C)c1ccc(N(CC2COC2)S(=O)(=O)c2ccc(OCC3CCOCC3)cc2)nc1]

To a solution of (tetrahydro-2H-pyran-4-yl)methanol (20.08 mg, 0.173 mmol) and 4-fluoro-N-(5-isopropylpyridin-2-yl)-N-(oxetan-3-ylmethyl)benzenesulfonamide (63 mg, 0.173 mmol) in dimethyl sulfoxide (DMSO) (1 mL) stirred in air at room temperature was added sodium hydride (6.91 mg, 0.173 mmol, 60% wt in mineral oil). The reaction mixture was stirred at 20° C. for 2 hours. The reaction mixture was carefully quenched with methanol (2 mL) and water (2 mL), then solvents evaporated in vacuo. The crude product was purified by flash silica (Si) (25% ethyl acetate-cyclohexane gradient) to give the title product (63.2 mg). LCMS (2 min, High pH) Rt 1.23 min, m/z (ES$^+$) 461 (M+H).

$^1$H NMR (400 MHz, METHANOL-d$_4$) δ ppm 8.18 (d, 1H) 7.69 (s, 1H) 7.47-7.54 (m, 2H) 7.40 (d, 1H) 7.00 (d, 2H) 4.61 (dd, 2H) 4.35 (t, 2H) 3.84-4.07 (m, 6H) 3.40-3.50 (m, 2H) 2.86-3.08 (m, 2H) 1.99-2.14 (m, 1H) 1.74 (d, 2H) 1.35-1.51 (m, 2H) 1.26 (d, 6H).

Example 42

4-{[(3,5-dimethyl-4-isoxazolyl)methyl]oxy}-N-(2-methylpropyl)-N-[2-(trifluoromethyl)-4-pyrimidinyl]benzenesulfonamide

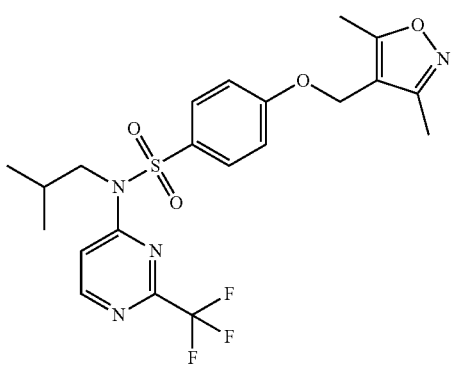 [SMILES: Cc1noc(C)c1COc1ccc(S(=O)(=O)N(CC(C)C)c2ccnc(C(F)(F)F)n2)cc1]

To a solution of N-(2-methylpropyl)-2-(trifluoromethyl)-4-pyrimidinamine (100 mg, 0.456 mmol) and 4-{[(3,5-dimethyl-4-isoxazolyl)methyl]oxy}benzenesulfonyl chloride (151 mg, 0.502 mmol) in pyridine (1 mL) was added 2-(tert-butyl)-1,1,3,3-tetramethylguanidine (0.092 mL, 0.456 mmol). The reaction vessel was sealed and heated by microwaves to 100° C. for 30 minutes. The solvent was evaporated in vacuo to give the crude product, which was purified by solid phase extraction (SPE) using an aminopropyl (NH$_2$) cartridge then a sulphonic acid (SCX) cartridge (both eluted with methanol). The appropriate fractions were combined and dried under a stream of nitrogen to give the crude product which was further purified by mass directed autoprep (formic acid modifier) to give the title product, 19.8 mg. LCMS (2 min, formic) Rt 1.32 min, m/z (ES$^+$) 485 (M+H).

Example 43

4-((3,5-dimethylisoxazol-4-yl)methoxy)-N-isobutyl-N-(pyrazin-2-yl)benzenesulfonamide

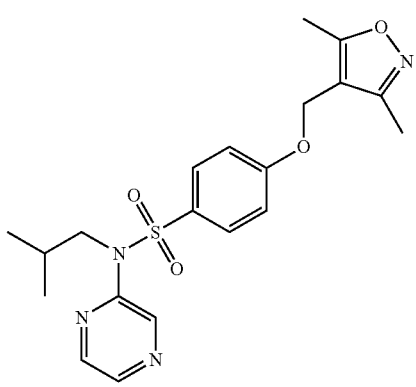 [SMILES: Cc1noc(C)c1COc1ccc(S(=O)(=O)N(CC(C)C)c2cnccn2)cc1]

The title compound (208 mg) was prepared from 4-((3,5-dimethylisoxazol-4-yl)methoxy)-N-(pyrazin-2-yl)benzenesulfonamide (180 mg, 0.5 mmol) following the procedure described for Example 3. LCMS (3 min, High pH) Rt 1.72 min, m/z (ES$^+$) 417 (M+H).

Example 44

4-((3,5-dimethylisoxazol-4-yl)methoxy)-N-isobutyl-N-(pyrimidin-5-yl)benzenesulfonamide

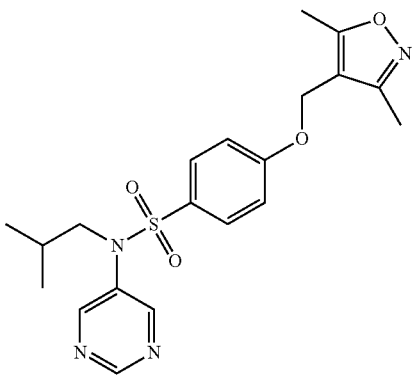 [SMILES: Cc1noc(C)c1COc1ccc(S(=O)(=O)N(CC(C)C)c2cncnc2)cc1]

The title compound (44.2 mg) was prepared from 4-((3,5-dimethylisoxazol-4-yl)methoxy)-N-(pyrimidin-5-yl)benzenesulfonamide (180 mg, 0.5 mmol) following the procedure described for Example 3. LCMS (3 min, High pH) Rt 1.56 min, m/z (ES$^+$) 417 (M+H).

Example 45

4-((3,5-dimethylisoxazol-4-yl)methoxy)-N-isobutyl-N-(2-methylpyrimidin-5-yl)benzenesulfonamide

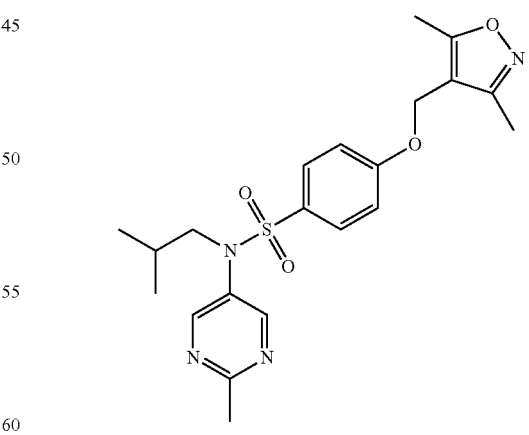

The title compound (99 mg) was prepared from 4-((3,5-dimethylisoxazol-4-yl)methoxy)-N-(2-methylpyrimidin-5-yl)benzenesulfonamide (187 mg, 0.5 mmol) following the procedure described for Example 3. LCMS (3 min, High pH) Rt 1.59 min, m/z (ES$^+$) 431 (M+H).

Example 46

4-((3,5-dimethylisoxazol-4-yl)methoxy)-N-isobutyl-N-(5-methylpyridin-3-yl)benzenesulfonamide

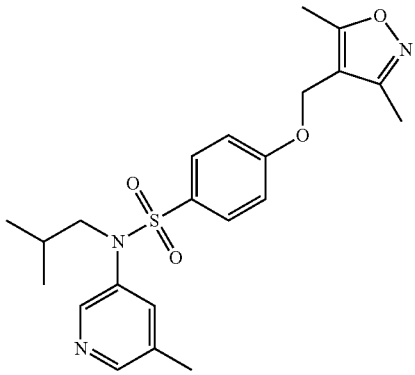 [SMILES: Cc1cncc(N(CC(C)C)S(=O)(=O)c2ccc(OCc3c(C)noc3C)cc2)c1]

The title compound (75.3 mg) was prepared from 4-((3,5-dimethylisoxazol-4-yl)methoxy)-N-(5-methylpyridin-3-yl)benzenesulfonamide (187 mg, 0.5 mmol) following the procedure described for Example 3. LCMS (3 min, High pH) Rt 1.68 min, m/z (ES$^+$) 430 (M+H).

Example 47

N-(cyclobutylmethyl)-4-((3,5-dimethylisoxazol-4-yl)methoxy)-N-(5-isopropylpyridin-2-yl)benzenesulfonamide

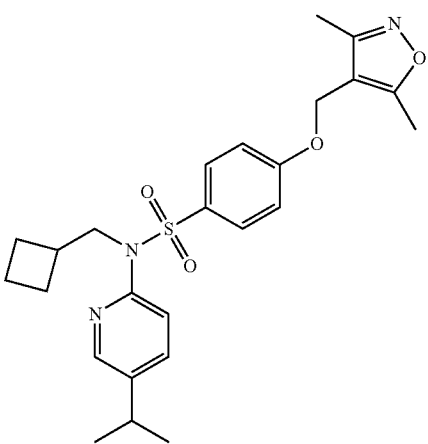 [SMILES: Cc1noc(C)c1COc1ccc(S(=O)(=O)N(CC2CCC2)c2ccc(C(C)C)cn2)cc1]

To a solution of 4-((3,5-dimethylisoxazol-4-yl)methoxy)-N-(5-isopropylpyridin-2-yl)benzenesulfonamide (150 mg, 0.374 mmol) in acetonitrile (4 mL) stirred in air at 20° C., was added 2-(tert-butyl)-1,1,3,3-tetramethylguanidine (128 mg, 0.747 mmol). The reaction mixture was stirred at 20° C. for 1 hour, then (bromomethyl)cyclobutane (0.084 ml, 0.747 mmol) was added. The reaction was heated by microwaves to 150° C. for 30 minutes. After cooling the solvent was removed in vacuo and the residue was dissolved in ethyl acetate. The organic phase was washed with water (5 mL) and dried using a hydrophobic frit. The solvent was removed in vacuo to give the crude product as an orange oil. The crude product was purified by flash silica (Si) chromatography (0-25% ethyl acetate-cyclohexane gradient). The appropriate fractions were combined and evaporated in vacuo to give the title product (42 mg) as a colourless oil. LCMS (2 min, High pH) Rt 1.48 mins, m/z (ES$^+$) 470, (M+H).

Example 48

N-(6-cyclopropylpyridazin-3-yl)-4-((3,5-dimethylisoxazol-4-yl)methoxy)-N-isobutylbenzenesulfonamide

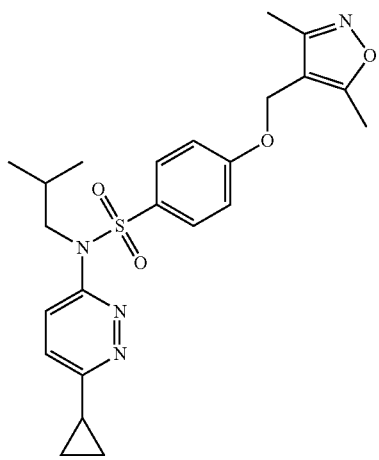 [SMILES: Cc1noc(C)c1COc1ccc(S(=O)(=O)N(CC(C)C)c2ccc(C3CC3)nn2)cc1]

To a solution of N-(6-cyclopropylpyridazin-3-yl)-4-((3,5-dimethylisoxazol-4-yl)methoxy)benzenesulfonamide (51 mg, 0.127 mmol) in acetonitrile (0.1 mL) stirred at room temperature, was added 2-(tert-butyl)-1,1,3,3-tetramethylguanidine (0.051 mL, 0.255 mmol). The mixture was stirred at room temperature for 1 hour, then 1-bromo-2-methylpropane (0.028 mL, 0.255 mmol) added. The reaction was then heated by microwaves to 150° C., for 30 minutes. After cooling the solvent was removed under a stream of nitrogen and the crude sample purified by mass directed autoprep (formic acid modifier) to give the title product (2.8 mg). LCMS (2 min, formic) Rt 1.21 min, m/z (ES$^+$) 457 (M+H).

Example 49

4-((3,5-dimethylisoxazol-4-yl)methoxy)-N-(5-isopropylpyridin-2-yl)-N-(2-methylbutyl)benzenesulfonamide

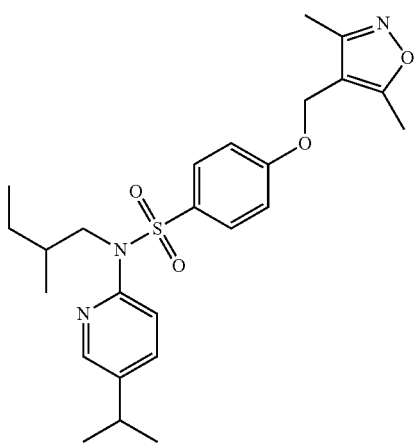 [SMILES: CCC(C)CN(c1ccc(C(C)C)cn1)S(=O)(=O)c1ccc(OCc2c(C)noc2C)cc1]

To a solution of 4-((3,5-dimethylisoxazol-4-yl)methoxy)-N-(5-isopropylpyridin-2-yl)benzenesulfonamide (156 mg, 0.389 mmol) in acetonitrile (4 mL) stirred in air at 20° C., was added 2-(tert-butyl)-1,1,3,3-tetramethylguanidine (133 mg, 0.777 mmol). The reaction mixture was stirred at 20° C. for 1 hour, then 1-bromo-2-methylbutane (117 mg, 0.777 mmol) was added. The reaction then heated by microwaves to 150°

C., for 30 minutes. After cooling the solvent was removed in vacuo and diluted with ethyl acetate. The organic phase was washed with water (5 mL), then dried using a hydrophobic frit. The solvent was removed in vacuo to give the crude product as an orange oil. Purification of the crude was attempted using flash silica (Si) chromatography (0-25% ethylacetate-cyclohexane gradient) followed by mass directed autoprep (ammonium carbonate modifier), however impurities still remained. A final purification using a silica (Si) cartridge (eluting with a gradient of 0-25% ethyl acetate-cyclohexane) provided a small amount of clean product (8.5 mg) as a colourless oil. LCMS (2 min, High pH) Rt 1.48 mins, m/z (ES+) 472 (M+H).

Example 50

4-(1-hydroxy-2-morpholinoethyl)-N-isobutyl-N-(5-isopropylpyridin-2-yl)benzenesulfonamide

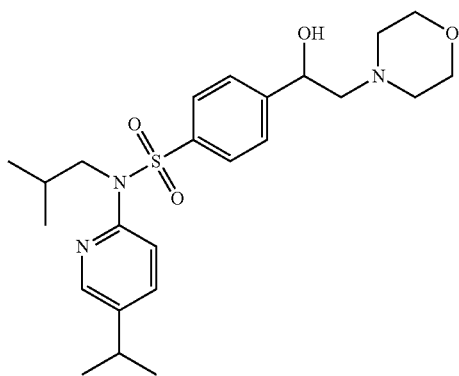 [SMILES: CC(C)CN(c1ccc(C(C)C)cn1)S(=O)(=O)c1ccc(C(O)CN2CCOCC2)cc1]

To a solution of 2-(4-(1-hydroxy-2-morpholinoethyl)-N-isobutylphenylsulfonamido)-5-isopropylpyridine 1-oxide (130 mg, 0.272 mmol) in ethanol (1 mL) at 20° C. was added molybdenum hexacarbonyl (71.9 mg, 0.272 mmol). The reaction vessel was sealed and heated by microwaves to 150° C. for 1 hour. After cooling, the reaction was filtered and evaporated in vacuo to give the crude product. The crude was purified by mass directed autoprep (ammonium carbonate modifier) but gave impure product. The sample was repurified by mass directed autoprep (formic acid modifier) to give the title product, 34.1 mg. LCMS (2 min, formic) Rt 0.85 min, m/z (ES+) 462 (M+H).

Example 51

4-(1-hydroxy-2-((3-methyloxetan-3-yl)amino)ethyl)-N-isobutyl-N-(5-isopropylpyridin-2-yl)benzenesulfonamide

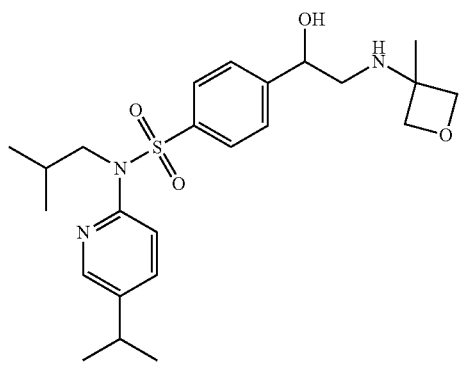 [SMILES: CC(C)CN(c1ccc(C(C)C)cn1)S(=O)(=O)c1ccc(C(O)CNC2(C)COC2)cc1]

To a solution of 2-(4-(1-hydroxy-2-((3-methyloxetan-3-yl)amino)ethyl)-N-isobutylphenylsulfonamido)-5-isopropylpyridine 1-oxide (71.9 mg, 0.151 mmol), in ethanol (1 mL) stirred in air at 20° C., was added molybdenum hexacarbonyl (39.7 mg, 0.151 mmol). The reaction was heated by microwaves to 100° C. for 10 minutes. After cooling, the reaction mixture was filtered and solids washed with ethanol (5 mL) and dichloromethane (5 mL). The combined filtrate was evaporated in vacuo and the crude sample purified by mass directed autoprep (ammonium carbonate modifier). The relevant fractions were concentrated under a stream of nitrogen to give the title product, 7.5 mg. LCMS (2 min, formic) Rt 0.91 min, m/z (ES+) 462 (M+H).

Analytical Methodology

Purification

Purification was by a range of methods including: mass-directed autoprep (MDAP) using either low or high pH modifiers see below for column details; automated normal phase chromatography on for example a Biotage Flashmaster II or a ISCO companion, using silica or aminopropyl column and a range of solvents, which included, for example, ethyl acetate/cyclohexane/dichloromethane and methanol; or recrystallisation from suitable solvent.

MDAP Purification

MDAP (Formic Acid Modifier):

The HPLC analysis was conducted on a Sunfire C18 column (150 mm×30 mm i.d. 5 µm packing diameter) at ambient temperature.

The solvents employed were:
A=0.1% v/v solution of Formic Acid in Water.
B=0.1% v/v solution of Formic Acid in Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP (High pH):

The HPLC analysis was conducted on an XBridge C18 column (150 mm×30 mm i.d. 5 µm packing diameter) at ambient temperature.

The solvents employed were:
A=10 mM Ammonium Bicarbonate in water adjusted to pH 10 with Ammonia solution.
B=Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

MDAP (TFA Modifier):

The HPLC analysis was conducted on a Sunfire C18 column (150 mm×30 mm i.d. 5 µm packing diameter) at ambient temperature.

The solvents employed were:
A=0.1% v/v solution of Trifluoroacetic Acid in Water.
B=0.1% v/v solution of Trifluoroacetic Acid in Acetonitrile.

The gradient was selected according to the analytical retention time.

The UV detection was an averaged signal from wavelength of 210 nm to 350 nm and mass spectra were recorded on a mass spectrometer using positive electrospray ionisation.

LCMS Analysis Conditions

The following conditions are representative of those used for the generation of analytical LCMS data.

Formic Acid LC/MS (2 Minute Method)

UPLC analysis was conducted on an Acquity UPLC BEH C18 column (2.1 mm×50 mm i.d. 1.7 µm packing diameter) at 40° C.

The solvents employed were:
A=0.1% v/v solution of formic acid in water.
B=0.1% v/v solution of formic acid in acetonitrile.
The gradient employed was:

| Time (min) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

High dH LC/MS (2 Minute Method)

UPLC analysis was conducted on an Acquity UPLC BEH C18 column (50 mm×2.1 mm i.d. 1.7 µm packing diameter) at 40° C.

The solvents employed were:
A=10 mM ammonium bicarbonate in water adjusted to pH 10 with ammonia solution.
B=Acetonitrile.
The gradient employed was:

| Time (min) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was a summed signal from wavelength of 210 nm to 350 nm and mass spectra were recorded on a mass spectrometer, such as a Waters ZQ, using alternate-scan positive and negative mode electrospray ionization.

High pH LC/MS (3 Minute Method)

UPLC analysis was conducted on an Acquity UPLC BEH C18 column (30 mm×2.1 mm i.d. 1.7 µm packing diameter) at 30° C.

The solvents employed were:
A=10 mM ammonium bicarbonate in water adjusted to pH 10 with ammonia solution.
B=Acetonitrile.
The gradient employed was:

| Time (min) | Flow Rate (mL/min) | % A | % B |
|---|---|---|---|
| 0 | 0.8 | 99 | 1 |
| 2.5 | 0.8 | 5 | 95 |
| 2.9 | 0.8 | 5 | 95 |
| 3.0 | 0.8 | 99 | 1 |

The UV detection was a summed signal from wavelength of 210 nm to 350 nm and mass spectra were recorded on a mass spectrometer, such as a Waters ZQ, using alternate-scan positive and negative mode electrospray ionization.

$^1$H NMR Analysis $^1$H NMR spectra were recorded on a Bruker DRX 400 (400 MHz) instrument. The following abbreviations have been used: s, singlet; d, doublet; t, triplet; Hz, Hertz.

Biological Evaluation

The compounds of formula (I) and pharmaceutically acceptable salts thereof are RORγ modulators, and hence have utility in the treatment of inflammatory, metabolic and autoimmune diseases mediated by RORγ. The biological activities of exemplified compounds of formula (I) were assessed in the following disclosed assays.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL (SEQ ID NO:1) motifs in the co-activator SRC 1(2) sequences. Short peptide sequences containing the LXXLL (SEQ ID NO:1) motif mimic the behavior of full-length co-activator.

This assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, Thus, it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in E. coli strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) (SEQ ID NO:2) was fused in frame to residues 263-518 of the human RORγ sequence.

Protein Purification

Approximately 50 g E. coli cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (InVitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mLs. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (8000×)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient room temperature. The modified RORγ-LBD was dialyzed against 2 buffer changes—TBS pH 8.0 containing 5 mM DTT, 2 mM EDTA and 2% sucrose—each at least 20 times the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five.

A biotinylated peptide corresponding to amino acid 676 to 700 (CPSSHSSLTERHKILHRLLQEGSPS) (SEQ ID NO:3) of the co-activator steroid receptor coactivator SRC1(2) was generated using similar method.

Assay

Protocol Step 1

Preparation of Europium Labeled SRC1(2) Peptide

Biotinylated SRC1(2) solution was prepared by adding an appropriate amount of biotinylated SRC1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Protocol Step 2

Preparation of APC Labeled RORγ-LBD

Biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Protocol Step 3

Testing

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for 1 hour and then read on ViewLux in Lance mode for EU/APC.

Results

All exemplified compounds of formula (I), with the exception of Example 14, were found to have a mean pIC50 between 5.0 and 8.0. Example 14 had a mean pIC50 of <5.0. Examples 2, 15, 24, 31-34, 38, 47 and 49 were found to have a mean pIC50 value of ≥7.5.

Peripheral Blood Mononucleocyte Cell Assay (PBMC Assay—IL-17)

RORs (Retinoic Acid Related Orphan Receptors) are members of the class 1 nuclear receptor family. RORs regulate gene transcription by binding to specific DNA response element (RORE) as a monomer and have critical roles of in development, immunity, circadian rhythm, and cellular metabolism (recently reviewed by A. Jetten, *Nuclear Receptor Signaling* 2009, 7, 1-32). One member of this nuclear receptor family, RORγt, has been identified as a regulator of differentiation and development of IL-17 expressing human and mouse CD4+ T cells, so called Th17 cells which play a role in both host defense and inflammatory disorders. RORγt is also required for transcription of the genes encoding IL-17A and IL-17F in iNKT, NKT (*Mucosal Immunol.* 2009, 2(5), 383-392; *J. Immunol.* 2008, 180, 5167-5171), γδ T cells (*Am. J. Respir. Crit. Care Med.* 2010, 182, 464-476), CD8+ T cells (*J. Leukocyte Biol.* 2007, 82, 354-360) and finally CD4− CD8TCRαβ+ T cells (*J. Immunol.* 2008, 181, 8761-8766). Additional immune cells such as eosinophils, neutrophils and macrophages can also be a source of IL-17A in allergic inflammation related to asthma (*J. Allergy Clin. Immunol.* 2001, 108, 430-438; *J. Immunol.* 2008, 181, 6117-6124; *Immunity* 2004, 21, 467-476), however, the link with RORγt has not yet been confirmed in the literature.

This assay is designed to measure levels of IL-17A secreted from antiCD3/CD28 stimulated frozen Peripheral Blood Mononuclear cells (PBMC) isolated from human blood with the aim of identifying inhibitors of IL-17A release.

Assay Solutions

Assay Media Components:

RPMI 1640 (as supplied, for example, by Gibco)—90%

FCS (as supplied, for example, by Invitrogen) (endotoxin tested)—10%

Penicillyn/Streptomycin solution ×1

Preparation: 50 mL Heat Inactivated Australian FBS, 5 mL Glutamax and 5 mL Penicillin/Streptomycin are aseptically added to 500 mL RPMI in a biosafety cabinet. The Penicillin/Streptomycin 100× stock is supplied by, for example, Gibco (10,000 Units/mL Penicillin, 10,000 ug/mL Streptomycin). Stock L-glutamine 100× (as supplied, for example, by Invitrogen)

Note: To be kept in a fridge (4° C.) for 4 weeks. Warm up in a water bath set at 37° C. prior to use.

Anti-Human IL-17 Detection Antibody Components:

IL-17 detection antibody and Blocking buffer B (supplied, for example, by Mesoscale Discovery) Dulbecco's PBS without $Ca^{2+}$ and $Mg^{2+}$ (supplied, for example, by Gibco)

Note: Prepare detection anti body at final concentration of 1 ug/mL. Solution to be kept refrigerated.

MSD Read Buffer T×2 Components:

Water and MSD Read Buffer T×4 (as supplied, for example, by MSD)

Note: Dilute MSD Read Buffer T×4 in half with water. To be kept at room temperature.

Assay Capacity: 384

Equipment and Materials

MSD Sector Imager 6000 supplied by MesoScale Discovery (MSD)

Multidrop 384 supplied by Thermo Scientific

CyBi-Well, model 7518-00 supplied by CyBio AG

Microplates 384 clear supplied by Greiner

Assay

Protocol Step 1

Assay Plates Preparation Before Adding Cell Suspension

1. Ensure no external endotoxin is present in media and reagents used in the assay.

2. The compounds for screening are dispensed into a master plate at 10 mM top concentration which are serially diluted 1:3 across 11 points in DMSO, then 500 nl is transferred into a 384-well flat-bottomed Greiner plate to which 50 ul of cell suspension is added: for the single shot screening the highest concentration of compound is $10^{-5}$ M; for 11 point full curve dose response studies the highest concentration is $10^{-4}$ M.

Controls:

As a low control, DMSO (as supplied, for example, by VWR) (final concentration 1%) in column 6 (16 points).

As a high control, 5-(4-fluorophenyl)-2-ureidothiophene-3-carboxamide (obtainable from, for example, Sigma) at a final concentration of $10^{-4}$ M in DMSO should be used in column 18 (16 points).

If the compounds dispensed earlier than the day of the assay, they should be kept at −20° C.

Protocol Step 2

Day 1: Thawing and Handing of PBMC

1. Thaw PBMC in the vial using water bath (37° C.). Ensure that water does not cover the vial (the level should be lower than the screw cup of the vial)
2. Transfer the contents of the vial into 50 mL Falcon tube.
3. Add 10 mL of Assay Media drop by drop to decrease the concentration of DMSO (as supplied, for example, by VWR) in the freezing media gradually.
4. Spin down the cells in a centrifuge (1000 rpm-5 mins).
5. Decant the supernatant.
6. Re-suspend the cells in 10 mL of Assay Media.
7. Transfer of 0.1 mL of suspension into Cedex counting tube.
8. Add 0.9 mL of media to achieve volume of the suspension for counting up to 1 mL. Count the cells on Cedex using 1:10 dilution factor settings.
9. Make the cell suspension at the concentration $8 \times 10^5$ cells/mL. to give a final number of 40,000 cells/well.

Protocol Step 3

Day 1: Stimulation of PBMC with CD3/CD28 Beads

1. Add well mixed CD3/CD28 Dynabeads (as supplied, for example, by Dynal) to achieve ratio bead:cell=2:1 (i.e a dilution of 1 in 20). Mix thoroughly.
2. Dispense the suspension into the 384 Assay Plates using Multidrop (50 ul per well). If the volume of cell suspension is large, mix the suspension after dispensing into every other plate.
3. Cover the plates with the lids and place them to the humidified incubator (37° C., 5% $CO_2$) for 48 hours.

Protocol Step 4

Day 2: MSD Plates Preparation

1. Block cytokine capture Mesoscale Discovery MSD plates with 0.1% Block buffer B (provided by Mesoscale Discovery) in D-PBS solution using 40 ul per well.
2. Leave the plates covered with lids in the fridge over night.
3 Plates are washed manually using PBS and a multidrop combi. Blocker B buffer is flicked out into a waste pot and 40 ul of PBS is dispensed into the plate using a combi. This is then flicked out manually and the plates tapped on to blue roll to remove as much residual liquid as possible before transferring the cell supernatant.
4 Tap the plates over a paper towel.

Protocol Step 5

Day 3: IL-17 Detection on MSD Plates

1. Transfer 10 ul of supernatants from assay plates to the MSD plates using Cybiwell. Ensure that all wells are covered with the solution. Tap the plate gently, if some of the wells are not covered with the supernatant.
2. Cover the plates with adhesive foil (brown stickers) and leave them for 1 hour of incubation on shaker at room temperature (RT).
3. Add 10 ul of MSD IL-17 detecting antibody using multidrop (1 ug/mL in D-PBS without $Ca^{2+}$ and $Mg^{2+}$ (supplied, for example, by Gibco)).
4. Cover the plates with adhesive foil and incubated with shaking for 3 hours at room temperature
5. Plates are washed manually twice using PBS and a multidrop combi as before.
6. Tap the plates over a paper towel.
7. Add 35 ul of MSD Read Buffer T×2 using multidrop.
8. Read plates on MSD MA6000 reader using the 384 well plate protocol as per manufacturer's instructions.

Results

All exemplified compounds of formula (I), with the exception of Examples 29, 32, 34, 37, 40, 41, 44-49, and 51 that were not tested, were found to have a mean pIC50 between 4.0 and 8.0. Examples 2, 15-17, 24, 35 and 38 were found to have a mean pIC50 value of 6.0.

Utility

Compounds of formula (I), and pharmaceutically acceptable salts thereof, are modulators of RORγ and can be useful in the treatment of inflammatory, metabolic and autoimmune diseases mediated by RORγ such as asthma, chronic obstructive pulmonary disease (COPD) and bronchitis, allergic diseases, such as allergic rhinitis and atopic dermatitis, cystic fibrosis, lung allograph rejection, multiple sclerosis, rheumatoid arthritis, juvenile Rheumatoid arthritis, Osteoarthritis, ankylosing spondylitis, systemic lupus erythematosus, psoriasis, Hashimoto's disease, pancreatisis, autoimmune diabetes, autoimmune ocular disease, ulcerative colitis, Crohn's disease, inflammatory bowel disease (IBS), inflammatory bowel syndrome (IBD), Sjorgen's syndrome, optic neuritis, type I diabetes, neuromyelitis optica, Myastehnia Gravis, uveitis, Guillain-Barre syndrome, psoriatic arthritis, Graves' disease and scleritis. The use of RORγ modulators for the treatment of the respiratory diseases listed above, such as asthma and COPD is of particular interest.

In a further aspect, the present invention also provides a compound of formula (I), or a pharmaceutically acceptable salt or solvate thereof, for use in therapy.

In a further aspect, the present invention also provides a compound of formula (I), or a pharmaceutically acceptable salt or solvate thereof, for use in the treatment of inflammatory, metabolic and autoimmune diseases mediated by RORγ.

In a further aspect, the present invention provides a compound of formula (I), or a pharmaceutically acceptable salt thereof, for use in the treatment of asthma or chronic obstructive pulmonary disease.

In a further aspect, the present invention is directed to a method of treatment of an inflammatory, metabolic or autoimmune disease mediated by RORγ, which comprises administering to a subject in need thereof, a safe and therapeutically effective amount of a compound of formula (I), or a pharmaceutically acceptable salt thereof.

In yet a further aspect, the present invention is directed to a method of treating chronic obstructive pulmonary disease or asthma, which comprises administering to a subject in need thereof, a safe and therapeutically effective amount of a compound of formula (I), or a pharmaceutically acceptable salt thereof.

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "therapeutically effective amount" refers to the quantity of a compound of formula (I), or a pharmaceutically acceptable salt thereof, which will elicit the desired biological response in an animal or human body.

As used herein, the term "subject" refers to an animal or human body

Pharmaceutical Development

A compound of formula (I), or a pharmaceutically acceptable salt thereof, will normally, but not necessarily, be formulated into pharmaceutical compositions prior to administration to a patient. Accordingly, in another aspect the invention is directed to pharmaceutical compositions comprising a compound of formula (I), or a pharmaceutically acceptable salt thereof, and one or more pharmaceutically-acceptable excipients.

Pharmaceutical compositions comprising a compound of formula (I), or a pharmaceutically acceptable salt thereof, may be prepared using techniques and methods known to those skilled in the art. Some of the methods commonly used in the art are described in Remington's Pharmaceutical Sciences (Mack Publishing Company).

A pharmaceutical composition of a compound of formula (I), or a pharmaceutically acceptable salt thereof, may be formulated for administration by any appropriate route, for example by the inhaled, nasal, oral (including buccal or sublingual), topical (including buccal, sublingual, transdermal, epicutaneous) or parenteral (subcutaneous, intramuscular, intravenous, intradermal) route. Thus, a pharmaceutical composition of a compound of formula (I), or a pharmaceutically acceptable salt thereof, may be formulated as, for example, a solution or suspension (aqueous or non-aqueous), tablet, capsule, powder, granule, lozenge, lotion, cream, ointment, gel, foam or reconstitutable powder depending on the particular route of administration. Such pharmaceutical compositions may be prepared by any method known in the art of pharmacy, for example by bringing into association the active ingredient with the excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl yl)-hydroxybenzoate or sorbic acid, and, if desired, conventional flavouring or colouring agents.

Pharmaceutical compositions of a compound of formula (I) or a pharmaceutically acceptable salt thereof, for topical administration, may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The compositions may also contain compatible conventional carriers, such as cream or ointment bases and ethanol or oleyl alcohol for lotions. Such carriers may be present as from about 1% up to about 98% of the composition. More usually they will form up to about 80% of the composition.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions for topical administration to the lung may include aerosol compositions and dry powder compositions.

Dry powder compositions for topical delivery to the lungs or nose generally contain a powder mix of a compound of formula (I) or a pharmaceutically acceptable salt thereof and a suitable carrier, such as lactose or starch. Dry powder compositions for topical delivery to the lung or nose may, for example, be presented in capsules and cartridges for use in an inhaler or insufflator of, for example, gelatine. Each capsule or cartridge may generally contain between 20 µg-10 mg of the compound of formula (I), or a pharmaceutically acceptable salt thereof. Alternatively, the compounds of formula (I), or pharmaceutically acceptable salts thereof, may be presented without excipients. Packaging of the pharmaceutical composition may be suitable for unit dose or multi-dose delivery. In the case of multi-dose delivery, the composition can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable composition comprising a compound of formula (I), or a pharmaceutically acceptable salt thereof, preferably combined with a carrier, such as lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of compound of formula (I), or a pharmaceutically acceptable salt thereof, may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I), or a pharmaceutically acceptable salt thereof, as medicament in a liquid solvent with a flowing liquid antisolvent for said medicament (eg as described in International Patent Application PCT/GB99/04368). Alternatively, the particles may be prepared by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04237). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Aerosol compositions may be developed, with the use of a suitable liquefied propellant, for delivery from pressurised packs, such as a metered dose inhaler. Aerosol compositions can be either a suspension or a solution and generally contain the compound of formula (I), or a pharmaceutically acceptable salt thereof, and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. Aerosol compositions will generally be retained in a pressurised canister (eg an aluminium canister) closed with a valve (eg a metering valve) and fitted into an actuator with a mouthpiece. Aerosol compositions may also include aqueous solutions or suspensions that are delivered to the nose or lungs by nebulisation.

Pharmaceutical compositions for topical administration to the nose may also be developed for delivery by nasal spray or as nasal droplets. Pharmaceutical compositions for nasal administration may be developed in such a way to allow the medicament(s) to be delivered to all appropriate areas of the nasal cavities (the target tissue). Moreover, a pharmaceutical composition may be developed for nasal administration, which permits the medicament(s) to remain in contact with the target tissue for an increased period of time.

A suitable dosing regimen for a pharmaceutical composition administered topically to the nose by use of a nasal spray may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. Typically, each spray to the nostril may deliver from about 25 to about 100 μL of the pharmaceutical composition.

Pharmaceutical compositions for topical administration to the nose by nasal spray or as nasal drops may be prepared as a solution or suspension. The solution or suspension may be aqueous or non-aqueous based, and may contain one or more pharmaceutically acceptable excipients, such as suspending agents, for example carboxymethylcellulose, methylcellulose, veegum, tragacanth, bentonite and polyethylene glycols; preservatives, for example chelating agents (e.g EDTA), quaternary ammonium compounds (e.e benzalkonium chloride, benzethonium chloride, cetrimide and cetylpyridinium chloride), mercurial agents (e.g. phenylmercuric nitrate, phenyl mercuric acetate and thimerosal), alcoholic agents (e.g. chlorobutanol, phenylethyl alcohol and benzyl alcohol), antibacterial esters (e.g. esters of para-hydroxybenzoic acid) and other anti-microbial agents such as chlorhexidine, chlorocresol, sorbic acid and its salts (e.g. potassium sorbate), and polymyxin; isotonicity adjusting agents, for example sodium chloride, dextrose, xylitol and calcium chloride; buffering agents, wetting agents, for example fatty alcohols, esters and ethers, such as polyoxyethylene (20) sorbitan monooleate (polysorbate 80); anti-oxidants, sweetening agents and taste-masking agents.

It should be understood that in addition to the ingredients particularly mentioned above, the pharmaceutical compositions may include other agents conventional in the art having regard to the type of formulation in question.

A compound of formula (I), or a pharmaceutically acceptable salt thereof, may also be used in combination with one or more other therapeutic agents, selected from the group consisting of $\beta_2$-adrenoreceptor agonists, anti-inflammatory agents (e.g. corticosteroids and NSAID's) and anticholinergic agents.

$\beta_2$-adrenoreceptor agonists that may be used in combination with a compound of formula (I), or a pharmaceutically acceptable salt thereof, include, for example, salmeterol, salbutamol, formoterol, and salts thereof, for example the xinafoate salt of salmeterol, the sulfate salt of salbutamol or the fumarate salt of formoterol). Further $\beta_2$-adrenoreceptor agonists include those described in WO03/024439, such as 4-{(1R)-2-[(6-{2-[(2,6-dichlorobenzyl)oxy]ethoxy}hexyl)amino]-1-hydroxyethyl}-2-(hydroxymethyl)phenol and its pharmaceutically acceptable salts, such as triphenylacetate.

Corticosteroids that may be used in combination with a compound of formula (I), or a pharmaceutically acceptable salt thereof, include, for example, fluticasone propionate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

Anticholinergic agents may also be used in combination with a compound of formula (I), or a pharmaceutically acceptable salt thereof. Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Antimuscarinic compounds for administration via inhalation include, for example, ipratropium (for example, as the bromide, CAS 22254-24-6, sold under the name Atrovent), tiotropium (for example, as the bromide, CAS 136310-93-5, sold under the name Spiriva), (3-endo)-3-(2-cyano-2,2-diphenylethyl)-8,8-dimethyl-8-azoniabicyclo[3.2.1]octane bromide, and 4-[hydroxy(diphenyl)methyl]-1-{2-[(phenylmethyl)oxy]ethyl}-1-azoniabicyclo[2.2.2]octane bromide.

It will be clear to a person skilled in the art that, where appropriate, the other therapeutic agent(s) may be used in the form of pharmaceutically acceptable salts, or prodrugs, or as esters (e.g lower alkyl esters), or as solvates (e.g. hydrates) to optimise the activity and/or stability and/or physical characteristics (e.g. solubility) of the therapeutic agent. It will be clear also that, where appropriate, the therapeutic agent(s) may be used in optically pure form.

The invention thus provides in a further aspect a combination comprising a compound of formula (I), or a pharmaceutically acceptable salt thereof, and one or more other therapeutic agents.

The invention claimed is:

1. A compound of formula (I), or a pharmaceutically acceptable salt thereof:

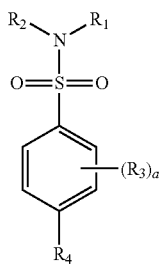

(I)

wherein:
$R_1$ is

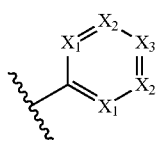

each $X_1$ is independently N or $CR_a$;
each $X_2$ is independently N or $CR_b$;
$X_3$ is N or $CR_c$;
each $R_a$ is independently selected from H, $CF_3$, halo, $C_{1-4}$alkyl and $C_{1-4}$alkoxy;
each $R_b$ is independently selected from H, $CF_3$, halo, $CH_3$ and $OCH_3$;
each $R_c$ is independently selected from H, $C_{1-4}$alkyl, $C_{2-4}$alkenyl, $C_{1-4}$alkoxy, $CF_3$, halo, CN, $C_{3-6}$cycloalkyl and $C_{3-6}$heterocycloalkyl;
$R_2$ is selected from the group consisting of $C_{3-5}$alkyl, —$CH_2C_{3-4}$cycloalkyl, and —$CH_2$oxetanyl;
each $R_3$ is independently selected from the group consisting of $C_{1-3}$alkyl, $C_{1-3}$alkoxy, halo, OH and $CH_2OH$;
$R_4$ is the group —$X(CHR_5)_bR_6$;
X is selected from the group consisting of O, $CH_2$, CHOH and $CHCH_2OH$;
each $R_5$ is independently selected from the group consisting of H, OH and $CH_2OH$;
$R_6$ is isoxazole, tetrahydro-2H-pyran, tetrahydrofuran, —$NHR_7$ or is a 5- or 6-membered heteroaryl group, wherein $R_6$ may be unsubstituted or substituted with one or two substitutents independently selected from halo and $CH_3$;

$R_7$ is oxetanyl or tetrahydrofuran, wherein $R_7$ may be unsubstituted or substituted with one or two substitutents independently selected from halo and $CH_3$;

a is 0, 1 or 2;

b is 0, 1 or 2;

with the proviso that $R_1$ contains one or two nitrogen atoms.

2. The compound according to claim 1, or a pharmaceutically acceptable salt thereof, wherein $R_1$ is selected from the group consisting of:

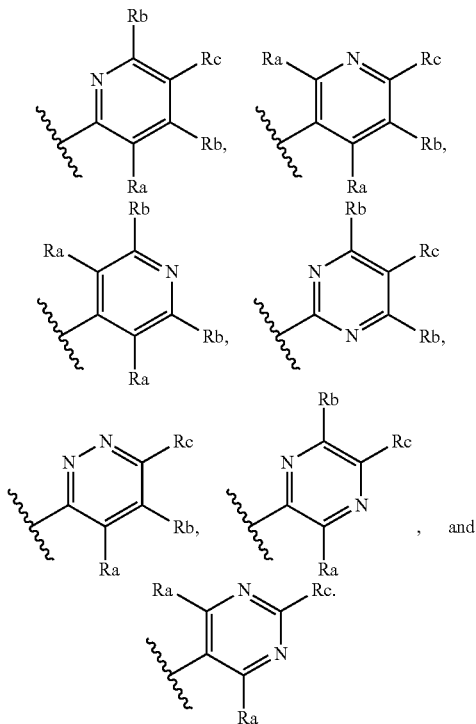

3. The compound according to claim 1, or a pharmaceutically acceptable salt thereof, wherein each Ra represents H, or is independently selected from $CH_3$, $—OCH_3$ and halo.

4. The compound according to claim 1, or a pharmaceutically acceptable salt thereof, wherein each Rb represents H, or is independently selected from $CH_3$, $—OCH_3$ and halo.

5. The compound according to claim 1, or a pharmaceutically acceptable salt thereof, wherein each Rc represents H, or $C_{1-4}$alkyl.

6. The compound according to claim 5, or a pharmaceutically acceptable salt thereof, wherein Rc represents isopropyl.

7. A compound according to claim 1, or a pharmaceutically acceptable salt thereof, wherein $R_2$ is selected from the group consisting of isopropyl, isobutyl, isopentyl and 3-methylbutan-2-yl.

8. The compound according to claim 1, or a pharmaceutically acceptable salt thereof, wherein X is O.

9. The compound according to claim 1, or a pharmaceutically acceptable salt thereof, wherein b is 1 or 2.

10. The compound according to claim 1, or a pharmaceutically acceptable salt thereof, wherein $R_5$ is H.

11. The compound according to claim 1, or a pharmaceutically acceptable salt thereof, wherein $R_6$ is isoxazole, tetrahydro-2H-pyran, or tetrahydrofuran, and further wherein $R_6$ may be unsubstituted or substituted with one or two substituents independently selected from halo and $CH_3$.

12. The compound according to claim 1, or a pharmaceutically acceptable salt thereof, wherein $R_6$ is $—NHR_7$.

13. The compound according to claim 12, or a pharmaceutically acceptable salt thereof, wherein $R_7$ is unsubstituted oxetanyl.

14. The compound according to claim 1, or a pharmaceutically acceptable salt thereof, wherein a is 0 or 1.

15. The compound according to claim 1, or a pharmaceutically acceptable salt thereof, wherein $R_3$ is selected from the group consisting of $CH_3$, $—OCH_3$, halo, OH and $CH_2OH$.

16. A compound according to claim 1, or a pharmaceutically acceptable salt thereof, which is selected from the group consisting of:

4-((3,5-dimethylisoxazol-4-yl)methoxy)-N-(4,6-dimethylpyrimidin-2-yl)-N-isobutylbenzenesulfonamide;

4-((3,5-dimethylisoxazol-4-yl)methoxy)-N-isobutyl-N-(5-isopropylpyridin-2-yl)benzenesulfonamide;

4-((3,5-dimethylisoxazol-4-yl)methoxy)-N-isobutyl-N-(5-methylpyridin-2-yl)benzenesulfonamide;

4-((3,5-dimethylisoxazol-4-yl)methoxy)-N-isobutyl-N-(4-methylpyridin-2-yl)benzenesulfonamide;

4-((3,5-dimethylisoxazol-4-yl)methoxy)-N-isobutyl-N-(6-methylpyridin-2-yl)benzenesulfonamide;

4-((3,5-dimethylisoxazol-4-yl)methoxy)-N-isobutyl-N-(3-methylpyridin-2-yl)benzenesulfonamide;

N-(5-chloropyridin-2-yl)-4-((3,5-dimethylisoxazol-4-yl)methoxy)-N-isobutylbenzenesulfonamide;

4-((3,5-dimethylisoxazol-4-yl)methoxy)-N-(5-fluoropyridin-2-yl)-N-isobutylbenzenesulfonamide;

4-((3,5-dimethylisoxazol-4-yl)methoxy)-N-(2,6-dimethylpyridin-3-yl)-N-isobutylbenzenesulfonamide;

4-((3,5-dimethylisoxazol-4-yl)methoxy)-N-isobutyl-N-(6-methylpyridin-3-yl)benzenesulfonamide;

4-((3,5-dimethylisoxazol-4-yl)methoxy)-N-isobutyl-N-(4-methylpyridin-3-yl)benzenesulfonamide;

4-((3,5-dimethylisoxazol-4-yl)methoxy)-N-(3,5-dimethylpyrazin-2-yl)-N-isobutylbenzenesulfonamide;

4-((3,5-dimethylisoxazol-4-yl)methoxy)-N-isobutyl-N-(2-methylpyridin-4-yl)benzenesulfonamide;

4-{[(3,5-dimethyl-4-isoxazolyl)methyl]oxy}-N-(2-methylpropyl)-N-[4-(trifluoromethyl)-2-pyrimidinyl]benzenesulfonamide;

4-{[(3,5-dimethyl-4-isoxazolyl)methyl]oxy}-N-(3,5-dimethyl-2-pyridinyl)-N-(2-methylpropyl)benzenesulfonamide;

4-{[(3,5-dimethyl-4-isoxazolyl)methyl]oxy}-N-[2-methyl-6-(2-oxo-1,3-oxazolidin-3-yl)-3-pyridinyl]-N-(2-methylpropyl)benzenesulfonamide;

4-{[(3,5-dimethyl-4-isoxazolyl)methyl]oxy}-N-[2-methyl-6-(4-morpholinyl)-3-pyridinyl]-N-(2-methylpropyl)benzenesulfonamide;

2-chloro-N-(3,5-dimethylpyridin-2-yl)-N-isobutyl-4-((tetrahydro-2H-pyran-4-yl)methoxy)benzenesulfonamide;

4-((3,5-dimethylisoxazol-4-yl)methoxy)-N-isobutyl-N-(6-methoxypyridazin-3-yl)benzenesulfonamide;

4-((3,5-dimethylisoxazol-4-yl)methoxy)-N-(6-ethoxypyridazin-3-yl)-N-isobutylbenzenesulfonamide;

4-((3,5-dimethylisoxazol-4-yl)methoxy)-N-(5-ethylpyrimidin-2-yl)-N-isobutylbenzenesulfonamide;

4-((3,5-dimethylisoxazol-4-yl)methoxy)-N-isobutyl-N-(5-methylpyridin-2-yl)benzenesulfonamide;

N-(3,5-dimethylpyridin-2-yl)-N-isobutyl-4-((tetrahydro-2H-pyran-4-yl)methoxy)benzenesulfonamide;

4-((3,5-dimethylisoxazol-4-yl)methoxy)-N-(3-ethyl-6-methylpyridin-2-yl)-N-isobutylbenzenesulfonamide;

4-{[(3,5-dimethyl-4-isoxazolyl)methyl]oxy}-N-[6-(methyloxy)-2-pyridinyl]-N-(2-methylpropyl)benzenesulfonamide;

N-isobutyl-N-(6-methoxypyridin-2-yl)-4-(pyridin-4-ylmethoxy)benzenesulfonamide;

4-{[(3,5-dimethyl-4-isoxazolyl)methyl]oxy}-N-(4,6-dimethyl-3-pyridinyl)-N-(2-methylpropyl)benzenesulfonamide;

4-((3,5-dimethylisoxazol-4-yl)methoxy)-N-(3,6-dimethylpyrazin-2-yl)-N-isobutylbenzenesulfonamide;

4-((3,5-dimethylisoxazol-4-yl)methoxy)-N-isobutyl-N-(4-methylpyrimidin-5-yl)benzenesulfonamide;

4-((3,5-dimethylisoxazol-4-yl)methoxy)-N-isobutyl-N-(2-methyl-6-(pyrrolidin-3-yl)pyridin-3-yl)benzenesulfonamide;

N-isobutyl-N-(5-isopropyl-3-methylpyridin-2-yl)-4-((tetrahydro-2H-pyran-4-yl)methoxy)benzenesulfonamide;

N-isobutyl-N-(3-methyl-5-(prop-1-en-2-yl)pyridin-2-yl)-4-((tetrahydro-2H-pyran-4-yl)methoxy)benzenesulfonamide;

N-isobutyl-N-(5-isopropylpyridin-2-yl)-4-((tetrahydro-2H-pyran-4-yl)methoxy)benzenesulfonamide;

N-(5-chloro-3-methylpyridin-2-yl)-N-isobutyl-4-((tetrahydro-2H-pyran-4-yl)methoxy)benzenesulfonamide;

4-((3,5-dimethylisoxazol-4-yl)methoxy)-N-isopentyl-N-(5-isopropylpyridin-2-yl)benzenesulfonamide;

N-(5-isopropylpyridin-2-yl)-N-(3-methylbutan-2-yl)-4-((tetrahydro-2H-pyran-4-yl)methoxy)benzenesulfonamide;

N-isobutyl-N-(5-isopropyl-3-methoxypyridin-2-yl)-4-((tetrahydro-2H-pyran-4-yl)methoxy)benzenesulfonamide;

N-(2-cyclopropylpyrimidin-5-yl)-4-((3,5-dimethylisoxazol-4-yl)methoxy)-N-isobutylbenzenesulfonamide;

N-(5-isopropylpyridin-2-yl)-N-(oxetan-3-ylmethyl)-4-((tetrahydro-2H-pyran-4-yl)methoxy)benzenesulfonamide;

4-{[(3,5-dimethyl-4-isoxazolyl)methyl]oxy}-N-(2-methylpropyl)-N-[2-(trifluoromethyl)-4-pyrimidinyl]benzenesulfonamide;

4-((3,5-dimethylisoxazol-4-yl)methoxy)-N-isobutyl-N-(pyrazin-2-yl)benzenesulfonamide;

4-((3,5-dimethylisoxazol-4-yl)methoxy)-N-isobutyl-N-(pyrimidin-5-yl)benzenesulfonamide;

4-((3,5-dimethylisoxazol-4-yl)methoxy)-N-isobutyl-N-(2-methylpyrimidin-5-yl)benzenesulfonamide;

4-((3,5-dimethylisoxazol-4-yl)methoxy)-N-isobutyl-N-(5-methylpyridin-3-yl)benzenesulfonamide;

N-(cyclobutylmethyl)-4-((3,5-dimethylisoxazol-4-yl)methoxy)-N-(5-isopropylpyridin-2-yl)benzenesulfonamide;

N-(6-cyclopropylpyridazin-3-yl)-4-((3,5-dimethylisoxazol-4-yl)methoxy)-N-isobutylbenzenesulfonamide;

4-((3,5-dimethylisoxazol-4-yl)methoxy)-N-(5-isopropylpyridin-2-yl)-N-(2-methylbutyl)benzenesulfonamide;

and 4-(1-hydroxy-2-((3-methyloxetan-3-yl)amino)ethyl)-N-isobutyl-N-(5-isopropylpyridin-2-yl)benzenesulfonamide.

17. The compound according to claim 1, or a pharmaceutically acceptable salt thereof, wherein $R_6$ is isoxazole, and further wherein $R_6$ may be unsubstituted or substituted with one or two substituents independently selected from halo and $CH_3$.

18. The compound according to claim 17 wherein the isoxazole is disubstituted with $CH_3$.

19. The compound according to claim 1, or a pharmaceutically acceptable salt thereof, wherein $R_6$ is tetrahydro-2H-pyran.

20. The compound according to claim 11, or a pharmaceutically acceptable salt thereof, wherein $R_6$ is isoxazole or tetrahydro-2H-pyran, and further wherein $R_6$ may be unsubstituted or substituted with one or two substituents independently selected from halo and $CH_3$.

21. The compound according to claim 8, or a pharmaceutically acceptable salt thereof, wherein b is 1.

22. The compound according to claim 21, or a pharmaceutically acceptable salt thereof, wherein $R_2$ is selected from the group consisting of isopropyl, isobutyl, isopentyl and 3-methylbutan-2-yl.

23. The compound according to claim 22, or a pharmaceutically acceptable salt thereof, wherein $R_6$ is isoxazole or tetrahydro-2H-pyran, and further wherein $R_6$ may be unsubstituted or substituted with one or two substituents independently selected from halo and $CH_3$.

24. A pharmaceutical composition comprising a) a compound according to claim 1, or a pharmaceutically acceptable salt thereof, and b) one or more pharmaceutically acceptable excipients.

25. A pharmaceutical composition comprising a) a compound according to claim 16, or a pharmaceutically acceptable salt thereof, and b) one or more pharmaceutically acceptable excipients.

26. A method of treatment of an inflammatory, metabolic or autoimmune disease mediated by RORγ comprising administering a therapeutically effective amount of a compound as defined in claim 1, or a pharmaceutically acceptable salt thereof.

27. The method of treatment according to claim 26, wherein the disease is asthma, chronic obstructive pulmonary disease (COPD), bronchitis, allergic rhinitis, atopic dermatitis, cystic fibrosis, lung allograph rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), inflammatory bowel syndrome (IBS), Sjorgen's syndrome, optic neuritis, type I diabetes, neuromyelitis optica, Myasthenia Gravis, uveitis, Guillain-Barre syndrome, psoriatic arthritis, Graves' disease or scleritis.

28. The method of treatment according to claim 27 wherein the disease is psoriasis.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence identified using molecular biology techniques.
<220> FEATURE:
<221> NAME/KEY: VARIANT
<222> LOCATION: 2, 3
<223> OTHER INFORMATION: Xaa = Any Amino Acid

<400> SEQUENCE: 1

Leu Xaa Xaa Leu Leu
 1               5

<210> SEQ ID NO 2
<211> LENGTH: 15
<212> TYPE: PRT
<213> ORGANISM: Artificial Sequence
<220> FEATURE:
<223> OTHER INFORMATION: Amino acid sequence identified using molecular biology techniques.

<400> SEQUENCE: 2

Met Lys Lys His His His His His His Leu Val Pro Arg Gly Ser
 1               5                  10                  15

<210> SEQ ID NO 3
<211> LENGTH: 25
<212> TYPE: PRT
<213> ORGANISM: Artificial Sequence
<220> FEATURE:
<223> OTHER INFORMATION: Amino acid sequence identified using molecular biology techniques.

<400> SEQUENCE: 3

Cys Pro Ser Ser His Ser Ser Leu Thr Glu Arg His Lys Ile Leu His
 1               5                  10                  15

Arg Leu Leu Gln Glu Gly Ser Pro Ser
            20                  25